US007695915B2

(12) United States Patent
Lau et al.

(10) Patent No.: US 7,695,915 B2
(45) Date of Patent: Apr. 13, 2010

(54) MOLECULAR PROGNOSTIC SIGNATURE FOR PREDICTING BREAST CANCER DISTANT METASTASIS, AND USES THEREOF

(75) Inventors: Kit Lau, Fremont, CA (US); Alice Wang, Lafayette, CA (US)

(73) Assignee: Celera Corporation, Alameda, CA (US)

( * ) Notice: Subject to any disclaimer, the term of this patent is extended or adjusted under 35 U.S.C. 154(b) by 191 days.

(21) Appl. No.: 12/012,530

(22) Filed: Jan. 31, 2008

(65) Prior Publication Data

US 2008/0206769 A1    Aug. 28, 2008

Related U.S. Application Data

(60) Provisional application No. 60/898,963, filed on Jan. 31, 2007.

(51) Int. Cl.
*C12Q 1/68*    (2006.01)
(52) U.S. Cl. .......................................................... 435/6
(58) Field of Classification Search ....................... None
See application file for complete search history.

(56) References Cited

U.S. PATENT DOCUMENTS

2005/0221398 A1    10/2005    Jacquemier et al.

OTHER PUBLICATIONS

Paik et al., N Engl J Med 2004, 351, pp. 2817.*
Dai et al., Cancer Res 2005, 65, pp. 4059-4066.*
van't Veer, Nature 2002, 415, pp. 530-536.*
Tutt et al., BMC Cancer (2008), vol. 8, p. 339.*
International Preliminary Report on Patentabilty issued in PCT/US2008/001339, dated Aug. 13, 2009.
International Search Report and Written Opinion dated Sep. 10, 2008.

* cited by examiner

*Primary Examiner*—Misook Yu

(57) ABSTRACT

The present invention is based on the discovery of a unique 14-gene molecular prognostic signature that is useful for predicting breast cancer metastasis. In particular, the present invention relates to methods and reagents for detecting and profiling the expression levels of these genes, and methods of using the expression level information in predicting risk of breast cancer metastasis.

23 Claims, 24 Drawing Sheets

Comparison of probability of distant metastasis in 10 years from 14-gene signature vs, 10-year relapse probability from Adjuvant! for untreated patients from Guy's Hospital Figure 2. ROC curve for predicting distant metastases in 5 years by MS(CV) in the training sample set from CPMC. AUC = 0.76 (0.65 – 0.87)

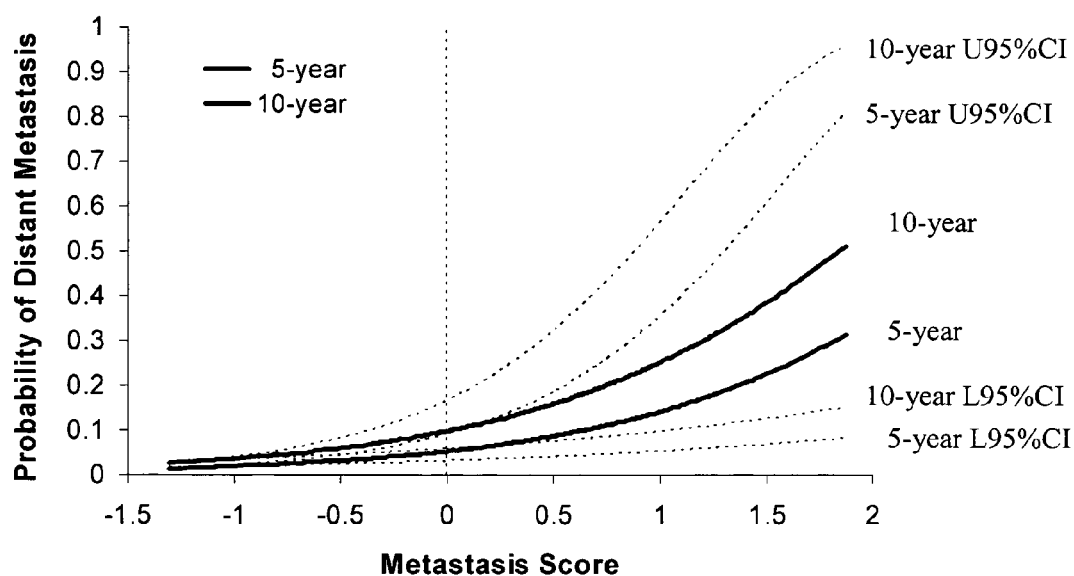
Figure 5. Probability of distant metastasis within 5 years and 10 years vs. Metastasis Score (MS) from 280 Guy's untreated patients Figure 6. Comparison of probability of distant metastasis in 10 years from 14-gene signature vs, 10-year relapse probability from Adjuvant! for untreated patients from Guy's Hospital
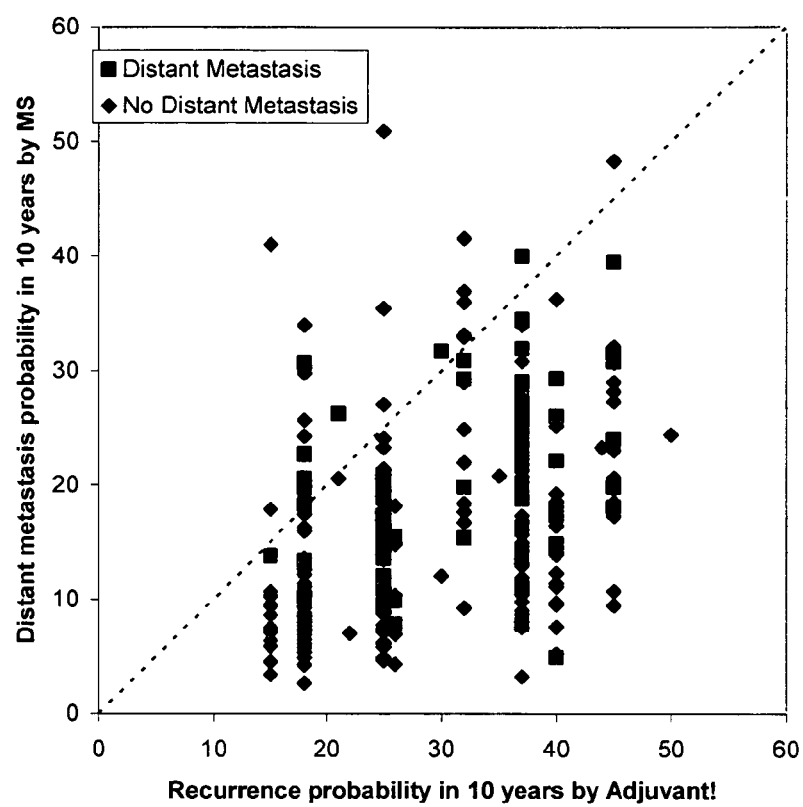

Figure 7. Kaplan-Meier curves for distant-metastasis-free survival in University of Muenster patients.
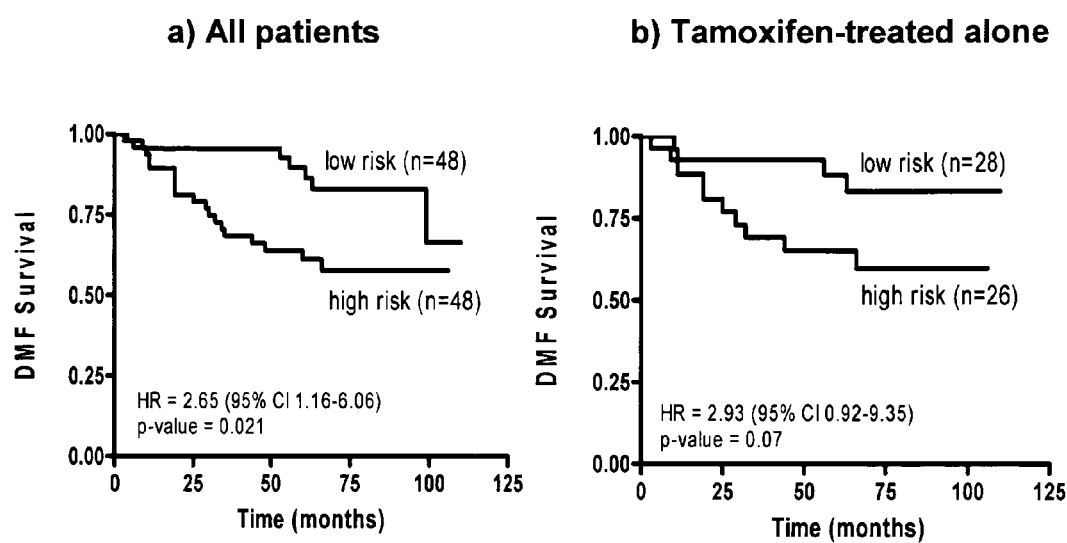

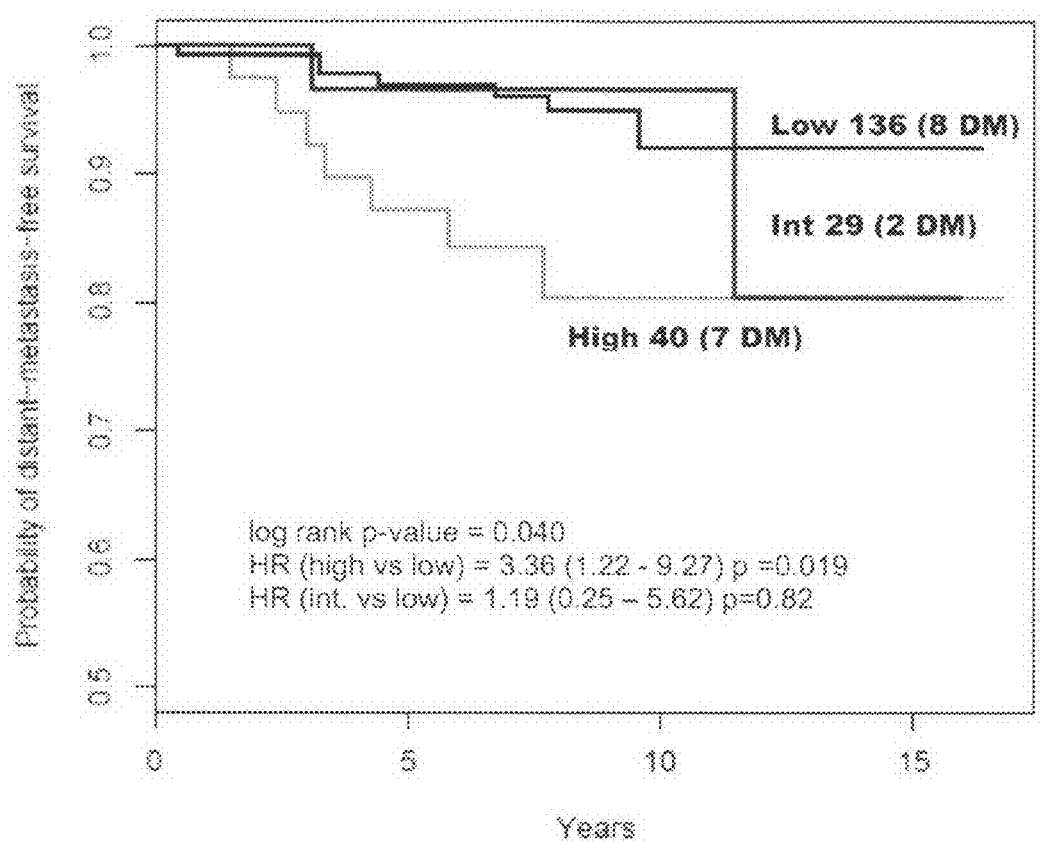
Figure S. Kaplan-Meier curves of distant-metastasis-free survival in 3 MS groups (high, intermediate, low) for 205 treated patients from Guy's Hospital

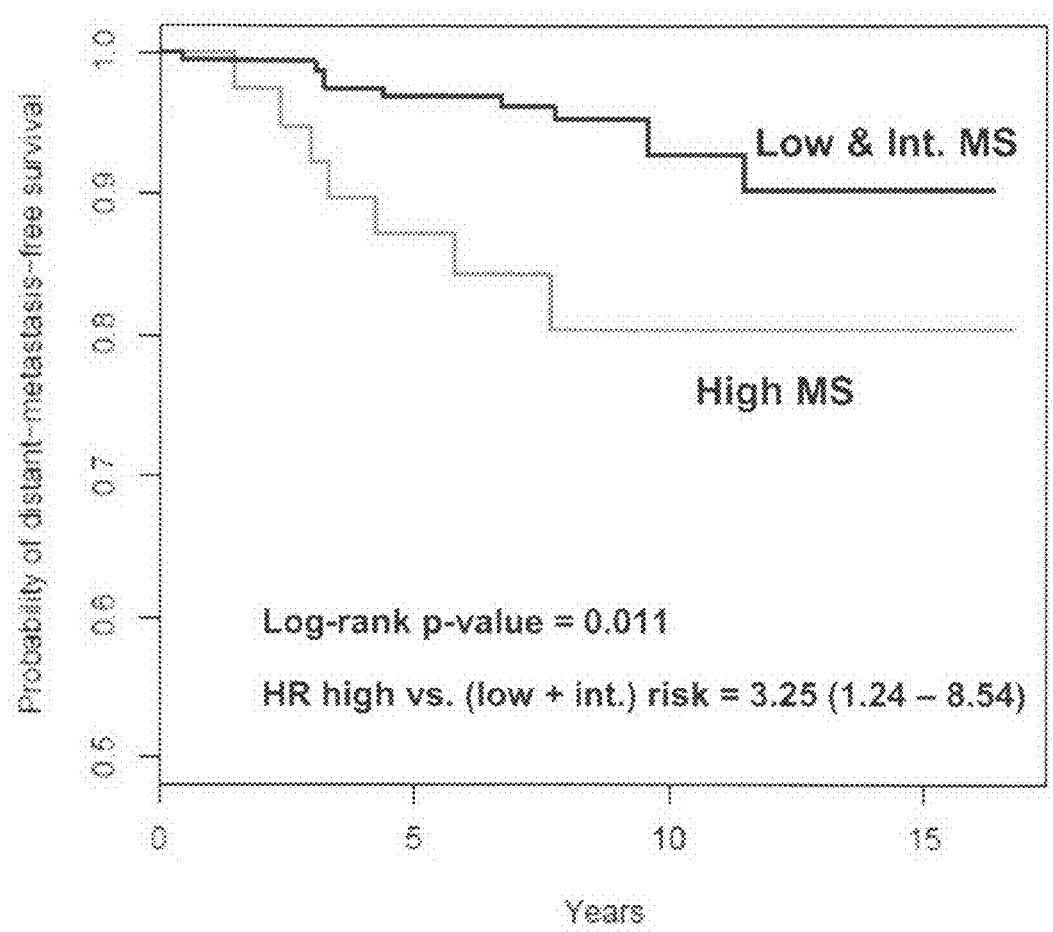
Figure 9. Kaplan-Meier curves of distant-metastasis-free survival in 2 risk groups (high and low) determined by MS for 205 treated patients from Guy's Hospital Figure 10. ROC curve of MS in Guy's treated samples, AUC = 0.7 (0.57 – 0.87)
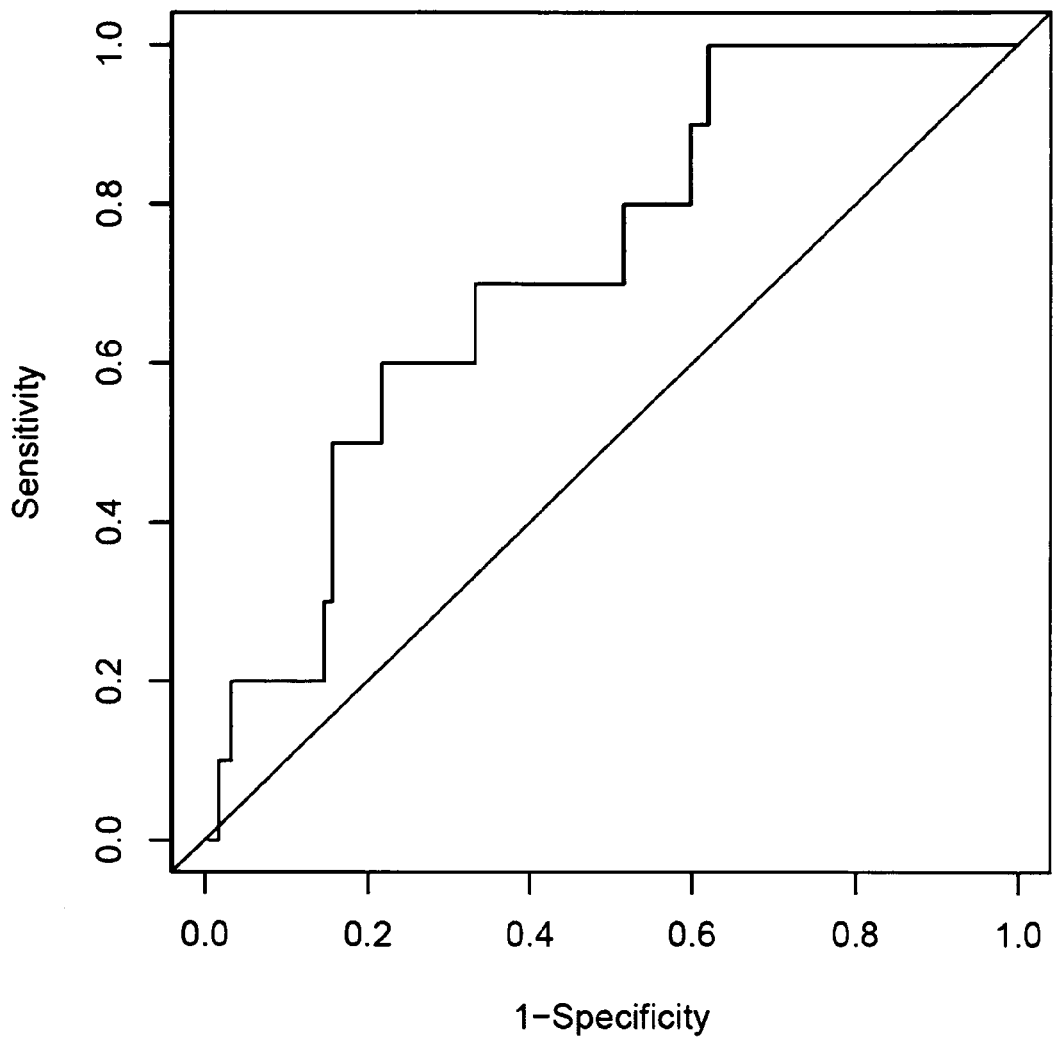

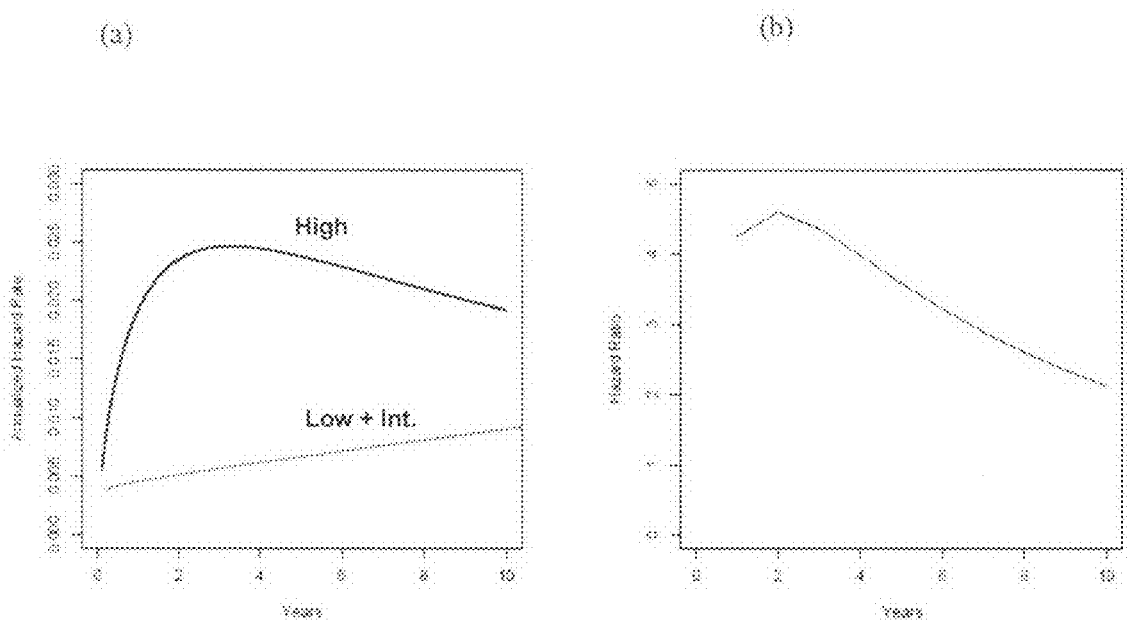
Figure 11. Time dependence of hazard ratios of high vs. low risk groups by MS in Guy's treated samples

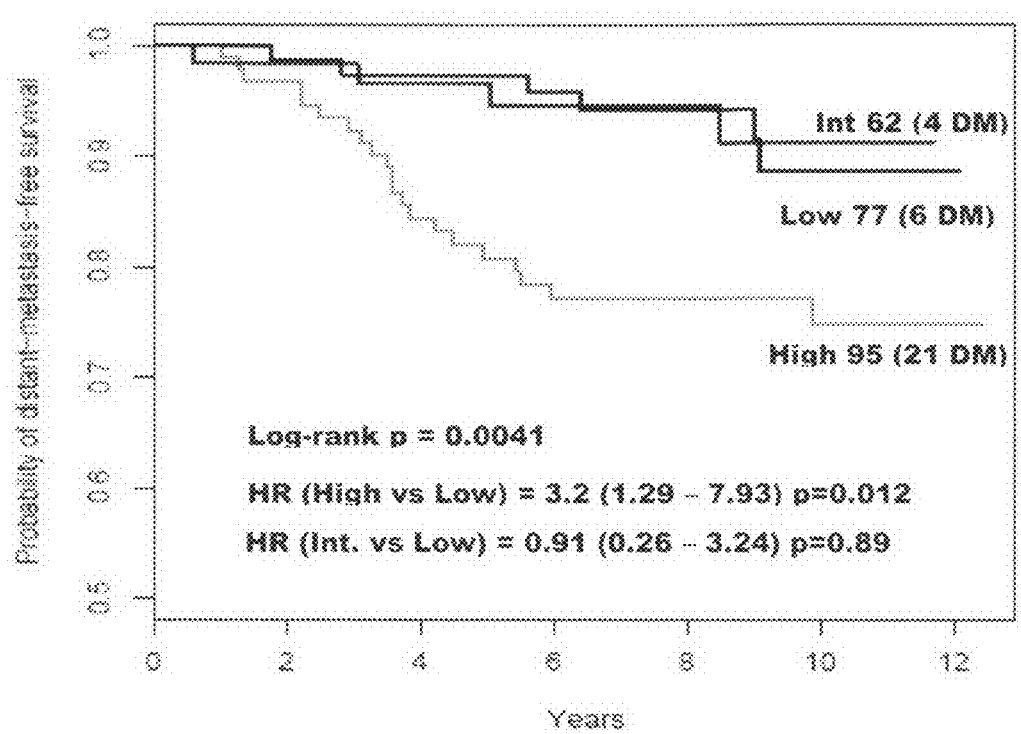
Figure 12. Kaplan-Meier curves of distant-metastasis-free survival (DMFS) for three MS groups (high, intermediate and low) in 234 Japanese samples Figure 13. Kaplan-Meier curves of distant-metastasis-free survival (DMFS) for two risk groups (high MS and a combination of intermediate and low MS) in 234 Japanese samples
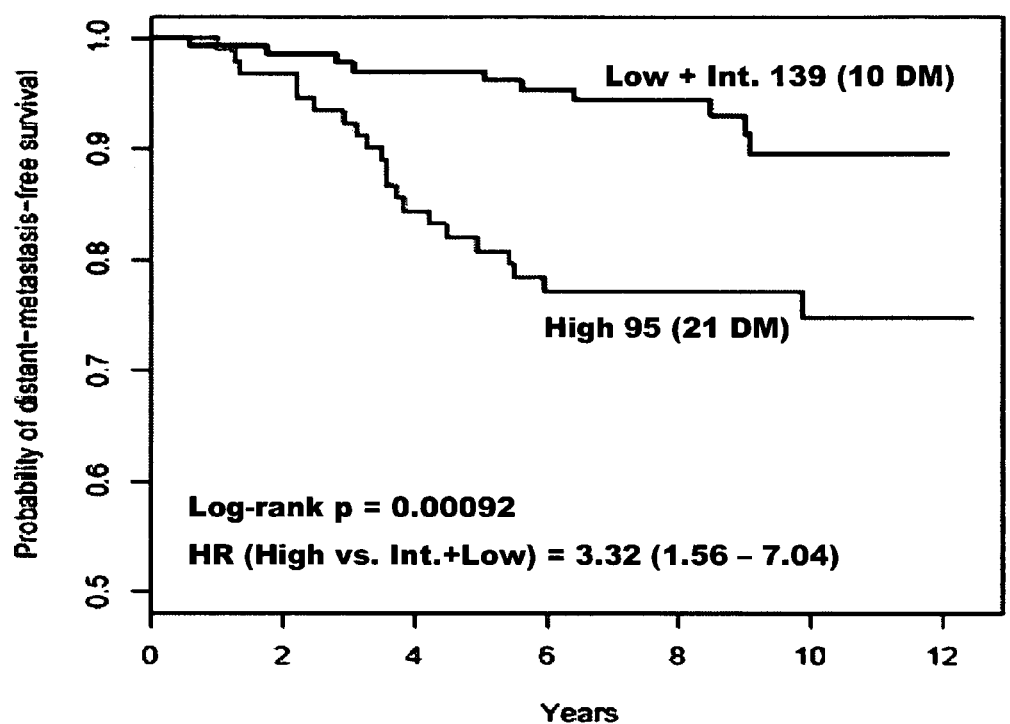

Figure 14. ROC curve of MS to predict distant metastasis in 5 years for Japanese patients. AUC = 0.73 (0.63 – 0.84)
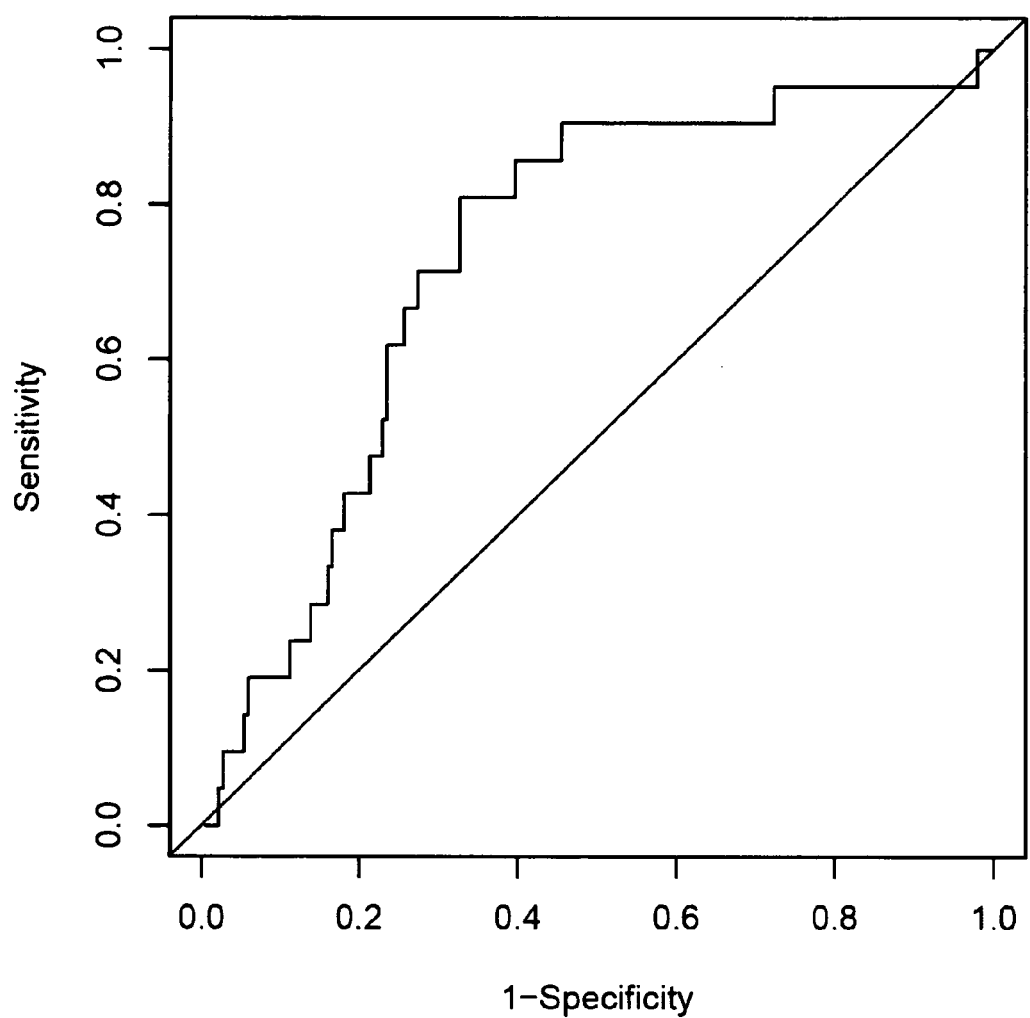

Figure 15. Annualized hazard rate for MS groups and hazard ratio of high vs. low risk groups as a function of time
(a)                    (b)
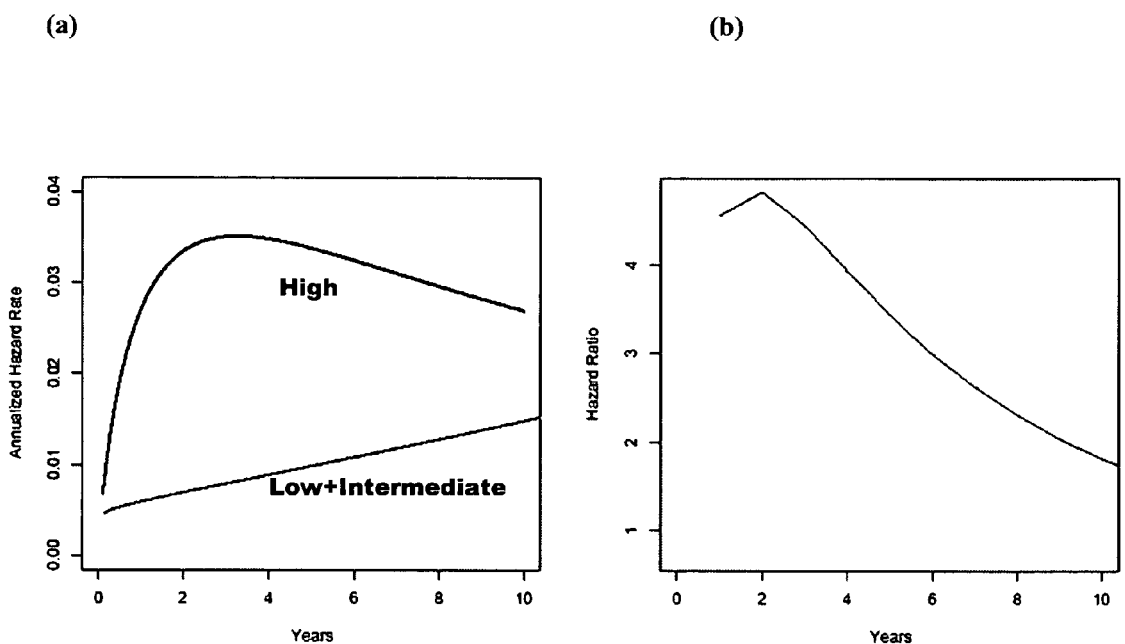

SEQUENCE LISTING

<160> NUMBER OF SEQ ID NOS: 34

<210> SEQ ID NO 1
<211> LENGTH: 17
<212> TYPE: DNA
<213> ORGANISM: Homo Sapiens

<400> SEQUENCE: 1
catggtggtg ccttcaa                                                    17

<210> SEQ ID NO 2
<211> LENGTH: 23
<212> TYPE: DNA
<213> ORGANISM: Homo Sapiens

<400> SEQUENCE: 2
gctgaataca tgtgagacga caa                                             23

<210> SEQ ID NO 3
<211> LENGTH: 22
<212> TYPE: DNA
<213> ORGANISM: Homo Sapiens

<400> SEQUENCE: 3
gccaaatacc tgatggaact aa                                              22

```
<210> SEQ ID NO 4
<211> LENGTH: 20
<212> TYPE: DNA
<213> ORGANISM: Homo Sapiens

<400> SEQUENCE: 4
ctcctgctgc aatttgagaa                                              20

<210> SEQ ID NO 5
<211> LENGTH: 16
<212> TYPE: DNA
<213> ORGANISM: Homo Sapiens

<400> SEQUENCE: 5
cagtcggcgg agacaa                                                  16

<210> SEQ ID NO 6
<211> LENGTH: 22
<212> TYPE: DNA
<213> ORGANISM: Homo Sapiens

<400> SEQUENCE: 6
aagaggtgtg tgctcttctg aa                                           22

<210> SEQ ID NO 7
<211> LENGTH: 23
<212> TYPE: DNA
<213> ORGANISM: Homo Sapiens

<400> SEQUENCE: 7
aaagtgacct gtgagagatt gaa                                          23

<210> SEQ ID NO 8
<211> LENGTH: 15
<212> TYPE: DNA
<213> ORGANISM: Homo Sapiens

<400> SEQUENCE: 8
cgccctgccc aacaa                                                   15

<210> SEQ ID NO 9
<211> LENGTH: 18
<212> TYPE: DNA
<213> ORGANISM: Homo Sapiens

<400> SEQUENCE: 9
ttatcccatc gccttgaa                                                18

<210> SEQ ID NO 10
<211> LENGTH: 20
<212> TYPE: DNA
<213> ORGANISM: Homo Sapiens

<400> SEQUENCE: 10
tgctccacac catgttgtaa                                              20

<210> SEQ ID NO 11
<211> LENGTH: 16
<212> TYPE: DNA
<213> ORGANISM: Homo Sapiens

<400> SEQUENCE: 11
agagacgggc ccagaa                                                  16
```

<210> SEQ ID NO 12
<211> LENGTH: 24
<212> TYPE: DNA
<213> ORGANISM: Homo Sapiens

<400> SEQUENCE: 12
caacagttga tctggattca ctaa                                    24

<210> SEQ ID NO 13
<211> LENGTH: 15
<212> TYPE: DNA
<213> ORGANISM: Homo Sapiens

<400> SEQUENCE: 13
gcggagcccc atcaa                                              15

<210> SEQ ID NO 14
<211> LENGTH: 21
<212> TYPE: DNA
<213> ORGANISM: Homo Sapiens

<400> SEQUENCE: 14
catcctcatc cacaatgtca a                                       21

<210> SEQ ID NO 15
<211> LENGTH: 20
<212> TYPE: DNA
<213> ORGANISM: Homo Sapiens

<400> SEQUENCE: 15
cacttctgct gcactgcttt                                         20

<210> SEQ ID NO 16
<211> LENGTH: 22
<212> TYPE: DNA
<213> ORGANISM: Homo Sapiens

<400> SEQUENCE: 16
ggatgtggct accattttgt tt                                      22

<210> SEQ ID NO 17
<211> LENGTH: 18
<212> TYPE: DNA
<213> ORGANISM: Homo Sapiens

<400> SEQUENCE: 17
ctacctgccc cctgagtt                                           18

<210> SEQ ID NO 18
<211> LENGTH: 21
<212> TYPE: DNA
<213> ORGANISM: Homo Sapiens

<400> SEQUENCE: 18
agcatcatga caaggacaga a                                       21

<210> SEQ ID NO 19
<211> LENGTH: 19
<212> TYPE: DNA
<213> ORGANISM: Homo Sapiens

<400> SEQUENCE: 19

```
tgtccaagct gtggtcaaa                                              19
```

<210> SEQ ID NO 20
<211> LENGTH: 19
<212> TYPE: DNA
<213> ORGANISM: Homo Sapiens

<400> SEQUENCE: 20

```
tctccagggg tgatcagaa                                              19
```

<210> SEQ ID NO 21
<211> LENGTH: 18
<212> TYPE: DNA
<213> ORGANISM: Homo Sapiens

<400> SEQUENCE: 21

```
gactgcgaaa agctggaa                                               18
```

<210> SEQ ID NO 22
<211> LENGTH: 20
<212> TYPE: DNA
<213> ORGANISM: Homo Sapiens

<400> SEQUENCE: 22

```
ttgctcctcg cttagttgaa                                             20
```

<210> SEQ ID NO 23
<211> LENGTH: 19
<212> TYPE: DNA
<213> ORGANISM: Homo Sapiens

<400> SEQUENCE: 23

```
tttggcagca gctagagaa                                              19
```

<210> SEQ ID NO 24
<211> LENGTH: 22
<212> TYPE: DNA
<213> ORGANISM: Homo Sapiens

<400> SEQUENCE: 24

```
cacgttcatc agatgcattt aa                                          22
```

<210> SEQ ID NO 25
<211> LENGTH: 20
<212> TYPE: DNA
<213> ORGANISM: Homo Sapiens

<400> SEQUENCE: 25

```
gatggtttcc acaggaacaa                                             20
```

<210> SEQ ID NO 26
<211> LENGTH: 18
<212> TYPE: DNA
<213> ORGANISM: Homo Sapiens

<400> SEQUENCE: 26

```
ggatccaagt cccagcaa                                               18
```

<210> SEQ ID NO 27
<211> LENGTH: 18
<212> TYPE: DNA
<213> ORGANISM: Homo Sapiens

<400> SEQUENCE: 27

```
cctgctgatc caccctaa                                                   18

<210> SEQ ID NO 28
<211> LENGTH: 23
<212> TYPE: DNA
<213> ORGANISM: Homo Sapiens

<400> SEQUENCE: 28
gcatactcct cgtagttctc caa                                             23

<210> SEQ ID NO 29
<211> LENGTH: 20
<212> TYPE: DNA
<213> ORGANISM: Homo Sapiens

<400> SEQUENCE: 29
cactggatcc caagagtgaa                                                 20

<210> SEQ ID NO 30
<211> LENGTH: 22
<212> TYPE: DNA
<213> ORGANISM: Homo Sapiens

<400> SEQUENCE: 30
tgatcccact ccaagtctag aa                                              22

<210> SEQ ID NO 31
<211> LENGTH: 22
<212> TYPE: DNA
<213> ORGANISM: Homo Sapiens

<400> SEQUENCE: 31
tggacaagta atctctggtc aa                                              22

<210> SEQ ID NO 32
<211> LENGTH: 19
<212> TYPE: DNA
<213> ORGANISM: Homo Sapiens

<400> SEQUENCE: 32
gtatccgtac ctccgcaaa                                                  19

<210> SEQ ID NO 33
<211> LENGTH: 18
<212> TYPE: DNA
<213> ORGANISM: Homo Sapiens

<400> SEQUENCE: 33
tgccaatgca ggaaagaa                                                   18

<210> SEQ ID NO 34
<211> LENGTH: 25
<212> TYPE: DNA
<213> ORGANISM: Homo Sapiens

<400> SEQUENCE: 34
tggtatctcc tgtgtaccta acaaa                                           25
```

MOLECULAR PROGNOSTIC SIGNATURE FOR PREDICTING BREAST CANCER DISTANT METASTASIS, AND USES THEREOF

CROSS-REFERENCE TO RELATED APPLICATIONS

This application claims the benefit of U.S. provisional application Ser. No. 60/898,963, filed on Jan. 31, 2007, the content of which is hereby incorporated by reference in its entirety into this application.

FIELD OF THE INVENTION

The present invention relates to prognosis of breast cancer metastasis. In particular, the present invention relates to a multi-gene prognostic signature that is useful in predicting risk of metastasis of a breast cancer patient's node-negative estrogen receptor (ER)-positive tumor. The multi-gene prognostic signature comprises 14 genes, whose mRNA in a breast cancer patient's ER-positive tumor can be obtained from formalin-fixed, paraffin-embedded (FFPE) tissue sections, and their expression levels measured by methods known in the art. Thus, the present invention is amenable for use in routine clinical laboratory testing for assessing the risk of distant metastasis of node-negative ER-positive breast cancer.

BACKGROUND OF THE INVENTION

Breast cancer is a complex and heterogeneous disease. Early detection of breast cancer improves the chances of successful treatment and recovery. Routine screening mammography has increased the detection of Stage I breast cancers and correspondingly, many more women are being diagnosed with lymph node-negative tumors. (B. Cady, 1997, *Surg Oncol Clin N Am* 6:195-202). About 43% of the approximately 240,000 women in the United States diagnosed with breast cancer each year are node-negative.

Based on the current guidelines, 85-90% of node-negative patients are candidates for systemic adjuvant therapy after surgery. Such systemic adjuvant therapy may include chemotherapy and hormonal therapy. However, about 60-70% of women with node-negative breast cancer who receive local treatment (mastectomy or lumpectomy and radiation) will not experience distant recurrence. Treatment decisions for breast cancer patients benefit from the assessment of each patient's risk for metastasis and response to treatment using multiple clinical and histopathological parameters.

Several recent studies have used microarrays to demonstrate that a patient's gene expression profile can also provide useful prognostic information. A subset of these studies has received focused attention due to their size, and the extent of their validation. (L J van't Veer, H. Dai et al., 2002, *Nature* 415:530-536; M J van de Vijver, Y D He et al., 2002, *N Engl J Med* 347:1999-2009; Y. Wang, J G Klijn et al., 2005, *Lancet* 365:671-679; H. Dai, L J van't Veer et al., 2005, *Cancer Res* 15:4059-4066; and H Y Chang, D S Nuyten et al., 2005, *Proc Natl Acad Sci USA* 102:3738-3743).

The resulting confidence garnered for the 70-gene prognostic signature identified by van't Veer, Dai et al. (2002, *Nature* 415:530-536) has led to its incorporation into a European trial, the Microarray for Node-Negative Disease May Avoid Chemotherapy (MINDACT). Likewise, the PCR-based, 21-gene predictive signature described by S P Paik, S. Shak et al (2004, *N Engl J Med* 351:2817-2826) has been included in a phase III trial by The Breast Cancer Intergroup of North America (Program for the Assessment of Clinical Cancer Tests (PACCT). (V G Kaklamani and W J Gradishar, 2006, *Curr Treat Options Oncol* 7:123-8).

The 21-gene predictive signature (including 5 normalization genes) by SP Paik (2004, *N Engl J Med* 351:2817-2826) was derived from Tamoxifen-treated patients. The independence of that signature has drawn concern due to its substantial overlap with genes and/or proteins already used in conventional immunohistochemistry (IHC) tests. (D R Carrizosa and L A Carey, 2005, *The American Journal of Oncology Review* 4:7-10). The standard hormonal therapy for ER-positive breast cancer patients is changing from Tamoxifen alone, to sequential use of Tamoxifen plus aromatase inhibitors, or aromatase inhibitors alone. (E P Winer, C. Hudis et al., 2005, *J Clin Oncol* 23: 619-629; S M Swain, 2005, *N Engl J Med* 353:2807-9). A prognostic tool that is independent of Tamoxifen treatment can be important in providing a measure of the baseline risk for patients who plan on taking aromatase inhibitors.

Thus, there is a need for a gene-based prognostic assay that can be used for routine clinical laboratory testing in predicting the risk of distant metastasis in breast cancer patients. Ideally, the assay would require the measurement of expression levels of a relatively small number of genes, and the mRNA encoded by such genes can be readily obtained from tumor tissues preserved by routine collection methods such as FFPE tumor sections. Information of the risk for distant metastasis can be used in guiding treatment strategies for breast cancer patients, particularly early stage lymph node-negative patients, such that patients who are at higher risk of distant metastasis are treated properly, and patients who are at lower risk of distant metastasis may be spared the side effects of certain treatments.

SUMMARY OF THE INVENTION

The present invention relates to a 14-gene signature for predicting risk of metastasis of ER-positive tumors in breast cancer patients. The invention is based, in part, on studies of early stage, lymph node-negative, ER-positive patients who most need additional information to guide therapeutic decisions following primary diagnosis. The fourteen genes in the molecular signature of the present invention are disclosed in Table 2. One skilled in the art can perform expression profiling on the 14 genes described herein, using RNA obtained from a number of possible sources, and then insert the expression data into the provided algorithm to determine a prognostic metastasis score.

In one aspect of the invention, it relates to a method of determining risk associated with tumor metastasis in a breast cancer patient, comprising measuring mRNA expression of the genes known as CENPA, PKMYT1, MELK, MYBL2, BUB1, RACGAP1, TK1, UBE2S, DC13, RFC4, PRR11, DLAPH3, ORC6L and CCNB1 in estrogen receptor-positive tumor cells of the breast cancer patient, and predicting risk of tumor metastasis based on mRNA expression levels of said genes.

In another aspect of the invention, it relates to a method of determining risk associated with tumor metastasis in a breast cancer patient, comprising measuring the expression level of genes CENPA, PKMYT1, MELK, MYBL2, BUB1, RACGAP1, TK1, UBE2S, DC13, RFC4, PRR11, DIAPH3, ORC6L and CCNB1 in estrogen receptor-positive tumor cells of said breast cancer patient, thereby obtaining a metastasis score (MS) based upon the expression levels of said genes, and determining risk of tumor metastasis for said breast cancer patient by comparing said metastasis score to a predefined metastasis score cut point (MS Threshold).

In a further aspect of the invention, the breast cancer patient is determined to have an increased risk of tumor metastasis if its MS is higher than the predefined MS Threshold.

In another aspect of the invention, the breast cancer patient is determined to have a decreased risk of tumor metastasis if its MS is lower than the predefined MS Threshold.

In one aspect of the invention, it relates to a method of determining risk associated with tumor metastasis in a breast cancer patient, in which mRNA of the 14-gene signature is obtained from ER-positive tumor cells, reverse transcribed to cDNA, and detected by polymerase chain reaction amplification.

In another aspect of the invention, it relates to a method of determining risk associated with tumor metastasis in a breast cancer patient, in which mRNA of ER-positive tumor cells is reverse transcribed and amplified by the two primers associated with each gene as presented in Table 3, SEQ ID NOS. 1-34.

In another aspect of the invention, it relates to a method of determining risk associated with tumor metastasis in a breast cancer patient, in which measurements of mRNA expression from ER-positive tumor cells are normalized against the mRNA expression of any one of the genes known as NUP214, PPIG and SLU7, or a combination thereof, as endogenous control(s).

In another aspect of the invention, it relates to a method of determining risk associated with tumor metastasis in a breast cancer patient, in which mRNA expression from ER-positive tumor cells is detected by a microarray.

In another aspect of the invention, it relates to a method of determining risk associated with tumor metastasis in a breast cancer patient, in which the mRNA expression is computed into a metastasis score (MS) by the following:

$$MS = a0 + \sum_{i=1}^{M} ai * Gi$$

where M=14, Gi=the standardized expression level of each gene (i) of the fourteen said genes, a0=0.022, and ai corresponds to the value presented in Table 2 for each of the genes in the 14-gene signature.

In another aspect of the invention, it relates to a method of determining risk associated with tumor metastasis in a breast cancer patient, in which the mRNA expression is computed into a metastasis score (MS) by the following:

$$MS = a0 + b * \left[\sum_{i=1}^{M} ai * Gi\right] \quad \text{Equation 1}$$

where M=14, Gi=the standardized expression level of each gene (i) of the fourteen said genes, a0=0.022, b=−0.251 and ai corresponds to the value presented in Table 2 for each of the genes in the 14-gene signature. Standardized expression level is obtained by subtracting the mean expression of that gene in the training set from the expression level measured in $\Delta(\Delta Ct)$ and then divided by the standard deviation of the gene expression in that gene. The mean and standard deviation of gene expression for each gene in the training set were presented in Table 4. Equation 1 was used in Examples 1, 2 and 3.

In a further aspect of the invention, the MS formula can assume the following definition $$MS = a0 + b * \left[\sum_{i=1}^{M} ai * Gi\right] \quad \text{Equation 2}$$

where M=14, Gi=expression level measured in $\Delta(\Delta Ct)$ of each gene (i) of the fourteen said genes, a=0.8657, b=−0.04778, ai=1 for all genes. Equation 2 was used in Examples 4 and 5.

In a further aspect of the invention, the MS formula can have a0=0, b=−1 and ai=1.

In another aspect of the invention, it relates to a method of determining risk associated with tumor metastasis in a breast cancer patient using expression profiling of the 14 genes mentioned above, in which the expression level Gi of each gene (i) is computed into a gene expression value Gi by the following:

$$\Delta(\Delta Ct) = (Ct_{GOI} - Ct_{EC})_{test\ RNA} - (Ct_{GOI} - Ct_{EC})_{ref\ RNA} \quad \text{Equation 4}$$

where Ct is the PCR threshold cycle of exponential target amplification, GOI=gene of interest, EC=endogenous control, test RNA=patient sample RNA, ref RNA=reference RNA.

In another aspect of the invention, it relates to a method of determining risk associated with tumor metastasis in a breast cancer patient using expression profiling of the 14 genes mentioned above, in which the expression level Gi of each gene (i) is combined into a single value of MS Score, wherein a patient with a MS score higher than the relevant MS Threshold or cut point would be at a higher risk for tumor metastasis.

In one aspect of the invention, it relates to a kit comprising reagents for the detection of the expression levels of genes CENPA, PKMYT1, MELK, MYBL2, BUB1, RACGAP1, TK1, UBE2S, DC13, RFC4, PRR11, DIAPH3, ORC6L and CCNB1, and enzyme; and a buffer.

In another aspect of the invention, it relates to a microarray comprising polynucleotides hybridizing to genes CENPA, PKMYT1, MELK, MYBL2, BUB1, RACGAP1, TK1, UBE2S, DC13, RFC4, PRR11, DIAPH3, ORC6L and CCNB1

Sequence Listing

The attached Sequence Listing is herein incorporated by reference in its entirety. The Sequence Listing provides the oligonucleotide sequences (SEQ ID NOS: 1-34) as shown in Table 3. These oligonucleotides are exemplary primers in the RT-PCR amplification of the genes listed in Table 3.

BRIEF DESCRIPTIONS OF THE FIGURES

Figure 3:
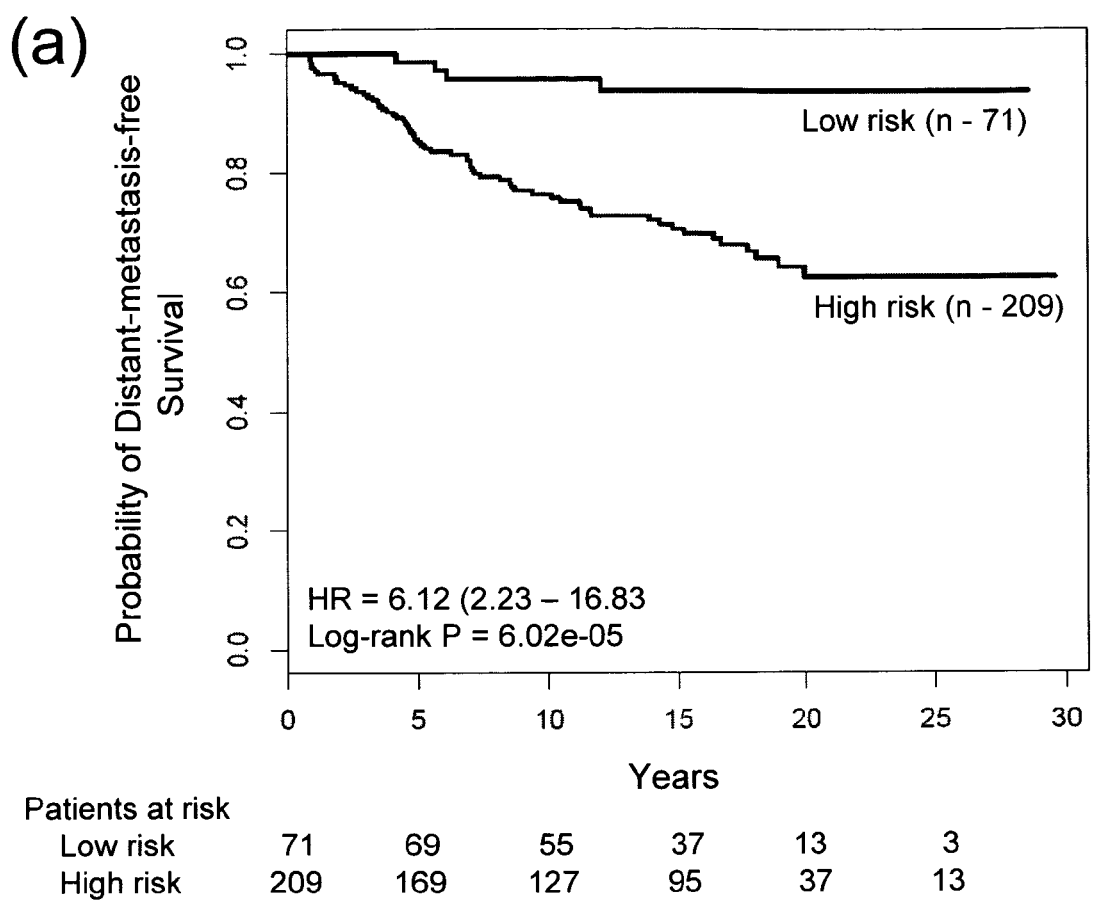
Figure 3:
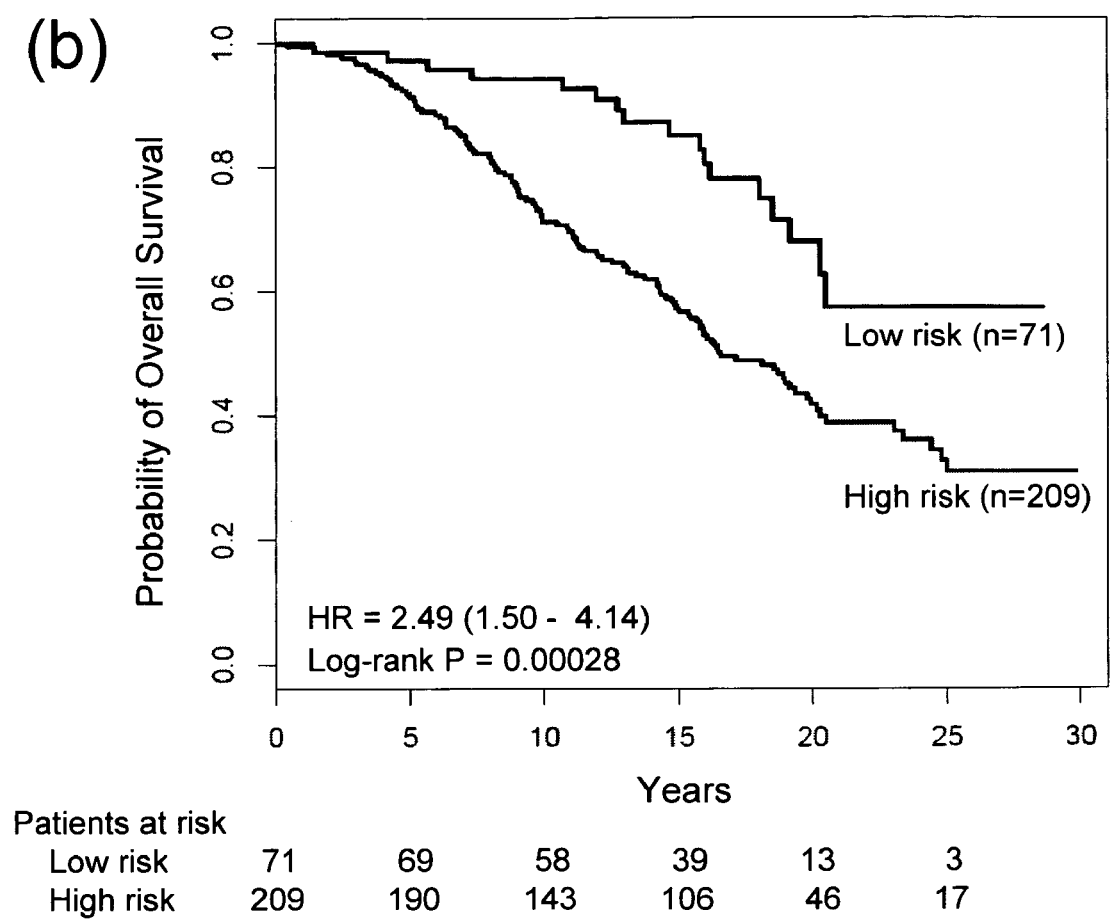
Figure 3:
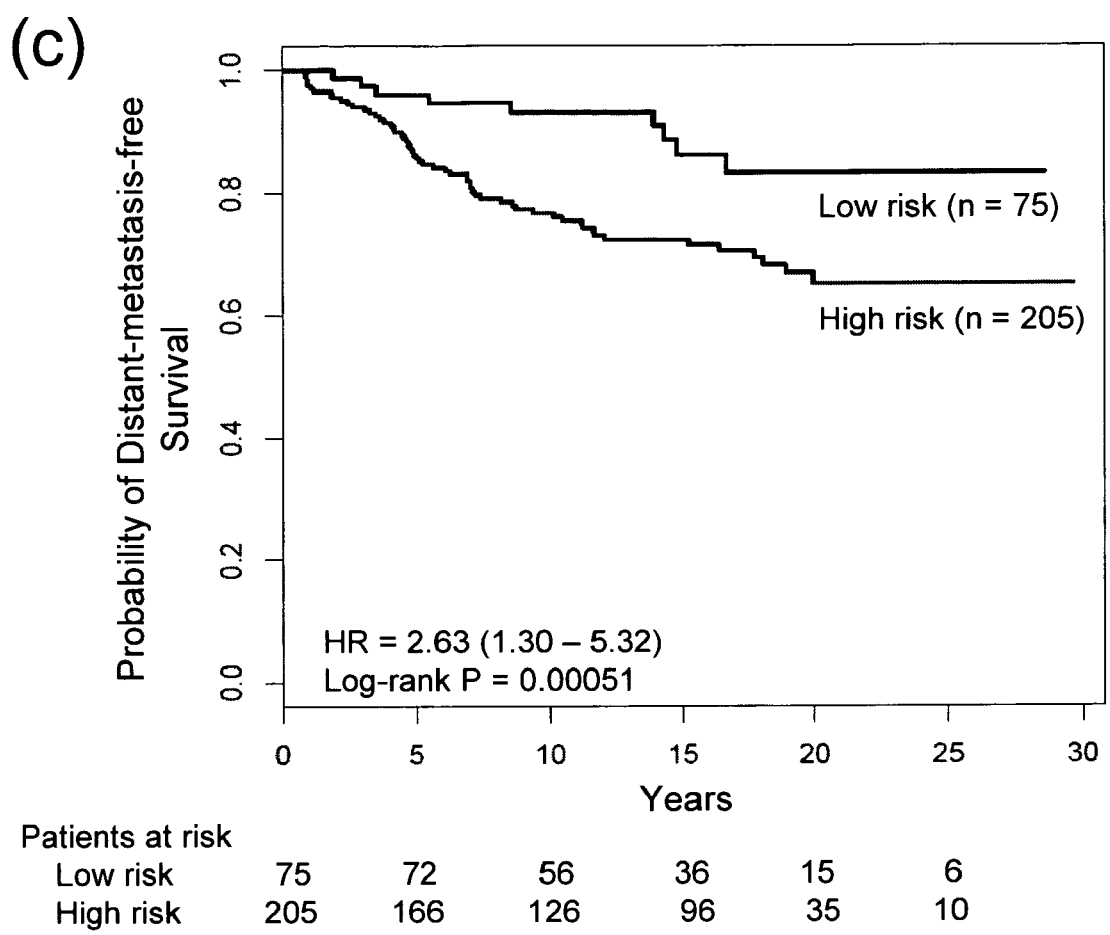
Figure 3:
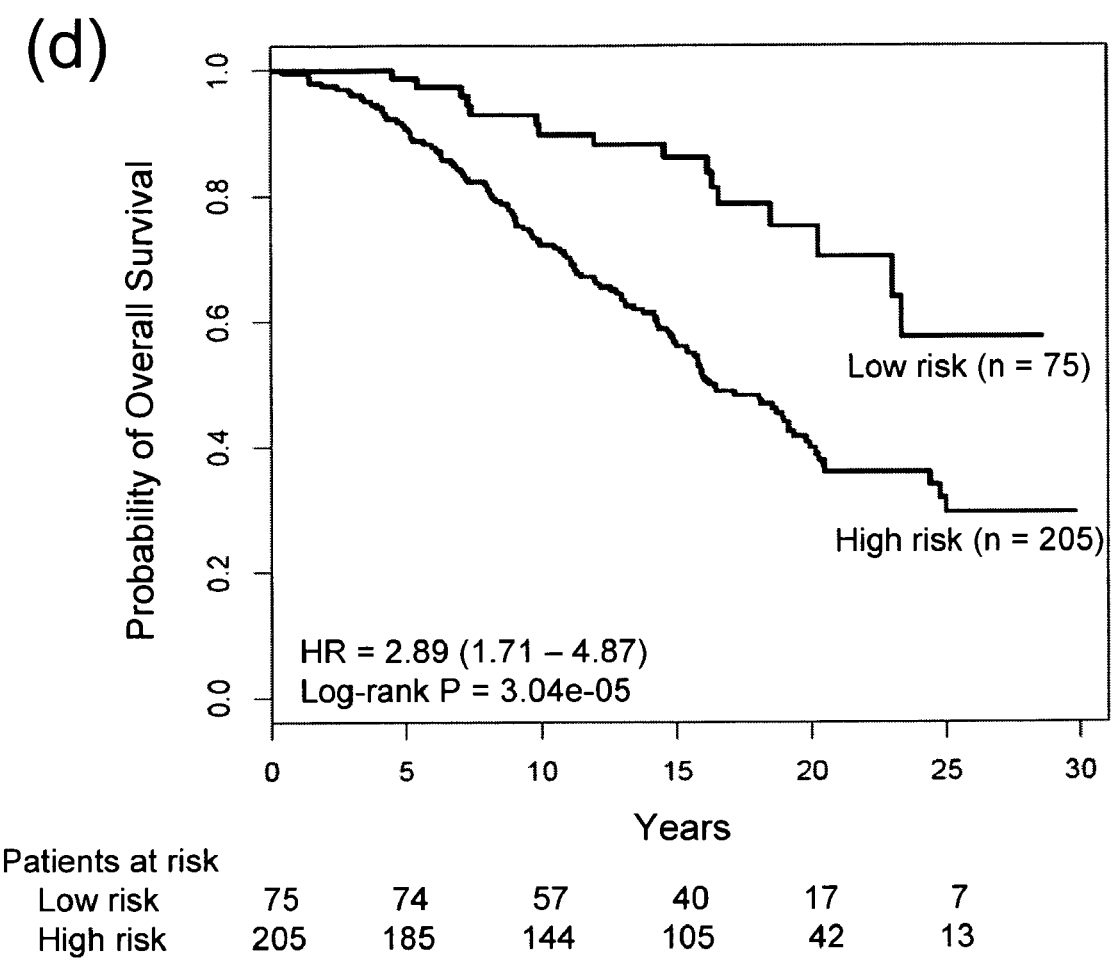

FIG. 3 shows Kaplan-Meier curves by risk groups defined by the gene signature and Adjuvant! in 280 untreated patients from Guy's Hospital. Specifically, FIGS. 3a) and b) describe results using the 14 gene signature, and FIGS. 3c) and d) describe results using the Adjuvant! factors. a) Time to distant metastases (DMFS) by MS risk groups b) Overall survival by MS risk groups c) Time to distant metastases (DMFS) by Adjuvant! risk groups d) Overall survival by Adjuvant! risk groups.

Figure 4:
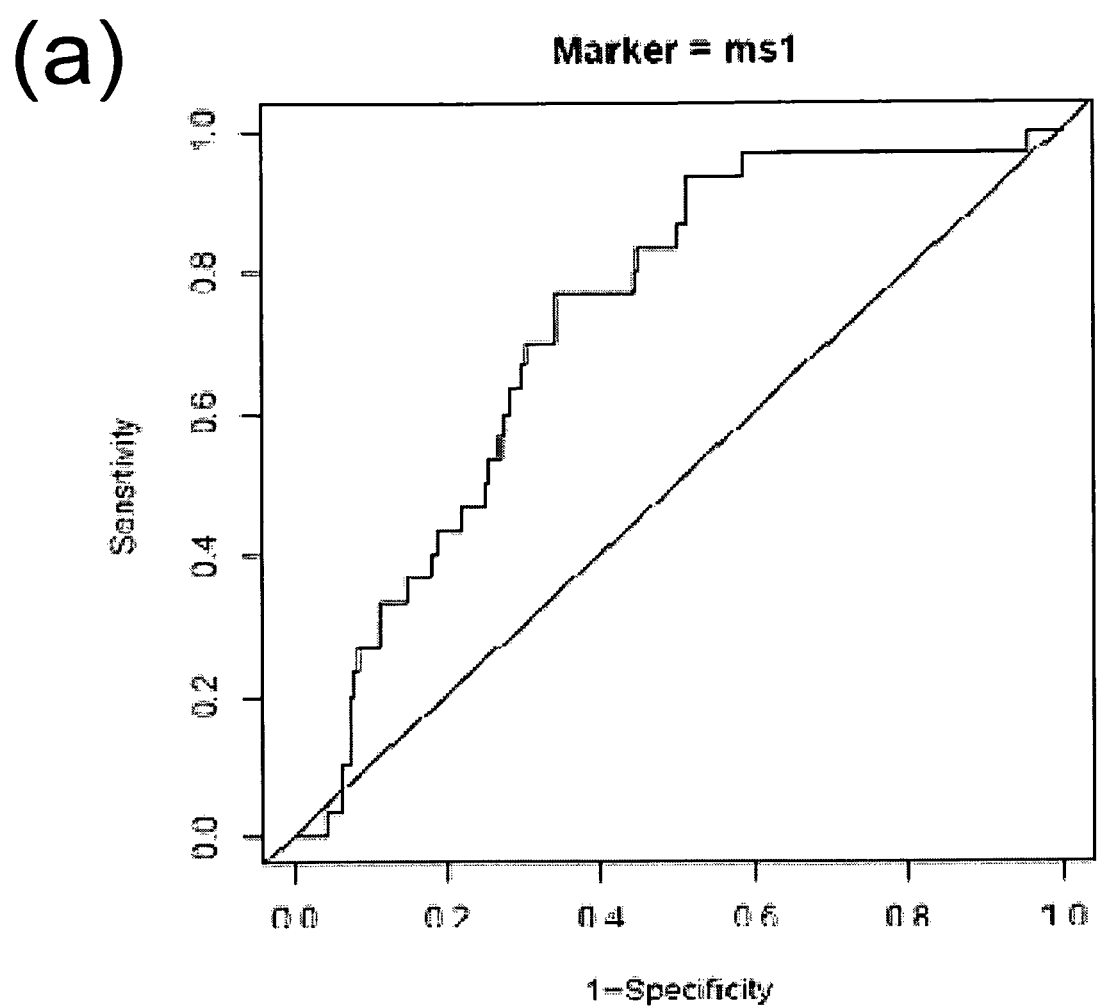
Figure 4:
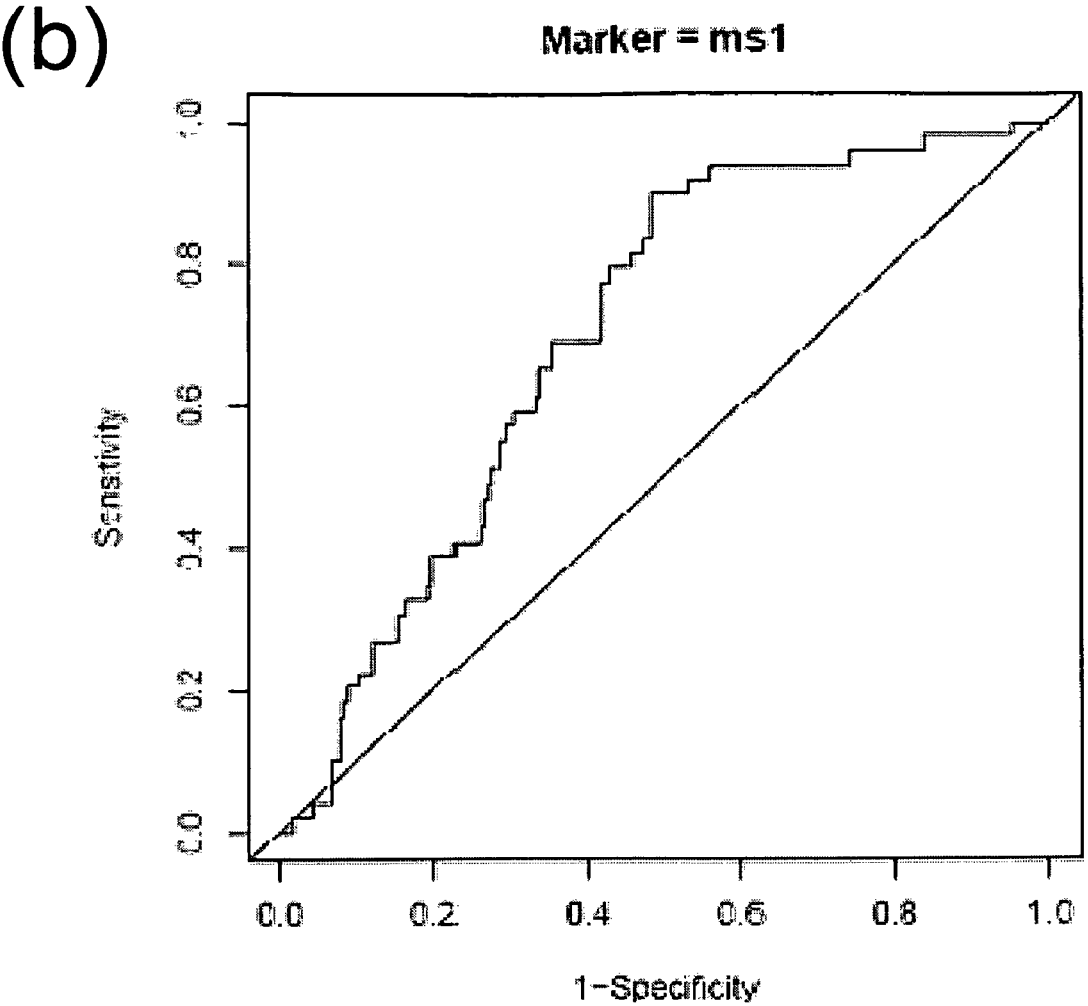
Figure 4:
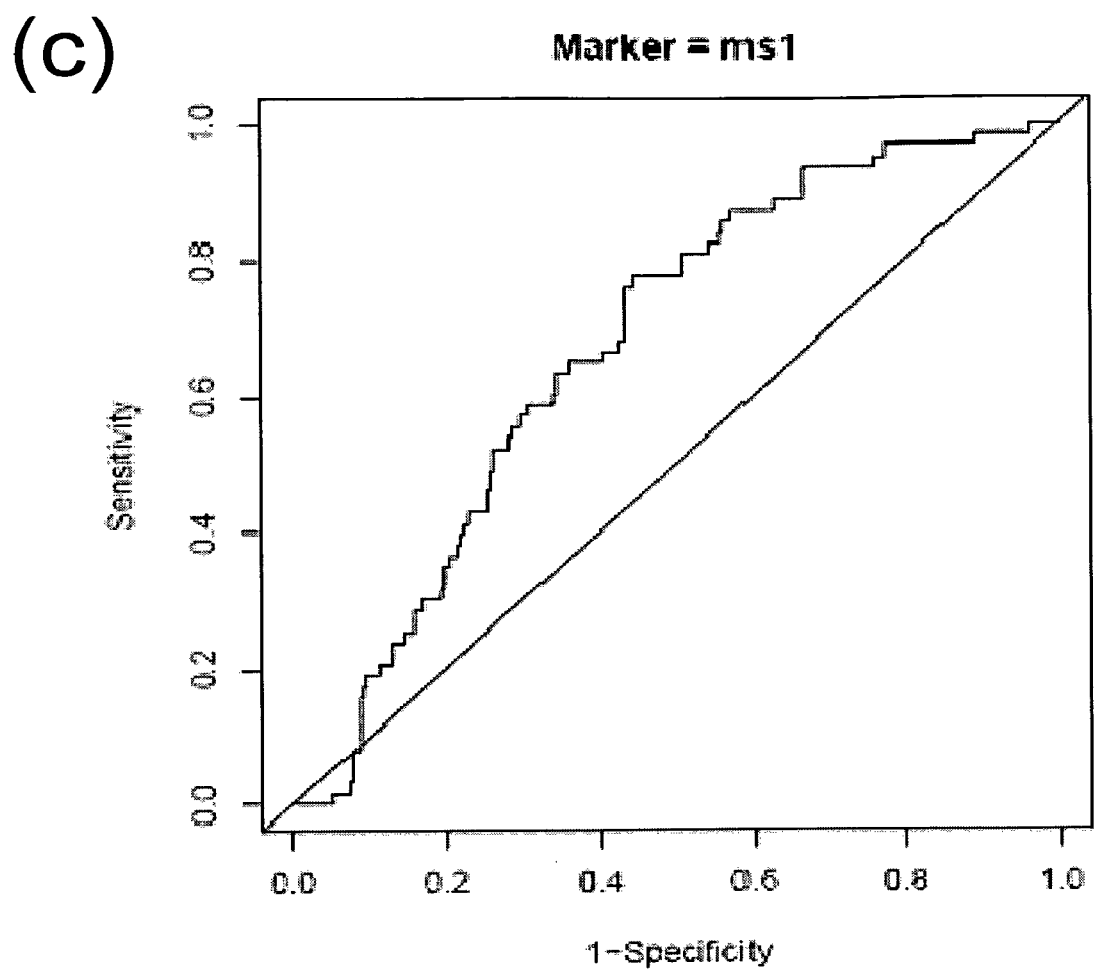
Figure 4:
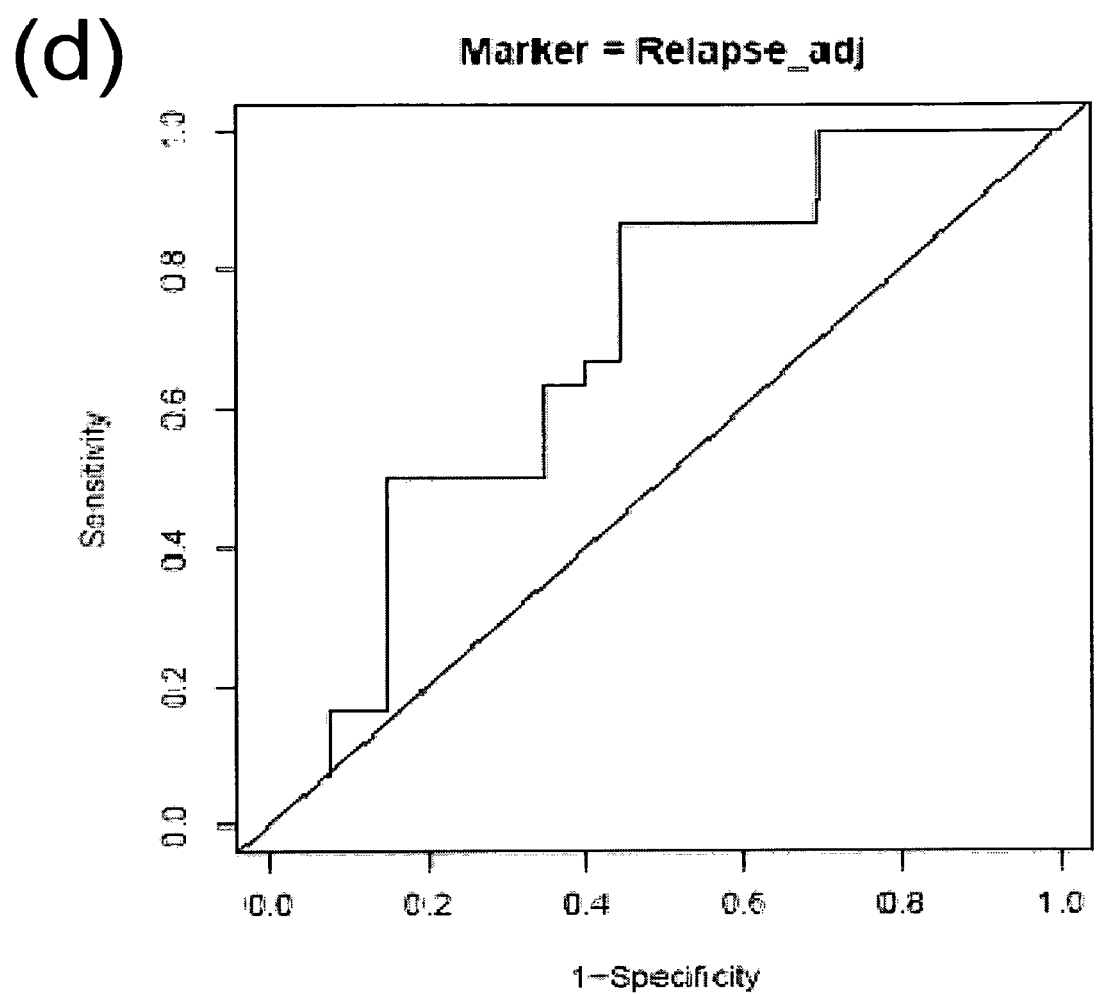
Figure 4:
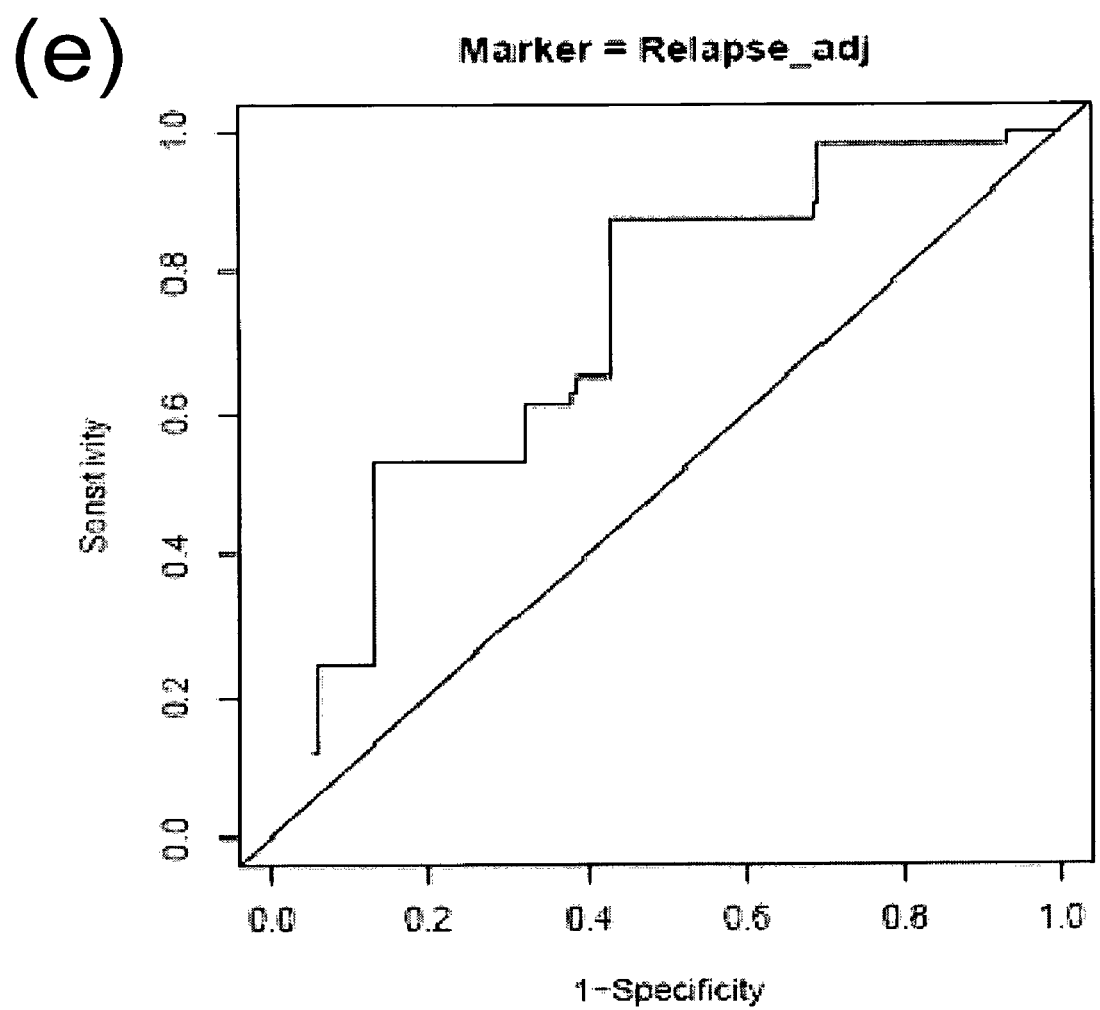
Figure 4:
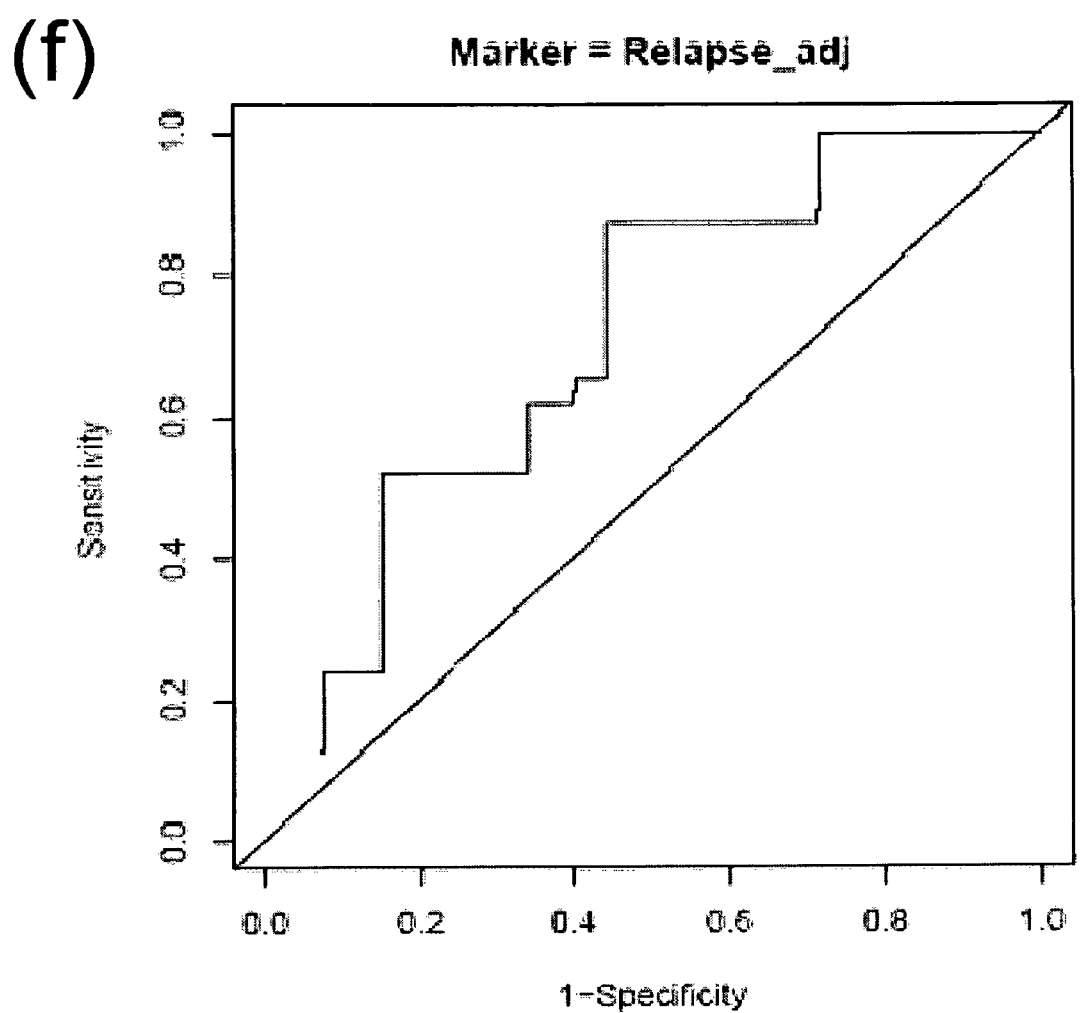

FIG. 4 shows Receiver operating characteristic (ROC) curves of the gene signature and of the online program Adjuvant! a) ROC curve for distant metastases within 5 years for the gene signature b) ROC curve for distant metastases within 10 years for the gene signature c) ROC curve for death within 10 years for the gene signature d) ROC curve for metastases within 5 years for Adjuvant! e) ROC curve for metastases within 10 years for Adjuvant! f) ROC curve for death within 10 years for Adjuvant! for untreated patients from Guy's Hospital FIG. 5 shows probability of distant metastasis within 5 years and 10 years vs. Metastasis Score (MS) from 280 Guy's untreated patients.

FIG. 6 is a comparison of probability of distant metastasis in 10 years from 14-gene signature vs, 10-year relapse probability from Adjuvant! for untreated patients from Guy's Hospital FIG. 7 shows Kaplan-Meier curves for distant-metastasis-free survival in University of Muenster patients.

FIG. 8 shows Kaplan-Meier curves of distant-metastasis-free survival in 3 MS groups (high, intermediate, low) for 205 treated patients from Guy's Hospital.

FIG. 9 shows Kaplan-Meier curves of distant-metastasis-free survival in 2 risk groups (high and low) determined by MS for 205 treated patients from Guy's Hospital.

FIG. 10 shows ROC curve of MS to predict distant metastasis in 5 years for Guy's treated samples, AUC=0.7 (0.57-0.87).

FIG. 11 shows time dependence of hazard ratios of high vs. low risk groups by MS in Guy's treated samples.

FIG. 12 shows Kaplan-Meier curves of distant-metastasis-free survival (DMFS) for three MS groups (high, intermediate and low) in 234 Japanese samples.

FIG. 13 shows Kaplan-Meier curves of distant-metastasis-free survival (DMFS) for two risk groups (high MS have high risk whereas intermediate and low MS have low risk) in 234 Japanese samples.

FIG. 14 shows ROC curve of MS to predict distant metastasis in 5 years for Japanese patients. AUC=0.73 (0.63-0.84).

FIG. 15 shows annualized hazard rate for MS groups and hazard ratio of high vs. low risk groups as a function of time.

DETAILED DESCRIPTION OF THE INVENTION

The present invention provides a multi-gene signature that can be used for predicting breast cancer metastasis, methods and reagents for the detection of the genes disclosed herein, and assays or kits that utilize such reagents. The breast cancer metastasis-associated genes disclosed herein are useful for diagnosing, screening for, and evaluating probability of distant metastasis of ER-positive tumors in breast cancer patients.

Expression profiling of the 14 genes of the molecular signature disclosed in Table 2 allows for prognosis of distant metastasis to be readily inferred. The information provided in Table 2 includes a reference sequence (RefSeq), obtained from the National Center for Biotechnology Information (NCBI) of the National Institutes of Health/National Library of Medicine, which identifies one variant transcript sequence of each described gene. Based on the sequence of the variant, reagents may be designed to detect all variants of each gene of the 14-gene signature. Table 3 provides exemplary primer sets that can be used to detect each gene of the 14-gene signature in a manner such that all variants of each gene are amplified. Thus, the present invention provides for expression profiling of all known transcript variants of all genes disclosed herein.

Also shown in Table 2 is the reference that publishes the nucleotide sequence of each RefSeq. These references are all herein incorporated by reference in their entirety. Also in Table 2 is a description of each gene. Both references and descriptions were provided by NCBI.

The CENPA gene is identified by reference sequence NM_001809 and disclosed in Black, B. E., Foltz, D. R., et al., 2004, *Nature* 430(6999):578-582. Said reference sequence and reference are herein incorporated by reference in their entirety.

The PKMYT1 gene, identified by reference sequence NM_004203, and disclosed in Bryan, B. A., Dyson, O. F. et al., 2006, *J. Gen. Virol.* 87 (PT 3), 519-529. Said reference sequence and reference are herein incorporated by reference in their entirety.

The MELK gene, identified by reference sequence NM_014791, and disclosed in Beullens, M., Vancauwenbergh, S. et al., 2005, *J. Biol. Chem.* 280 (48), 40003-40011. Said reference sequence and reference are herein incorporated by reference in their entirety.

The MYBL2 gene, identified by reference sequence NM_002466, and disclosed in Bryan, B. A., Dyson, O. F. et al., 2006, *J. Gen. Virol.* 87 (PT 3), 519-529. Said reference sequence and reference are herein incorporated by reference in their entirety.

The BUB1 gene, identified by reference sequence NM_004366, and disclosed in Morrow, C. J., Tighe, A. et al., 2005, *J. Cell. Sci.* 118 (PT 16), 3639-3652. Said reference sequence and reference are herein incorporated by reference in their entirety.

The RACGAP1 gene, identified by reference sequence NM_013277, and disclosed in Niiya, F., Xie, X. et al., 2005, *J. Biol. Chem.* 280 (43), 36502-36509. Said reference sequence and reference are herein incorporated by reference in their entirety.

The TK1 gene, identified by reference sequence NM_003258, and disclosed in Karbownik, M., Brzezianska, E. et al., 2005, *Cancer Lett.* 225 (2), 267-273. Said reference sequence and reference are herein incorporated by reference in their entirety.

The UBE2S gene, identified by reference sequence NM_014501, and disclosed in Liu, Z., Diaz, L. A. et al., 1992, *J. Biol. Chem.* 267 (22), 15829-15835. Said reference sequence and reference are herein incorporated by reference in their entirety.

The DC13 gene, identified by reference sequence AF201935, and disclosed in Gu, Y., Peng, Y. et al., Direct Submission, Submitted Nov. 5, 1999, Chinese National Human Genome Center at Shanghai, 351 Guo Shoujing Road, Zhangjiang Hi-Tech Park, Pudong, Shanghai 201203, P. R. China. Said reference sequence and reference are herein incorporated by reference in their entirety.

The RFC4 gene, identified by reference sequence NM_002916, and disclosed in Gupte, R. S., Weng, Y. et al., 2005, Cell Cycle 4 (2), 323-329. Said reference sequence and reference are herein incorporated by reference in their entirety.

The PRR11 gene, identified by reference sequence NM_018304, and disclosed in Weinmann, A. S., Yan, P. S. et al., 2002, Genes Dev. 16 (2), 235-244. Said reference sequence and reference are herein incorporated by reference in their entirety.

The DIAPH3 gene, identified by reference sequence NM_030932, and disclosed in Katoh, M. and Katoh, M., 2004, Int. J. Mol. Med. 13 (3), 473-478. Said reference sequence and reference are herein incorporated by reference in their entirety.

The ORC6L gene, identified by reference sequence NM_014321, and disclosed in Sibani, S., Price, G. B. et al., 2005, Biochemistry 44 (21), 7885-7896. Said reference sequence and reference are herein incorporated by reference in their entirety.

The CCNB1 gene, identified by reference sequence NM_031966, and disclosed in Zhao, M., Kim, Y. T. et al., 2006, Exp Oncol 28 (1), 44-48. Said reference sequence and reference are herein incorporated by reference in their entirety.

The PPIG gene, identified by reference sequence NM_004792, and disclosed in Lin, C. L., Leu, S. et al., 2004, Biochem. Biophys. Res. Commun. 321 (3), 638-647. Said reference sequence and reference are herein incorporated by reference in their entirety.

The NUP214 gene, identified by reference sequence NM_005085, and disclosed in Graux, C., Cools, J. et al., 2004, Nat. Genet. 36 (10), 1084-1089. Said reference sequence and reference are herein incorporated by reference in their entirety.

The SLU7 gene, identified by reference sequence NM_006425, and disclosed in Shomron, N., Alberstein, M. et al., 2005, J. Cell. Sci. 118 (PT 6), 1151-1159. Said reference sequence and reference are herein incorporated by reference in their entirety.

Also shown in Table 2 is the value for the constant ai required for determining the metastasis score for each gene i, based on the expression profiling results obtained for that gene. The derivation of the metastasis score and its use, and methods of gene expression profiling and use of the data obtained therefrom, are described below.

Thus, the present invention provides 14 individual genes which together are prognostic for breast cancer metastasis, methods of determining expression levels of these genes in a test sample, methods of determining the probability of an individual of developing distant metastasis, and methods of using the disclosed genes to select a treatment strategy.

The present invention provides a unique combination of a 14 gene signature that were not previously known in the art. Accordingly, the present invention provides novel methods based on the genes disclosed herein, and also provides novel methods of using the known, but previously unassociated, genes in methods relating to breast cancer metastasis (e.g., for prognosis of breast cancer metastasis).

Those skilled in the art will readily recognize that nucleic acid molecules may be double-stranded molecules and that reference to a particular sequence of one strand refers, as well, to the corresponding site on a complementary strand. In defining a nucleotide sequence, reference to an adenine, a thymine (uridine), a cytosine, or a guanine at a particular site on one strand of a nucleic acid molecule also defines the thymine (uridine), adenine, guanine, or cytosine (respectively) at the corresponding site on a complementary strand of the nucleic acid molecule. Thus, reference may be made to either strand in order to refer to a particular nucleotide sequence. Probes and primers may be designed to hybridize to either strand and gene expression profiling methods disclosed herein may generally target either strand.

Tumor Tissue Source and RNA Extraction

In the present invention, target polynucleotide molecules are extracted from a sample taken from an individual afflicted with breast cancer. The sample may be collected in any clinically acceptable manner, but must be collected such that gene-specific polynucleotides (i.e., transcript RNA, or message) are preserved. The mRNA or nucleic acids so obtained from the sample may then be analyzed further. For example, pairs of oligonucleotides specific for a gene (e.g., the genes presented in Table 2) may be used to amplify the specific mRNA(s) in the sample. The amount of each message can then be determined, or profiled, and the correlation with a disease prognosis can be made. Alternatively, mRNA or nucleic acids derived therefrom (i.e. cDNA, amplified DNA or enriched RNA) may be labeled distinguishably from standard or control polynucleotide molecules, and both may be simultaneously or independently hybridized to a microarray comprising some or all of the markers or marker sets or subsets described above. Alternatively, mRNA or nucleic acids derived there from may be labeled with the same label as the standard or control polynucleotide molecules, wherein the intensity of hybridization of each at a particular probe is compared.

A sample may comprise any clinically relevant tissue sample, such as a formalin fixed paraffin embedded sample, frozen sample, tumor biopsy or fine needle aspirate, or a sample of bodily fluid containing ER-positive tumor cells such as blood, plasma, serum, lymph, ascitic or cystic fluid, urine, or nipple exudate.

Methods for preparing total and poly (A)+ RNA are well known and are described generally in Sambrook et al., MOLECULAR CLONING—A LABORATORY MANUAL (2ND ED.), Vols. 1-3, Cold Spring Harbor Laboratory, Cold Spring Harbor, N.Y. (1989)) and Ausubel et al., Current Protocols in Molecular Biology vol. 2, Current Protocols Publishing, New York (1994)). RNA may be isolated from ER-positive tumor cells by any procedures well-known in the art, generally involving lysis of the cells and denaturation of the proteins contained therein.

As an example of preparing RNA from tissue samples, RNA may also be isolated from formalin-fixed paraffin-embedded (FFPE) tissues using techniques well known in the art. Commercial kits for this purpose may be obtained, e.g., from Zymo Research, Ambion, Qiagen, or Stratagene. An exemplary method of isolating total RNA from FFPE tissue, according to the method of the Pinpoint Slide RNA Isolation System (Zymo Reasearch, Orange, Calif.) is as follows. Briefly, the solution obtained from the Zymo kit is applied over the selected FFPE tissue region of interest and allowed to dry. The embedded tissue is then removed from the slide and placed in a centrifuge tube with proteinase K. The tissue is incubated for several hours, then the cell lysate is centrifuged and and the supernatant transferred to another tube. RNA is extracted from the lysate by means of a guanidinium thiocynate/β mercaptoethanol solution, to which ethanol is added and mixed. Sample is applied to a spin column, and spun one minute. The column is washed with buffer containing ethanol and Tris/EDTA. DNase is added to the column, and incubated. RNA is eluted from the column by adding heated RNase-free water to the column and centrifuging. Pure total RNA is present in the eluate.

Additional steps may be employed to remove contaminating DNA, such as the addition of DNase to the spin column, described above. Cell lysis may be accomplished with a nonionic detergent, followed by micro-centrifugation to remove the nuclei and hence the bulk of the cellular DNA. In one embodiment, RNA is extracted from cells of the various types of interest by cell lysis in the presence of guanidinium thiocyanate, followed by CsC1 centrifugation to separate the RNA from DNA (Chirgwin et al., *Biochemistry* 18:5294-5299 (1979)). Poly(A)+ RNA is selected with oligo-dT cellulose (see Sambrook et al., MOLECULAR CLONING—A LABORATORY MANUAL (2ND ED.), Vols. 1-3, Cold Spring Harbor Laboratory, Cold Spring Harbor, N.Y. (1989). Alternatively, separation of RNA from DNA can be accomplished by organic extraction, for example, with hot phenol or phenol/chloroform/isoamyl alcohol.

If desired, RNase inhibitors may be added to the lysis buffer. Likewise, for certain cell types it may be desirable to add a protein denaturation/digestion step to the protocol.

For many applications, it is desirable to preferentially enrich mRNA with respect to other cellular RNAs extracted from cells, such as transfer RNA (tRNA) and ribosomal RNA (rRNA). Most mRNAs contain poly(A) tails at their 3' ends. This allows for enrichment by affinity chromatography; for example, using oligo(dT) or poly(U) coupled to a solid support, such as cellulose or Sephadex™ (see Ausubel et al., CURRENT PROTOCOLS IN MOLECULAR BIOLOGY, vol. 2, Current Protocols Publishing, New York (1994). After being bound in this manner, poly(A)+ mRNA is eluted from the affinity column using 2 mM EDTA/0.1% SDS.

The sample of RNA can comprise a plurality of different mRNA molecules, each mRNA molecule having a different nucleotide sequence. In a specific embodiment, the mRNA molecules of the RNA sample comprise mRNA corresponding to each of the fourteen genes disclosed herein. In a further specific embodiment, total RNA or mRNA from cells are used in the methods of the invention. The source of the RNA can be cells from any ER-positive tumor cell. In specific embodiments, the method of the invention is used with a sample containing total mRNA or total RNA from $1 \times 10^6$ cells or fewer.

Reagents for Measuring Gene Expression

The present invention provides nucleic acid molecules that can be used in gene expression profiling and in determining prognosis of breast cancer metastasis. Exemplary nucleic acid molecules that can be used as primers in gene expression profiling of the 14-gene signature described herein are shown in Table 3.

As indicated in Table 3:

Gene BUB1 is reverse-transcribed and amplified with SEQ ID NO: 1 as the Upper primer (5'), and SEQ ID NO: 2 as the Lower primer (3').

Gene CCNB1 is reverse-transcribed and amplified with SEQ ID NO: 3 as the Upper primer (5'), and SEQ ID NO: 4 as the Lower primer (3').

Gene CENPA is reverse-transcribed and amplified with SEQ ID NO: 5 as the Upper primer (5'), and SEQ ID NO: 6 as the Lower primer (3').

Gene DC13 is reverse-transcribed and amplified with SEQ ID NO: 7 as the Upper primer (5'), and SEQ ID NO: 8 as the Lower primer (3').

Gene DIAPH3 is reverse-transcribed and amplified with SEQ ID NO: 9 as the Upper primer (5'), and SEQ ID NO: 10 as the Lower primer (3').

Gene MELK is reverse-transcribed and amplified with SEQ ID NO: 11 as the Upper primer (5'), and SEQ ID NO: 12 as the Lower primer (3').

Gene MYBL2 is reverse-transcribed and amplified with SEQ ID NO: 13 as the Upper primer (5'), and SEQ ID NO: 14 as the Lower primer (3').

Gene NUP214 is reverse-transcribed and amplified with SEQ ID NO: 29 as the Upper primer (5'), and SEQ ID NO: 30 as the Lower primer (3').

Gene ORC6L is reverse-transcribed and amplified with SEQ ID NO: 15 as the Upper primer (5'), and SEQ ID NO: 16 as the Lower primer (3').

Gene PKMYT1 is reverse-transcribed and amplified with SEQ ID NO: 17 as the Upper primer (5'), and SEQ ID NO: 18 as the Lower primer (3').

Gene PPIG is reverse-transcribed and amplified with SEQ ID NO: 31 as the Upper primer (5'), and SEQ ID NO: 32 as the Lower primer (3').

Gene PRR11 is reverse-transcribed and amplified with SEQ ID NO: 19 as the Upper primer (5'), and SEQ ID NO: 20 as the Lower primer (3').

Gene RACGAP1 is reverse-transcribed and amplified with SEQ ID NO: 21 as the Upper primer (5'), and SEQ ID NO: 22 as the Lower primer (3').

Gene RFC4 is reverse-transcribed and amplified with SEQ ID NO: 23 as the Upper primer (5'), and SEQ ID NO: 24 as the Lower primer (3').

Gene SLU7 is reverse-transcribed and amplified with SEQ ID NO: 33 as the Upper primer (5'), and SEQ ID NO: 34 as the Lower primer (3').

Gene TK1 is reverse-transcribed and amplified with SEQ ID NO: 25 as the Upper primer (5'), and SEQ ID NO: 26 as the Lower primer (3').

Gene UBE2S is reverse-transcribed and amplified with SEQ ID NO: 27 as the Upper primer (5'), and SEQ ID NO: 28 as the Lower primer (3').

Based on the complete nucleotide sequence of each gene as shown in Table 2, one skilled in the art can readily design and synthesize additional primers and/or probes that can be used in the amplification and/or detection of the 14-gene signature described herein.

In a specific aspect of the present invention, the sequences disclosed in Table 3 can be used as gene expression profiling reagents. As used herein, a "gene expression profiling reagent" is a reagent that is specifically useful in the process of amplifying and/or detecting the nucleotide sequence of a specific target gene, whether that sequence is mRNA or cDNA, of the genes described herein. For example, the profiling reagent preferably can differentiate between different alternative gene nucleotide sequences, thereby allowing the identity and quantification of the nucleotide sequence to be determined. Typically, such a profiling reagent hybridizes to a target nucleic acid molecule by complementary base-pairing in a sequence-specific manner, and discriminates the target sequence from other nucleic acid sequences such as an art-known form in a test sample. An example of a detection reagent is a probe that hybridizes to a target nucleic acid containing a nucleotide sequence substantially complementary to one of the sequences provided in Table 3. In a preferred embodiment, such a probe can differentiate between nucleic acids of different genes. Another example of a detection reagent is a primer which acts as an initiation point of nucleotide extension along a complementary strand of a target polynucleotide, as in reverse transcription or PCR. The sequence information provided herein is also useful, for example, for designing primers to reverse transcribe and/or amplify (e.g., using PCR) any gene of the present invention.

In one preferred embodiment of the invention, a detection reagent is an isolated or synthetic DNA or RNA polynucleotide probe or primer or PNA oligomer, or a combination of DNA, RNA and/or PNA, that hybridizes to a segment of a target nucleic acid molecule corresponding to any of the genes disclosed in Table 2. A detection reagent in the form of a polynucleotide may optionally contain modified base analogs, intercalators or minor groove binders. Multiple detection reagents such as probes may be, for example, affixed to a solid support (e.g., arrays or beads) or supplied in solution (e.g., probe/primer sets for enzymatic reactions such as PCR, RT-PCR, TaqMan assays, or primer-extension reactions) to form an expression profiling kit.

A probe or primer typically is a substantially purified oligonucleotide or PNA oligomer. Such oligonucleotide typically comprises a region of complementary nucleotide sequence that hybridizes under stringent conditions to at least about 8, 10, 12, 16, 18, 20, 22, 25, 30, 40, 50, 55, 60, 65, 70, 80, 90, 100, 120 (or any other number in-between) or more consecutive nucleotides in a target nucleic acid molecule.

Other preferred primer and probe sequences can readily be determined using the nucleotide sequences of genes disclosed in Table 2. It will be apparent to one of skill in the art that such primers and probes are directly useful as reagents for expression profiling of the genes of the present invention, and can be incorporated into any kit/system format.

In order to produce a probe or primer specific for a target gene sequence, the gene/transcript sequence is typically examined using a computer algorithm which starts at the 5' or at the 3' end of the nucleotide sequence. Typical algorithms will then identify oligomers of defined length that are unique to the gene sequence, have a GC content within a range suitable for hybridization, lack predicted secondary structure that may interfere with hybridization, and/or possess other desired characteristics or that lack other undesired characteristics.

A primer or probe of the present invention is typically at least about 8 nucleotides in length. In one embodiment of the invention, a primer or a probe is at least about 10 nucleotides in length. In a preferred embodiment, a primer or a probe is at least about 12 nucleotides in length. In a more preferred embodiment, a primer or probe is at least about 16, 17, 18, 19, 20, 21, 22, 23, 24 or 25 nucleotides in length. While the maximal length of a probe can be as long as the target sequence to be detected, depending on the type of assay in which it is employed, it is typically less than about 50, 60, 65, or 70 nucleotides in length. In the case of a primer, it is typically less than about 30 nucleotides in length. In a specific preferred embodiment of the invention, a primer or a probe is within the length of about 18 and about 28 nucleotides. However, in other embodiments, such as nucleic acid arrays and other embodiments in which probes are affixed to a substrate, the probes can be longer, such as on the order of 30-70, 75, 80, 90, 100, or more nucleotides in length.

The present invention encompasses nucleic acid analogs that contain modified, synthetic, or non-naturally occurring nucleotides or structural elements or other alternative/modified nucleic acid chemistries known in the art. Such nucleic acid analogs are useful, for example, as detection reagents (e.g., primers/probes) for detecting one or more of the genes identified in Table 2. Furthermore, kits/systems (such as beads, arrays, etc.) that include these analogs are also encompassed by the present invention. For example, PNA oligomers that are based on the polymorphic sequences of the present invention are specifically contemplated. PNA oligomers are analogs of DNA in which the phosphate backbone is replaced with a peptide-like backbone (Lagriffoul et al., *Bioorganic & Medicinal Chemistry Letters* 4:1081-1082 [1994], Petersen et al., *Bioorganic & Medicinal Chemistry Letters* 6:793-796 [1996], Kumar et al., *Organic Letters* 3[9]:1269-1272 [2001], WO96/04000). PNA hybridizes to complementary RNA or DNA with higher affinity and specificity than conventional oligonucleotides and oligonucleotide analogs. The properties of PNA enable novel molecular biology and biochemistry applications unachievable with traditional oligonucleotides and peptides.

Additional examples of nucleic acid modifications that improve the binding properties and/or stability of a nucleic acid include the use of base analogs such as inosine, intercalators (U.S. Pat. No. 4,835,263) such as ethidium bromide and SYBR® Green, and the minor groove binders (U.S. Pat. No. 5,801,115). Thus, references herein to nucleic acid molecules, expression profiling reagents (e.g., probes and primers), and oligonucleotides/polynucleotides include PNA oligomers and other nucleic acid analogs. Other examples of nucleic acid analogs and alternative/modified nucleic acid chemistries known in the art are described in *Current Protocols in Nucleic Acid Chemistry*, John Wiley & Sons, New York (2002).

While the design of each allele-specific primer or probe depends on variables such as the precise composition of the nucleotide sequences in a target nucleic acid molecule and the length of the primer or probe, another factor in the use of primers and probes is the stringency of the conditions under which the hybridization between the probe or primer and the target sequence is performed. Higher stringency conditions utilize buffers with lower ionic strength and/or a higher reaction temperature, and tend to require a closer match between the probe/primer and target sequence in order to form a stable duplex. If the stringency is too high, however, hybridization may not occur at all. In contrast, lower stringency conditions utilize buffers with higher ionic strength and/or a lower reaction temperature, and permit the formation of stable duplexes with more mismatched bases between a probe/primer and a target sequence. By way of example but not limitation, exemplary conditions for high-stringency hybridization conditions using an allele-specific probe are as follows: prehybridization with a solution containing 5× standard saline phosphate EDTA (SSPE), 0.5% $NaDodSO_4$ (SDS) at 55° C., and incubating probe with target nucleic acid molecules in the same solution at the same temperature, followed by washing with a solution containing 2× SSPE, and 0.1% SDS at 55° C. or room temperature.

Moderate-stringency hybridization conditions may be used for primer extension reactions with a solution containing, e.g., about 50 mM KCl at about 46° C. Alternatively, the reaction may be carried out at an elevated temperature such as 60° C. In another embodiment, a moderately-stringent hybridization condition is suitable for oligonucleotide ligation assay (OLA) reactions, wherein two probes are ligated if they are completely complementary to the target sequence, and may utilize a solution of about 100 mM KCl at a temperature of 46° C.

In a hybridization-based assay, specific probes can be designed that hybridize to a segment of target DNA of one gene sequence but do not hybridize to sequences from other genes. Hybridization conditions should be sufficiently stringent that there is a significant detectable difference in hybridization intensity between genes, and preferably an essentially binary response, whereby a probe hybridizes to only one of the gene sequences or significantly more strongly to one gene sequence. While a probe may be designed to hybridize to a target sequence of a specific gene such that the target site aligns anywhere along the sequence of the probe, the probe is preferably designed to hybridize to a segment of the target sequence such that the gene sequence aligns with a central position of the probe (e.g., a position within the probe that is at least three nucleotides from either end of the probe). This design of probe generally achieves good discrimination in hybridization between different genes.

Oligonucleotide probes and primers may be prepared by methods well known in the art. Chemical synthetic methods include, but are not limited to, the phosphotriester method described by Narang et al., *Methods in Enzymology* 68:90 [1979]; the phosphodiester method described by Brown et al.,

*Methods in Enzymology* 68:109 [1979], the diethylphosphoamidate method described by Beaucage et al., *Tetrahedron Letters* 22:1859 [1981]; and the solid support method described in U.S. Pat. No. 4,458,066. In the case of an array, multiple probes can be immobilized on the same support for simultaneous analysis of multiple different gene sequences.

In one type of PCR-based assay, a gene-specific primer hybridizes to a region on a target nucleic acid molecule that overlaps a gene sequence and only primes amplification of the gene sequence to which the primer exhibits perfect complementarity (Gibbs, *Nucleic Acid Res.* 17:2427-2448 [1989]). Typically, the primer's 3'-most nucleotide is aligned with and complementary to the target nucleic acid molecule. This primer is used in conjunction with a second primer that hybridizes at a distal site. Amplification proceeds from the two primers, producing a detectable product that indicates which gene/transcript is present in the test sample. This PCR-based assay can be utilized as part of the TaqMan assay, described below.

The genes in the 14-gene signature described herein can be detected by any one of a variety of nucleic acid amplification methods, which are used to increase the copy numbers of a polynucleotide of interest in a nucleic acid sample. Such amplification methods are well known in the art, and they include but are not limited to, polymerase chain reaction (PCR) (U.S. Pat. Nos. 4,683,195 and 4,683,202; *PCR Technology: Principles and Applications for DNA Amplification*, ed. H. A. Erlich, Freeman Press, New York, N.Y. [1992]), ligase chain reaction (LCR) (Wu and Wallace, *Genomics* 4:560 [1989]; Landegren et al., *Science* 241:1077 [1988]), strand displacement amplification (SDA) (U.S. Pat. Nos. 5,270,184 and 5,422,252), transcription-mediated amplification (TMA) (U.S. Pat. No. 5,399,491), linked linear amplification (LLA) (U.S. Pat. No. 6,027,923), and the like, and isothermal amplification methods such as nucleic acid sequence based amplification (NASBA), and self-sustained sequence replication (Guatelli et al., *Proc. Natl. Acad. Sci. USA* 87: 1874 [1990]). Based on such methodologies, a person skilled in the art can readily design primers in any suitable regions 5' and 3' of the gene sequences of interest, so as to amplify the genes disclosed herein. Such primers may be used to reverse-transcribe and amplify DNA of any length, such that it contains the gene of interest in its sequence.

Generally, an amplified polynucleotide is at least about 16 nucleotides in length. More typically, an amplified polynucleotide is at least about 20 nucleotides in length. In a preferred embodiment of the invention, an amplified polynucleotide is at least about 30 nucleotides in length. In a more preferred embodiment of the invention, an amplified polynucleotide is at least about 32, 40, 45, 50, or 60 nucleotides in length. In yet another preferred embodiment of the invention, an amplified polynucleotide is at least about 100, 200, 300, 400, or 500 nucleotides in length. While the total length of an amplified polynucleotide of the invention can be as long as an exon, an intron or the entire gene, an amplified product is typically up to about 1,000 nucleotides in length (although certain amplification methods may generate amplified products greater than 1,000 nucleotides in length). More preferably, an amplified polynucleotide is not greater than about 150-250 nucleotides in length.

In an embodiment of the invention, a gene expression profiling reagent of the invention is labeled with a fluorogenic reporter dye that emits a detectable signal. While the preferred reporter dye is a fluorescent dye, any reporter dye that can be attached to a detection reagent such as an oligonucleotide probe or primer is suitable for use in the invention. Such dyes include, but are not limited to, Acridine, AMCA, BODIPY, Cascade Blue, Cy2, Cy3, Cy5, Cy7, Dabcyl, Edans, Eosin, Erythrosin, Fluorescein, 6-Fam, Tet, Joe, Hex, Oregon Green, Rhodamine, Rhodol Green, Tamra, Rox, and Texas Red.

In yet another embodiment of the invention, the detection reagent may be further labeled with a quencher dye such as Tamra, especially when the reagent is used as a self-quenching probe such as a TaqMan (U.S. Pat. Nos. 5,210,015 and 5,538,848) or Molecular Beacon probe (U.S. Pat. Nos. 5,118, 801 and 5,312,728), or other stemless or linear beacon probe (Livak et al., *PCR Method Appl.* 4:357-362 [1995]; Tyagi et al., *Nature Biotechnology* 14:303-308 [1996]; Nazarenko et al., *Nucl. Acids Res.* 25:2516-2521 [1997]; U.S. Pat. Nos. 5,866,336 and 6,117,635).

The detection reagents of the invention may also contain other labels, including but not limited to, biotin for streptavidin binding, hapten for antibody binding, and oligonucleotide for binding to another complementary oligonucleotide such as pairs of zipcodes.

Gene Expression Kits and Systems

A person skilled in the art will recognize that, based on the gene and sequence information disclosed herein, expression profiling reagents can be developed and used to assay any genes of the present invention individually or in combination, and such detection reagents can be readily incorporated into one of the established kit or system formats which are well known in the art. The terms "kits" and "systems," as used herein in the context of gene expression profiling reagents, are intended to refer to such things as combinations of multiple gene expression profiling reagents, or one or more gene expression profiling reagents in combination with one or more other types of elements or components (e.g., other types of biochemical reagents, containers, packages such as packaging intended for commercial sale, substrates to which gene expression profiling reagents are attached, electronic hardware components, etc.). Accordingly, the present invention further provides gene expression profiling kits and systems, including but not limited to, packaged probe and primer sets (e.g., TaqMan probe/primer sets), arrays/microarrays of nucleic acid molecules, and beads that contain one or more probes, primers, or other detection reagents for profiling one or more genes of the present invention. The kits/systems can optionally include various electronic hardware components; for example, arrays ("DNA chips") and microfluidic systems ("lab-on-a-chip" systems) provided by various manufacturers typically comprise hardware components. Other kits/systems (e.g., probe/primer sets) may not include electronic hardware components, but may be comprised of, for example, one or more gene expression profiling reagents (along with, optionally, other biochemical reagents) packaged in one or more containers.

In some embodiments, a gene expression profiling kit typically contains one or more detection reagents and other components (e.g., a buffer, enzymes such as reverse transcriptase, DNA polymerases or ligases, reverse transcription and chain extension nucleotides such as deoxynucleotide triphosphates, and in the case of Sanger-type DNA sequencing reactions, chain terminating nucleotides, positive control sequences, negative control sequences, and the like) necessary to carry out an assay or reaction, such as reverse transcription, amplification and/or detection of a gene-containing nucleic acid molecule. A kit may further contain means for determining the amount of a target nucleic acid, and means for comparing the amount with a standard, and can comprise instructions for using the kit to detect the gene-containing nucleic acid molecule of interest. In one embodiment of the present invention, kits are provided which contain the necessary reagents to carry out one or more assays to profile the expression of one or more of the genes disclosed herein. In a preferred embodiment of the present invention, gene expression profiling kits/systems are in the form of nucleic acid arrays, or compartmentalized kits, including microfluidic/lab-on-a-chip systems.

Gene expression profiling kits/systems may contain, for example, one or more probes, or pairs of probes, that hybridize to a nucleic acid molecule at or near each target gene sequence position. Multiple pairs of gene-specific probes may be included in the kit/system to simultaneously assay large numbers of genes, at least one of which is a gene of the present invention. In some kits/systems, the gene-specific probes are immobilized to a substrate such as an array or bead. For example, the same substrate can comprise gene-specific probes for detecting at least 1 or substantially all of the genes shown in Table 2, or any other number in between.

The terms "arrays," "microarrays," and "DNA chips" are used herein interchangeably to refer to an array of distinct polynucleotides affixed to a substrate, such as glass, plastic, paper, nylon or other type of membrane, filter, chip, or any other suitable solid support. The polynucleotides can be synthesized directly on the substrate, or synthesized separate from the substrate and then affixed to the substrate. In one embodiment, the microarray is prepared and used according to the methods described in U.S. Pat. No. 5,837,832 (Chee et al.), PCT application WO95/11995 (Chee et al.), Lockhart, D. J. et al. (*Nat. Biotech.* 14:1675-1680 [1996]) and Schena, M. et al. (*Proc. Natl. Acad. Sci.* 93:10614-10619 [1996]), all of which are incorporated herein in their entirety by reference. In other embodiments, such arrays are produced by the methods described by Brown et al., U.S. Pat. No. 5,807,522.

Nucleic acid arrays are reviewed in the following references: Zammatteo et al., "New chips for molecular biology and diagnostics," *Biotechnol. Annu. Rev.* 8:85-101 (2002); Sosnowski et al., "Active microelectronic array system for DNA hybridization, genotyping and pharmacogenomic applications," *Psychiatr. Genet.* 12(4)-:181-92 (December 2002); Heller, "DNA microarray technology: devices, systems, and applications," *Annu. Rev. Biomed. Eng.* 4:129-53 (2002); Epub Mar. 22 2002; Kolchinsky et al., "Analysis of SNPs and other genomic variations using gel-based chips," *Hum. Mutat.* 19(4):343-60 (April 2002); and McGall et al., "High-density genechip oligonucleotide probe arrays," *Adv. Biochem. Eng. Biotechnol.* 77:21-42 (2002).

Any number of probes, such as gene-specific probes, may be implemented in an array, and each probe or pair of probes can hybridize to a different gene sequence position. In the case of polynucleotide probes, they can be synthesized at designated areas (or synthesized separately and then affixed to designated areas) on a substrate using a light-directed chemical process. Each DNA chip can contain, for example, thousands to millions of individual synthetic polynucleotide probes arranged in a grid-like pattern and miniaturized (e.g., to the size of a dime). Preferably, probes are attached to a solid support in an ordered, addressable array.

A microarray can be composed of a large number of unique, single-stranded polynucleotides, usually either synthetic antisense polynucleotides or fragments of cDNAs, fixed to a solid support. Typical polynucleotides are preferably about 6-60 nucleotides in length, more preferably about 15-30 nucleotides in length, and most preferably about 18-25 nucleotides in length. For certain types of microarrays or other detection kits/systems, it may be preferable to use oligonucleotides that are only about 7-20 nucleotides in length. In other types of arrays, such as arrays used in conjunction with chemiluminescent detection technology, preferred probe lengths can be, for example, about 15-80 nucleotides in length, preferably about 50-70 nucleotides in length, more preferably about 55-65 nucleotides in length, and most preferably about 60 nucleotides in length. The microarray or detection kit can contain polynucleotides that cover the known 5' or 3' sequence of a gene/transcript, sequential polynucleotides that cover the full-length sequence of a gene/transcript; or unique polynucleotides selected from particular areas along the length of a target gene/transcript sequence, particularly areas corresponding to one or more genes disclosed in Table 2. Polynucleotides used in the microarray or detection kit can be specific to a gene or genes of interest (e.g., specific to a particular signature sequence within a target gene sequence, or specific to a particular gene sequence at multiple different sequence sites), or specific to a polymorphic gene/transcript or genes/transcripts of interest.

Hybridization assays based on polynucleotide arrays rely on the differences in hybridization stability of the probes to perfectly matched and mismatched target sequences.

In other embodiments, the arrays are used in conjunction with chemiluminescent detection technology. The following patents and patent applications, which are all herein incorporated by reference in their entirety, provide additional information pertaining to chemiluminescent detection: U.S. patent application Ser. Nos. 10/620332 and 10/620333 describe chemiluminescent approaches for microarray detection; U.S. Pat. Nos. 6,124,478, 6,107,024, 5,994,073, 5,981,768, 5,871,938, 5,843,681, 5,800,999, and 5,773,628 describe methods and compositions of dioxetane for performing chemiluminescent detection; and U.S. published application US2002/0110828 discloses methods and compositions for microarray controls.

In one embodiment of the invention, a nucleic acid array can comprise an array of probes of about 15-25 nucleotides in length. In further embodiments, a nucleic acid array can comprise any number of probes, in which at least one probe is capable of detecting one or more genes disclosed in Table 2, and/or at least one probe comprises a fragment of one of the gene sequences selected from the group consisting of those disclosed in Table 2, and sequences complementary thereto, said fragment comprising at least about 8 consecutive nucleotides, preferably 10, 12, 15, 16, 18, 20, more preferably 22, 25, 30, 40, 47, 50, 55, 60, 65, 70, 80, 90, 100, or more consecutive nucleotides (or any other number in-between) and containing (or being complementary to) a sequence of a gene disclosed in Table 2. In some embodiments, the nucleotide complementary to the gene site is within 5, 4, 3, 2, or 1 nucleotide from the center of the probe, more preferably at the center of said probe.

A polynucleotide probe can be synthesized on the surface of the substrate by using a chemical coupling procedure and an ink jet application apparatus, as described in PCT application WO95/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536, 6144 or more polynucleotides, or any other number which lends itself to the efficient use of commercially available instrumentation.

Using such arrays or other kits/systems, the present invention provides methods of identifying and profiling expression of the genes disclosed herein in a test sample. Such methods typically involve incubating a test sample of nucleic acids with an array comprising one or more probes corresponding to at least one gene sequence position of the present invention, and assaying for binding of a nucleic acid from the test sample with one or more of the probes. Conditions for incubating a gene expression profiling reagent (or a kit/system that employs one or more such gene expression profiling reagents) with a test sample vary. Incubation conditions depend on factors such as the format employed in the assay, the profiling methods employed, and the type and nature of the profiling reagents used in the assay. One skilled in the art will recognize that any one of the commonly available hybridization, amplification and array assay formats can readily be adapted to detect the genes disclosed herein.

A gene expression profiling kit/system of the present invention may include components that are used to prepare nucleic acids from a test sample for the subsequent reverse transcription, RNA enrichment, amplification and/or detection of a gene sequence-containing nucleic acid molecule. Such sample preparation components can be used to produce nucleic acid extracts (including DNA, cDNA and/or RNA) from any tumor tissue source, including but not limited to, fresh tumor biopsy, frozen or foramalin-fixed paraffin embedded (FFPE) tissue specimens, or tumors collected and preserved by any method. The test samples used in the above-described methods will vary based on such factors as the assay format, nature of the profiling method, and the specific tissues, cells or extracts used as the test sample to be assayed. Methods of preparing nucleic acids are well known in the art and can be readily adapted to obtain a sample that is compatible with the system utilized. Automated sample preparation systems for extracting nucleic acids from a test sample are commercially available, and examples are Qiagen's BioRobot 9600, Applied Biosystems' PRISM 6700, and Roche Molecular Systems' COBAS AmpliPrep System.

Another form of kit contemplated by the present invention is a compartmentalized kit. A compartmentalized kit includes any kit in which reagents are contained in separate containers. Such containers include, for example, small glass containers, plastic containers, strips of plastic, glass or paper, or arraying material such as silica. Such containers allow one to efficiently transfer reagents from one compartment to another compartment such that the test samples and reagents are not cross-contaminated, or from one container to another vessel not included in the kit, and the agents or solutions of each container can be added in a quantitative fashion from one compartment to another or to another vessel. Such containers may include, for example, one or more containers which will accept the test sample, one or more containers which contain at least one probe or other gene expression profiling reagent for profiling the expression of one or more genes of the present invention, one or more containers which contain wash reagents (such as phosphate buffered saline, Tris-buffers, etc.), and one or more containers which contain the reagents used to reveal the presence of the bound probe or other gene expression profiling reagents. The kit can optionally further comprise compartments and/or reagents for, for example, reverse transcription, RNA enrichment, nucleic acid amplification or other enzymatic reactions such as primer extension reactions, hybridization, ligation, electrophoresis (preferably capillary electrophoresis), mass spectrometry, and/or laser-induced fluorescent detection. The kit may also include instructions for using the kit. Exemplary compartmentalized kits include microfluidic devices known in the art (see, e.g., Weigl et al., "Lab-on-a-chip for drug development," *Adv. Drug Deliv. Rev.* 24, 55[3]:349-77 [February 2003]). In such microfluidic devices, the containers may be referred to as, for example, microfluidic "compartments," "chambers," or "channels."

Uses of Gene Expression Profiling Reagents

The nucleic acid molecules in Table 3 of the present invention have a variety of uses, especially in the prognosis of breast cancer metastasis. For example, the nucleic acid molecules are useful as amplification primers or hybridization probes, such as for expression profiling using messenger RNA, transcript RNA, cDNA, genomic DNA, amplified DNA or other nucleic acid molecules, and for isolating full-length cDNA and genomic clones encoding the genes disclosed in Table 2 as well as their orthologs.

A probe can hybridize to any nucleotide sequence along the entire length of a nucleic acid molecule. Preferably, a probe of the present invention hybridizes to a region of a target sequence that encompasses a gene sequence of the genes indicated in Table 2. More preferably, a probe hybridizes to a gene-containing target sequence in a sequence-specific manner such that it distinguishes the target sequence from other nucleotide sequences which vary from the target sequence. Such a probe is particularly useful for detecting the presence of a gene-containing nucleic acid in a test sample.

Thus, the nucleic acid molecules of the invention can be used as hybridization probes, reverse transcription and/or amplification primers to detect and profile the expression levels of the genes disclosed herein, thereby determining the probability of whether an individual with breast cancer and said expression profile is at risk for distant metastasis. Expression profiling of disclosed genes provides a prognostic tool for a distant metastasis.

Generation of the Metastasis Score

Expression levels of the fourteen genes disclosed in Table 2 can be used to derive a metastasis score (MS) predictive of metastasis risk. Expression levels may be calculated by the $\Delta(\Delta C_T)$ method, where Ct=the threshold cycle for target amplification; i.e., the cycle number in PCR at which time exponential amplification of target begins. (K J Livak and T D Schmittgen, 2001, *Methods* 25:402-408). The level of mRNA of each of the 14 profiled genes may be defined as:

$$\Delta(\Delta Ct) = (Ct_{GOI} - Ct_{EC})_{test\,RNA} - (Ct_{GOI} - Ct_{EC})_{ref\,RNA}$$

where GOI=gene of interest (each of 14 signature genes), test RNA=RNA obtained from the patient sample, ref RNA=a calibrator reference RNA, and EC=an endogenous control. The expression level of each signature gene may be first normalized to the three endogenous control genes, listed in Table 2 (EC). A Ct representing the average of the Cts obtained from amplification of the three endogenous controls ($Ct_{EC}$) can be used to minimize the risk of normalization bias that would occur if only one control gene were used. (T. Suzuki, P J Higgins et al., 2000, *Biotechniques* 29:332-337). Primers that may preferably be used to amplify the endogenous control genes are listed in Table 3; but primers possible for amplifying these endogenous controls are not limited to these disclosed oligonucleotides. The adjusted expression level of the gene of interest may be further normalized to a calibrator reference RNA pool, ref RNA (universal human reference RNA, Stratagene, La Jolla, Calif.). This can be used to standardize expression results obtained from various machines.

The $\Delta(\Delta Ct)$ value, obtained in gene expression profiling for each of the 14 signature genes, may be used in the following formula to generate a metastasis score (MS):

$$MS = a0 + \sum_{i=1}^{M} ai * Gi$$

in which Gi represents the expression level of each gene (i) of the 14-gene prognostic signature. The value of Gi is the $\Delta(\Delta Ct)$ obtained in expression profiling described above. The constant ai for each gene i is provided in Table 2. The constant a0=0.022; this centers the MS so that its median value is zero. M is the number of genes in the component list; in this case fourteen. Thus, the MS is a measure of the summation of expression levels for the 14 genes disclosed in Table 2, each multiplied by a particular constant ai, also in Table 2, and finally this summation is added to the centering constant 0.022 to derive the MS.

Alternatively, the $\Delta(\Delta Ct)$ value, obtained in gene expression profiling for each of the 14 signature genes, may be used in the following formula to generate a metastasis score (MS):

$$MS = a0 + b * \sum_{i=1}^{M} ai * Gi$$

in which Gi represents the standardized expression level of each gene (i) of the 14-gene prognostic signature. The value of Gi is obtained by subtracting the mean gene expression from the original expression level measured in $\Delta(\Delta Ct)$ obtained in expression profiling described above and then divided by the standard deviation of the gene expression in the training set. The constant ai for each gene i is provided in Table 2. The constant b was −0.251. It was from a univariate Cox model with the principal component as a predictor, to get the correct sign and scaling. The constant a0=0.022; this centers the MS so that its median value is zero. M is the number of genes in the component list; in this case fourteen. Thus, the MS is a measure of the summation of expression levels for the 14 genes disclosed in Table 2, each multiplied by a particular constant ai, also in Table 2. This summation is multiplied by a constant b and the centering constant 0.022 is then added to derive the MS.

Any new sample may be evaluated by generating this metastasis score from the 14-gene expression profiling data for that patient, and from this score the probability of distant metastasis for the patient can be determined.

Note that the MS score can be simply a sum of the values of $\Delta(\Delta Ct)$ as described above, in which case the formula of the MS is simplified by substituting the value of a0 with zero, and the constant ai is one.

Note that the MS score can also be simply a sum of the values of $\Delta(\Delta Ct)$ as described above, then multiplied by the constant −0.04778 for correct sign and scaling such that distant metastasis risk increases with increase of MS. Finally the constant 0.8657 is added so that the mean of MS is zero. MS score derived in this alternative way will have equal weighting of all fourteen genes. The risk of distant metastasis would increase as MS increase. The two different MS scores described here have very high correlation with Pearson correlation coefficient greater than 0.999.

Generation of Distant Metastasis Probability from MS

The probability of distant metastasis for any individual patient can be calculated from the MS at variable time points, using the Weibull distribution as the baseline survival function.

The metastasis score (MS) obtained above, from expression profiling of the 14-gene signature, was converted into the probability of distant metastasis by means of the Cox proportional hazard model. Because the Cox model does not specify the baseline hazard function, the hazard and survivor functions were first constructed through parametric regression models. In the parametric regression models, distant metastasis-free survival time was the outcome, and the metastasis score (MS) was the independent variable input. The event time was assumed to have a Weibull distribution; its two parameters were estimated using the survival data from which the MS was derived. To calculate the probability of distant metastasis within a certain time for a patient, the MS value is simply substituted into the formula for the survivor function.

Clinical Application of the MS Score in Risk Determination

One way of using the MS score in determining the risk for metastasis is to generate one or more MS Threshold, also known as MS "cut point". Such MS Threshold can be used as a benchmark when compared to the MS score of a breast cancer patient so as to determine whether such patient has either an increased or decreased risk. MS Threshold can be determined by different methods and are different for different definition of Metastasis Score. For MS defined in Equation 1 that was used in Examples 1, 2 and 3, MS Threshold was determined from hazard ratios of high-risk vs. low-risk groups. Kaplan-Meier (KM) curves for distant metastasis-free survival are generated for the high- and low-risk patient groups defined by MS cut points. The choice of median MS as cut point is based upon the calculation of the hazard ratios of the high vs. low-risk groups using different cut points from ten percentile of MS to ninety percentile of MS. The median cut point can be defined as the point where there are an equal number of individuals in the high and low-risk groups, and is found to produce near the highest hazard ratio in the training samples as described in Example 1. Hazard ratios (HR) and 95% confidence intervals (CI) using the cut point of median MS can be calculated and reported. Log rank tests are performed, and the hazard ratios are calculated for different cut points. The accuracy and value of the 14-gene signature in predicting distant metastasis at five years can be assessed by various means. (X H Zhou, N. Obuchowski et al., eds., 2002, *Statistical Methods in Diagnostic Medicine*, Wiley-Interscience, New York). For MS defined in Equation 2 that was used in Example 4 and 5, MS Threshold was determined from sensitivity and specificity of MS to predict distant metastasis in 5 year in samples from Guy's Hospital described in Example 2. Two MS cut points are chosen as such the sensitivity of MS to predict distant metastasis in 5 years is over 90% if the first cut point is used. The second cut point is chosen such that the sensitivity and specificity of MS to predict distant metastasis in 5 years will be both at 70%. For MS defined in Equation 2, the first MS Threshold is −0.1186 and the second MS Threshold is 0.3019. With two MS cut points, there are high, intermediate and low MS groups. In treated samples from Guy's Hospital and treated samples from Aichi Cancer Center in Japan, the high MS group is

EXAMPLES

The following examples are offered to illustrate, but not to limit the claimed invention.

Example One

The mRNA Expression Levels of a 14-Gene Prognostic Signature Predict Risk for Distant Metastasis in 142 Lymph Node-Negative, ER-Positive Breast Cancer Patients The following example illustrates how a 14-gene prognostic signature was identified and how it can be used in determining prognosis for distant metastasis in breast cancer patients, even in routine clinical laboratory testing. A clinician can perform mRNA expression profiling on the 14 genes described herein, using RNA obtained from a number of means such as biopsy, FFPE, frozen tissues, etc., and then insert the expression data into an algorithm provided herein to determine a prognostic metastasis score.

FFPE tissue sections obtained from node-negative, ER-positive breast cancer patients were used in the example described below. An initial set of 200 genes were analyzed to derive the final 14-gene signature. Included as candidate genes for this signature were genes previously reported in the literature. Also in this example, the extent of overlap of this signature with routinely used prognostic factors and tools was determined.

Tumors from node-negative, ER-positive patients were selected for this study because prognostic information for node-negative patients would be of great value in guiding treatment strategies. Also, microarray studies indicate that this tumor subset is clinically distinct from other types of breast cancer tumors. (T. Sorlie, C M Perou et al., 2001, *Proc Natl Acad Sci USA* 98:10869-10874; C. Sotiriou, S Y Neo et al., 2003, *Proc Natl Acad Sci USA* 100: 10393-10398). Genes were chosen for expression profiling from the gene signatures reported by H. Dai (H. Dai, L J van't Veer et al., 2005, *Cancer Res* 15:4059-4066), L J van't Veer (L J van't Veer, H. Dai et al., 2002, *Nature* 415:530-536), and S P Paik (S P Paik, S. Shak et al., 2004, *N Engl J Med* 351:2817-2826), in FFPE sections to determine the robustness of these genes and the extent to which routinely collected and stored clinical samples could be used for prognosis of metastasis. From the gene expression data a metastasis score was developed to estimate distant metastasis probability in individual patients for any timeframe.

Patients and Samples

A total of 142 node-negative, ER-positive patients with early stage breast cancer were selected, all from patients untreated with systemic adjuvant therapy (Training samples in Table 1). By limiting the study to a subset of breast cancer cases, a molecular signature was identified with a more compelling association with metastasis, more robust across different sample sets, and comprising a smaller number of genes so as to better facilitate translation to routine clinical practice. The mean age of the patients was approximately 62 years (ranging from 31-89 years).

A highly-characterized breast tumor sample set served as the source of samples for this study; the set accrued from 1975 to 1986 at the California Pacific Medical Center (CPMC). The inclusion criteria for the primary study included samples from tumors from patients who were lymph-node negative, had received no systemic therapy, and received follow-up care for eight years.

Samples were approved for use in this study by the respective institutional medical ethics committees. Patients providing samples were classified as ER-positive based on a measurement of the expression level of the ESR1 gene. Expression level of the ESR1 gene correlates well with an individual's ER status. (M. Cronin, M. Pho et al. 2004, *Am J Pathol* 164(1):35-42; J M Knowlden, J M Gee et al., 1997, *Clin Cancer Res* 3:2165-2172).

Distant metastasis-free survival was chosen as the primary endpoint because it is most directly linked to cancer-related death. A secondary endpoint was overall survival.

Sample Processing

Four 10 μm sections from each paraffin block were used for RNA extraction. The tumor regions were removed based on a guide slide where the cancer cell areas have been marked by a pathologist, and the RNA extracted using Pinpoint Slide RNA Isolation System II (Zymo Research, Orange Calif.).

The yields of total RNA varied between samples. In order to increase the amount of RNA available for analysis, a T7 RNA polymerase linear amplification method was performed on the extracted RNA. RNA isolated from FFPE samples was subjected to T7-based RNA amplification using the MessageAmpII aRNA amplification kit (Ambion, Austin, Tex.).

To assess the consistency of gene expression before and after RNA amplification, a number of experiments were conducted on various genes in different samples. Amplification was first performed on RNA from 67 FFPE samples that were not a part of this study, using 0.1-100 ng of total RNA. Profiling of 20 genes was performed using the resultant enriched RNA and the original, unenriched RNA. These comparisons revealed that the fold enrichment varied from gene to gene; however, the relative expression level was consistent before and after RNA amplification in all 20 genes for 67 samples.

RNA for this study was enriched by amplification with the MessageAmpli aRNA amplification kit, as described above. Total RNA was quantified using spectrophotometric measurements ($OD_{260}$).

Gene Expression Profiling

Based on a survey of the published literature and results of microarray-based gene expression profiling experiments, 200 candidate genes were initially selected for analysis in order to determine the optimal prognostic signature. This set included genes from the 70-gene prognosis panel described by van't Veer et al (U van't Veer, H. Dai et al., 2002, *Nature* 415:530-536), 104 genes analyzed by Dai et al. (H. Dai, L J van't Veer et al., 2005, *Cancer Res* 15:4059-4066), the 16-gene panel comprising the signature for response to Tamoxifen treatment reported by Paik et al. (S P Paik, S. Shak et al., 2004, *N Engl J Med* 351:2817-2826), and 24 ER-related genes as reported by West et al. (M. West, C. Blanchette et al., 2001, *Proc Natl Acad Sci USA* 98:11462-11467).

Additional genes were selected as endogenous controls (EC) for normalizing expression data, according to the method described in J. Vandesompele, K. De Preter et al., *Genome Biol* 3(7): Research 0034.1-0034.11 (Epub 2002). Endogenous controls are also called "housekeeping genes" herein. Six endogenous control genes were tested for the stability of their expression levels in 150 samples of frozen breast cancer tumors. Expression data were analyzed using the geNorm program of Vandesompele et al., in which an M value was determined as a measurement of the stability of a gene's expression level. (J. Vandesompele, K. De Preter et al., Genome Biol 3(7): Research 0034.1-0034.11, Epub 2002). The lower the M value, the more stable the gene. Results are shown in Table 7. The M values indicated that PPIG, SLU7 and NUP214 were the most stable endogenous control genes in this sample set, with the least variation in gene expression across samples tested. The stability of these three genes was validated on 138 breast cancer tumor FFPE samples. The results are shown in Table 8.

The expression levels of the selected 200 genes, together with the three EC genes, were profiled in 142 RNA samples. For gene expression profiling, relative quantification by means of one-step reverse-transcription polymerase chain reaction (RT-PCR) was performed. Quantification was "relative" in that the expression of the target gene was evaluated relative to the expression of a set of reference, stably expressed control genes. SYBR® Green intercalating dye (Stratagene, La Jolla, Calif.) was used to visualize amplification product during real-time PCR. Briefly, the reaction mix allowed for reverse transcription of extracted sample RNA into cDNA. This cDNA was then PCR amplified in the same reaction tube, according to the cycling parameters described below. PCR conditions were designed so as to allow the primers disclosed in Table 3, upper and lower, to hybridize 5' and 3', respectively, of target sequences of the genes of interest, followed by extension from these primers to create amplification product in repetitive cycles of hybridization and extension. PCR was conducted in the presence of SYBR® Green, a dye which intercalates into double-stranded DNA, to allow for visualization of amplification product. RT-PCR was conducted on the Applied Biosystems Prism® 7900HT Sequence Detection System (Applied Biosystems, Foster City, Calif.), which detected the amount of amplification product present at periodic cycles throughout PCR, using amount of intercalated SYBR® Green as an indirect measure of product. (The fluorescent intensity of SYBR® Green is enhanced over 100-fold in binding to DNA.) PCR primers were designed so as to amplify all known splice-variants of each gene, and so that the size of all PCR products would be shorter than 150 base pairs in length, to accommodate the degraded, relatively shorter-length RNA expected to be found in FFPE samples. Primers used in the amplification of the 14 genes in the molecular signature described herein and three endogenous control genes are listed in Table 3. RT-PCR amplifications were performed in duplicate, in 384-well amplification plates. Each well contained a 15 ul reaction mix. The cycle profile consisted of: two minutes at 50° C., one minute at 95° C., 30 minutes at 60° C., followed by 45 cycles of 15 seconds at 95° C. and 30 seconds at 60° C., and ending with an amplification product dissociation analysis. The PCR components were essentially as described in L. Rogge, E. Bianchi et al., 2000, *Nat Genet* 25:96-101.

The relative changes in gene expression were determined by quantitative PCR. Expression levels were calculated by the $\Delta(\Delta C_t)$ method, where Ct=the threshold cycle for target amplification; i.e., the cycle number in PCR at which time exponentional amplification of target begins. (K J Livak and T D Schmittgen, 2001, *Methods* 25:402-408). The relative level of mRNA of a gene of interest was defined as:

$$\Delta(\Delta Ct) = (Ct_{GOI} - Ct_{EC})_{test RNA} - (Ct_{GOI} - Ct_{EC})_{ref RNA}$$

where GOI=gene of interest, test RNA=sample RNA, ref RNA=calibrator reference RNA, and EC=endogenous control. The expression level of every gene of interest was first normalized to the three endogenous control genes. A Ct representing the average of the three endogenous controls ($Ct_{EC}$) was used to minimize the risk of normalization bias that would occur if only one control gene was used. (T. Suzuki, P J Higgins et al., 2000, *Biotechniques* 29:332-337). Primers used to amplify the endogenous controls are listed in Table 3. The adjusted expression level of the gene of interest was further normalized to a calibrator reference RNA pool, ref RNA (universal human reference RNA, Stratagene, La Jolla, Calif.). This was used in order to standardize expression results obtained from various machines. The $\Delta(\Delta Ct)$ values obtained in expression profiling experiments of 200 genes were used in the statistical analysis described below to determine the 14-gene prognostic signature of this invention.

Determination of the 14-Gene Signature

Using data from expression profiling of the original 200 genes (i.e., the $\Delta(\Delta Ct)$ values obtained above), a semi-supervised principal component (SPC) method of determining survival time to distant metastasis was used to develop a list of genes that would comprise a prognostic signature. (E. Bair and R. Tibshirani, 2004, *PloS Biology* 2:0511-0522). SPC computation was performed using the PAM application, available online via the lab of R. Tibshirani at Standford University, Stanford, Calif. according to the method of R. Tibshirani, T J Hastie et al. 2002, *PNAS* 99:6567-6742.

Genes were first ranked according to their association with distant metastasis, using the univariate Cox proportional hazards model. Those genes with a P value <0.05 were considered significant. For any cutoff in the Cox score, SPC computed the component of genes (i.e., the principal component) that reached the optimal threshold: SPC used internal cross-validation in conjunction with a Cox model (with the principal component as the single variable) to select the optimal threshold. The first principal component gene list obtained by SPC was significant, and was used as a predictor in a univariate Cox model, in order to determine the correct sign and scaling.

The principal component gene list as produced by SPC was further reduced by the Lasso regression method. (R. Tibshirani, 1996, *J Royal Statistical Soc B*, 58:267-288). The Lasso regression was performed using the LARS algorithm. (B. Efron, T. Hastie et al., 2004, *Annals of Statistics* 32:407-499; T. Hastie, R. Tibshirani et al., eds., 2002, *The Elements of Statistical Learning*, Springer, N.Y.). The outcome variable used in the LARS algorithm was the principal component as selected by SPC. The Lasso method selected a subset of genes that could reproduce this score with a pre-specified accuracy.

Metastasis Score

The metastasis score (MS) has the form:

$$MS = a0 + b * \sum_{i=1}^{M} ai * Gi$$

Gi represents the standardized expression level of each Lasso-derived gene (i) of the 14-gene prognostic signature. The value of Gi is calculated from subtracting the mean gene expression of that gene in the whole population from the $\Delta(\Delta Ct)$ obtained in expression profiling described above and then divided by the standard deviation of that gene. The constant ai are the loadings on the first principal component of the fourteen genes listed in Table 2. The ai score for each gene i is provided in Table 2. The constant b is −0.251 and it was from a univariate Cox model with the principal component as a predictor, to get the correct sign and scaling. The constant a0=0.022; this centers the MS so that its median value is zero. M is the number of genes in the component list; in this case fourteen. Thus, the MS is a measure of the summation of expression levels for the 14 genes disclosed in Table 2, each multiplied by a particular constant ai; the summation was then multipled by the constant b and finally, this summation added to the centering constant 0.022.

The score is herein referred to as MS (all), as it was based on an analysis of all 142 ER-positive individuals studied. Any new sample may be evaluated by generating this metastasis score from the 14-gene expression profiling data for that patient, and optionally from this score, the probability of distant metastasis for the patient can be determined.

Generation of Distant Metastasis Probability form MS

The probability of distant metastasis for any individual patient can be calculated from the MS at variable time points, using the Weibull distribution as the baseline survival function.

The metastasis score (MS) obtained above, from expression profiling of the 14-gene signature, was converted into the probability of distant metastasis by means of the Cox proportional hazard model. Because the Cox model does not specify the baseline hazard function, the hazard and survivor functions were first constructed through parametric regression models. In the parametric regression models, distant metastasis-free survival time was the outcome, and the metastasis score (MS) was the independent variable input. The event time was assumed to have a Weibull distribution; its two parameters were estimated using the survival data from which the MS was derived. To calculate the probability of distant metastasis within a certain time for a patient, the MS value is simply substituted into the formula for the survivor function.

Pre-Validation

In this study, the 142 study patients were randomly divided into ten subsets. One subset was set aside and the entire SPC procedure was performed on the union of the remaining nine subsets. Genes were selected and the prognosticator built upon the nine subsets was applied to obtain the cross-validated metastasis score, MS (CV), for the remaining subset. This cross-validation procedure was carried out 10 times until MS (CV) was filled in for all patients. By building up MS (CV) in this way, each $1/10^{th}$ piece did not directly use its corresponding survival times, and hence can be considered unsupervised.

This resulted in a derived variable for all the individuals in the sample, and could then be tested for its performance and compared with other clinical variables. MS (all), however, was built upon all 142 individuals tested, and would produce considerable bias if tested in the same way.

MS (CV) was used to evaluate the accuracy of the 14-gene prognostic signature when time-dependent area under ROC curve (AUC) was calculated (described below). MS (CV) was also used in the Cox regression models when the 14-gene signature was combined with clinical predictors. MS (CV) should have one degree of freedom, in contrast to the usual (non-pre-validated) predictor. The non-pre-validated predictor has many more degrees of freedom.

Statistical Analyses of the MS

Kaplan-Meier (KM) curves for distant metastasis-free and overall survival were generated for the high- and low-risk patient groups using the median of MS (CV) as the cut point (i.e., 50 percentile of MS (CV)). The choice of median MS as cut point was based upon the calculation of the hazard ratios of the high vs. low-risk groups using different cut points from ten percentile of MS to ninety percentile of MS. A balanced number of high-risk and low-risk individuals as well as near the highest hazard ratio were the determining factors for choosing the median as the cut point.

Hazard ratios (HR) and 95% confidence intervals (CI) using the cut point of median MS were calculated and reported. Log rank tests were performed, and the hazard ratios were calculated for different cut points. The accuracy and value of the 14-gene signature in predicting distant metastasis at five years were assessed by various means. (X H Zhou, N. Obuchowski et al., eds., 2002, *Statistical Methods in Diagnostic Medicine*, Wiley-Interscience, New York).

Univariate and multivariate Cox proportional hazards regressions were performed using age, tumor size, tumor grade and the 14-gene signature. Clinical subgroup analyses on the signature were also performed. Statistical analyses were performed using SAS® 9.1 statistical software (SAS Institute, Inc., Cary, N.C.), except for the statistical packages noted herein.

Multi-Gene Signature

Of the 200 candidate genes studied, 44 had unadjusted P values <0.05 in a univariate Cox proportional hazards regression. Patients with poor metastasis prognosis showed an up-regulation of 37 genes, while seven genes were down-regulated. The semi-supervised principal component procedure (SPC) in PAM yielded a prognosticator of 38 genes. The gene list was further reduced to 14 (Table 2) by using the Lasso regression, via the LARS algorithm. Table 2 provides a description of each gene. Hazard ratios (HR) at various cut points (i.e., percentile MS (CV)) were calculated. The median of MS (CV) was chosen to classify patients into low- and high-risk groups.

Results

Figure 1:
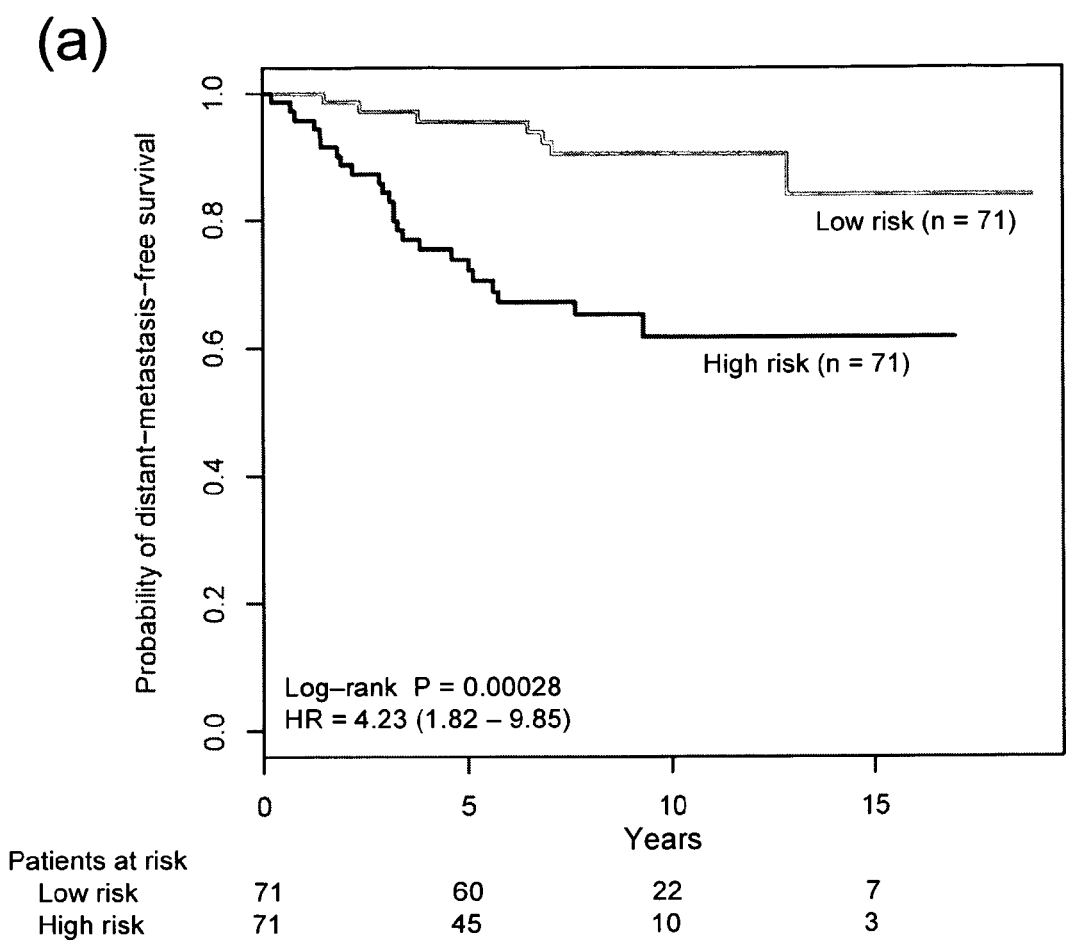
FIG. 1 shows Kaplan-Meier curves for a) time to distant metastases b) overall survival for training set from CPMC where high-risk and low-risk groups were defined by MS(CV) using zero as cut point.
Figure 1:
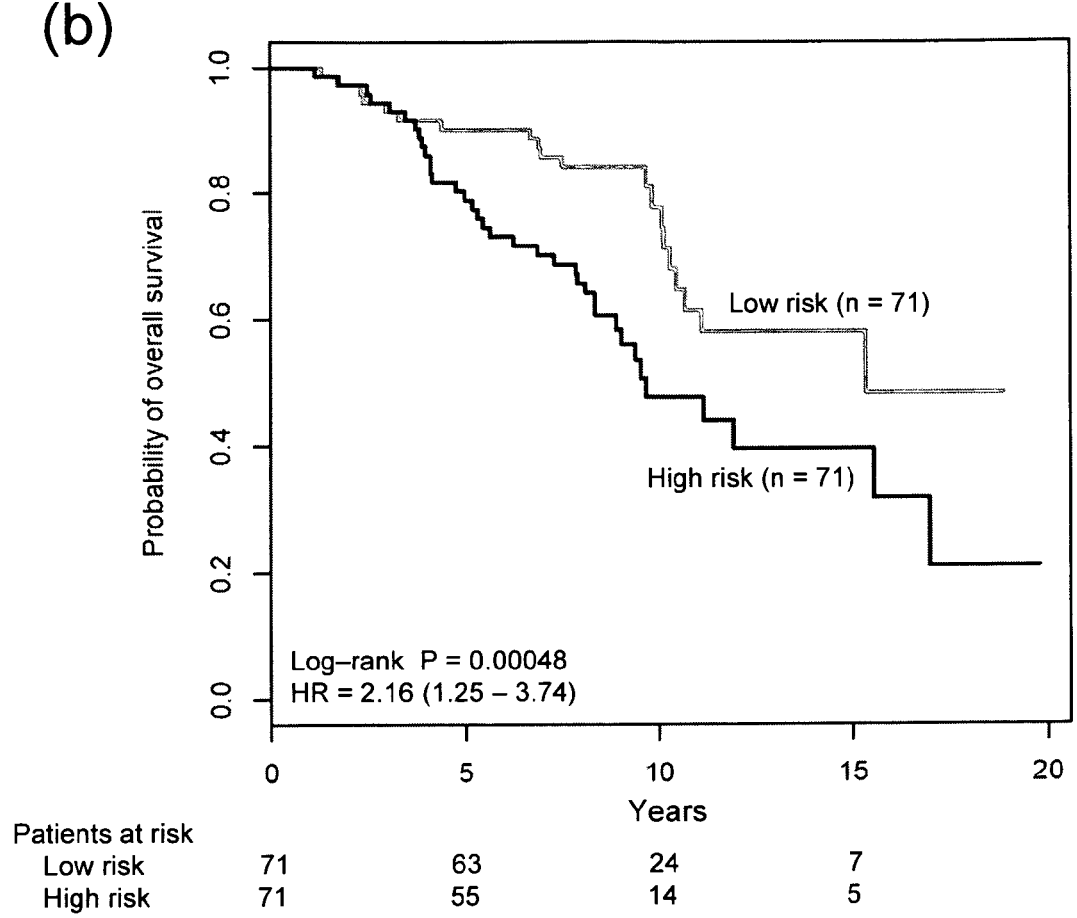

Distant-metastasis-free and overall survival rates in low-risk and high-risk groups There were 7 and 24 distant metastases in 71 low-risk and 71 high-risk patients as defined by the median of the cross-validated Metastasis Score, MS (CV), in the training set. Kaplan Meier estimate (FIG. 1*a*) indicated significant differences in distant metastasis free survival (DMFS) between the two groups with a log-rank p-value of 0.00028. The 5-year and 10-year DMFS rates (standard error) in the low-risk groups were 0.96 (0.025) and 0.90 (0.037) respectively. For the high-risk group, the corresponding rates were 0.74 (0.053) and 0.62 (0.066). For overall survival (FIG. 1*b*), there was also significant difference between the two groups (log-rank p-value=0.0048). The 5-year and 10-year OS rates (standard error) in the low-risk groups were 0.90 (0.036) and 0.78 (0.059) while the corresponding rates were 0.79 (0.049) and 0.48 (0.070) in the high-risk group (Table 5).

Hazard Ratios from Univariate and Multivariate Cox Regression Models

The unadjusted hazard ratio of the high-risk vs. low-risk groups by MS to predict DMFS was 4.23 (95% CI=1.82 to 9.85) (Table 6) as indicated by the univariate Cox regression analysis. In comparison, the high-risk vs. low-risk groups by tumor grade (medium+high grade vs. low grade) had an unadjusted hazard ratio of 2.18 (1.04-4.59). While tumor size was significant in predicting DMFS (p=0.05) with 7% increase in hazard per cm increase in diameter, age was not a significant factor in this patient set. In the multivariate Cox regression analyses, the 14-gene molecular signature risk group had a hazard ratio of 3.26 (1.26-8.38), adjusted by age at surgery, tumor size and grade. It was the only significant risk factor (p=0.014) in the multivariate analyses.

Diagnostic Accuracy and Predictive Values

Diagnostic accuracy and predictive values of the 14-gene signature risk groups to predict distant metastases within 5 years were summarized in Table 9. Sensitivity was 0.86 for those who had distant metastases within 5 years while specificity was 0.57 for those who did not. Negative predictive value (NPV) was 96% and indicated that only 4% of individuals would have distant metastasis within 5 years when the gene signature indicated that she was in the low-risk group. Nevertheless, positive predictive value (PPV) was only 26%, indicating only 26% of individuals would develop distant metastasis while the molecular signature indicated she was high-risk. The high NPV and low PPV were partly attributed to the low prevalence of distant metastasis in 5 years, which was estimated to be 0.15 in the current patient set.

Figure 2:
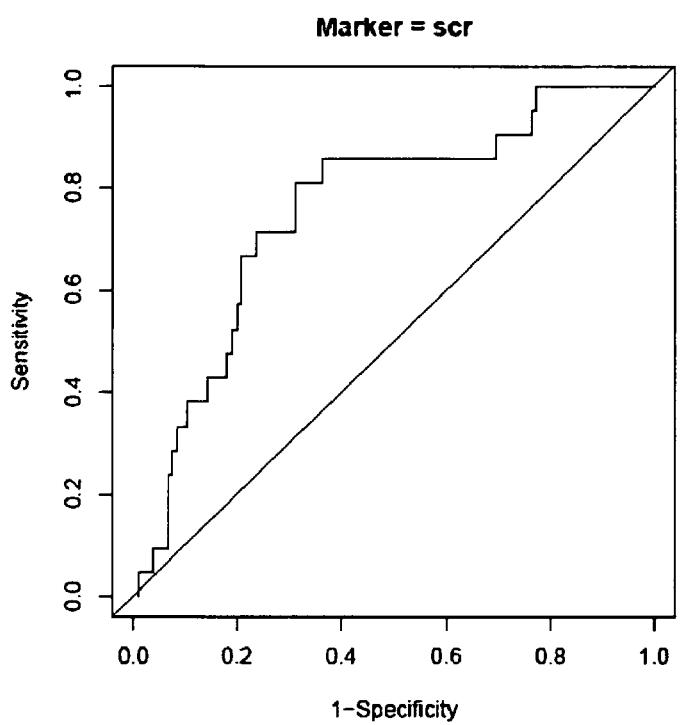
FIG. 2 is a ROC curve for predicting distant metastases by MS(CV) in 5 years in the training set from CPMC. AUC=0.76 (0.65-0.87).

Moreover, Receiver operating characteristics (ROC) curves of the continuous MS(CV) to predict distant metastases in 5 years was shown in FIG. 2. AUC was 0.76 (0.65-0.87) for predicting distant metastases in 5 years. AUC for predicting death in 10 years was 0.61 (0.49-0.73). One sided tests for AUC to be greater than 0.5 were significant with corresponding p-values of <0.0001 and 0.04 for the metastasis and death endpoints.

Discussion

Pathway analyses revealed that the fourteen genes in the prognostic signature disclosed herein are involved in a variety of biological functions, but a majority of the genes are involved with cell proliferation. Eleven of the fourteen genes are associated with the TP53 and TNF signaling pathways that have been found to be coordinately over-expressed in tumors leading to poor outcome. BUB1, CCNB1, MYBL2, PKMYT1, PRR11 and ORC6L are cell cycle-associated genes. DIAPH is a gene involved in actin cytoskeleton organization and biogenesis. DC13 is expected to be involved with the assembly of cytochrome oxidase.

Whereas previously reported studies were limited to the use of frozen tissues as the source of RNA and were profiled on microarrays, the invention described in this example demonstrates that real-time RT-PCR may be used for gene profiling in FFPE tumor samples. Thus, it provides for the use of archived breast cancer tissue sections from patients who have extended-outcomes data that predate the routine use of adjuvant therapy.

Distant metastasis-free survival is the prognostic endpoint for the study described in this example. A supervised principal components (SPC) method was used to build the 14-gene signature panel of the invention. The approach used in assembling the signature allowed the derivation of a metastasis score (MS) that can translate an individual's expression profile into a measure of risk of distant metastasis, for any given time period. The ability to quantify risk of metastasis for any timeframe provides highly flexible prognosis information for patients and clinicians in making treatment decisions, because the risk tolerance and time horizon varies among patients.

With the 14-gene molecular signature, high and low-risk groups had significant differences in distant metastasis-free and overall survival rates. This signature includes proliferation genes not routinely tested in breast cancer prognostics. The 14-gene signature has a ten gene overlap with the 50-gene signature described by H. Dai, L J van't Veer et al. (2005, in *Cancer Res* 15:4059-4066). In contrast, only six genes overlap with the 70-gene signature described by Dai, van't Veer et al. (2002, *Nature* 415:530-536). This may be explained by the fact that that study analyzed a more heterogeneous group of patients, which included both ER-positive and negative patients. The signature described herein had two proliferation gene overlaps with the 16-gene signature described by S P Paik, S. Shak et al., (2004, *N Engl J Med* 351:2817-2826).

The molecular signature described herein has independent prognostic value over traditional risk factors such as age, tumor size and grade, as indicated from multivariate analyses. This signature provides an even more compelling measure of prognosis when the tumor grade is low. As reported by Dai et al., a subset of this patient group with low grade tumors may be at even higher risk of metastasis than previously estimated. (Dai et al., 2005, *Cancer Res* 15:4059-4066). The signature described herein also extends the confidence in the prognostic genes initially reported by van't Veer et al. (2002, *Nature* 415:530-536) and Dai et al. (2005, *Cancer Res* 15:4059-4066), who primarily used samples from women less than 55 years of age, because this signature was validated on patients with a broad age distribution (median 64 years old), which is similar to the general range of breast cancer patients.

The use of FFPE tissues to sample even smaller amounts of sectioned tumor than microarray studies using frozen tissue, corroborated a subset of the genes on a different detection platform (quantitative PCR versus microarrays). This reiteration of results is consistent with the concept described by Bernards and Weinberg, that metastatic potential is an inherent characteristic of most of, rather than a small fraction of, the cells in a tumor. (R. Bernards and R A Weinberg, 2002, *Nature* 418:823).

The invention described herein also provides an objective estimate of prognosticator performance by using the pre-validation technique proposed by Tibshirani and Efron. (R. Tibshirani, B. Efron, 2002, *Statistical Applications in Genetics and Molecular Biology* 1:article 1). Several investigators have noted the importance of independent validation in increasingly large and characterized datasets. (R. Simon, *J Clin Oncol*, 2005, 23:7332-7341; D F Ransohoff, 2004, *Nat Rev Cancer* 4:309-14; D F Hayes, B. Trock et al., 1998, *Breast Cancer Res* 52: 305-319; D G Altman and P. Royston, 2000, *Stat Med* 19:453-73).

In the present invention, a unique 14-gene prognostic signature is described that provides distinct information to conventional markers and tools and is not confounded with systemic treatment. While the signature was developed using FFPE sections and RT-PCR for early stage, node-negative, ER-positive patients, it may be used in conjunction with any method known in the art to measure mRNA expression of the genes in the signature and mRNA obtained from any tumor tissue source, including but not limited to, FFPE sections, frozen tumor tissues and fresh tumor biopsies. Based on the mRNA expression levels of the 14-gene signature of the invention, a metastasis score can be calculated for quantifying distant metastasis risk for any individual breast cancer patient. Thus, the invention disclosed herein is amenable for use in routine clinical laboratory testing of ER-positive breast cancer patients for any timeframe.

Example Two

The 14-Gene Signature Predicts Distant Metastasis in Untreated Node-Negative, ER-Positive Breast Cancer Patients Using 280 FFPE Samples Efforts were undertaken to validate the 14-gene expression signature that can predict distant metastasis in node-negative (N−), estrogen receptor positive (ER+) breast cancer patients in an independent sample set who had not received systemic treatment. Reference is made to the experimental protocols and statistical analyses in Example 1, which were used to assay the effectiveness of the 14-gene signature.

Patients & Methods

A retrospective search of the Breast Tissue and Data Bank at Guy's Hospital was made to identify a cohort of patients diagnosed with primary breast cancer and who had definitive local therapy (breast conservation therapy or mastectomy) but no additional adjuvant systemic treatment. The study group was restricted to women diagnosed between 1975 and 2001, with a clinical tumor size of 3 cm or less, pathologically uninvolved axillary lymph nodes, ER-positive tumor and with more than 5 years follow-up. A total of 412 patients were identified who also had sufficient formalin fixed, paraffin embedded (FFPE) tissues available for RNA extraction. The use of patient material and data for this study has been approved by Guy's Research Ethics Committee.

From this group there was sufficient quantity and quality of mRNA to profile tumors from 300 patients. Subsequently a further 20 cases were excluded from the study. Six patients had bilateral breast cancer prior to distant metastasis, 6 had a missing value in gene expression levels and 8 tumors proved to be ER negative upon re-assessment using current techniques. Thus, in total 280 patients were included in the analyses (validation set from Guy's Hospital in Table 1). To assess selection bias, we compared the 280 patients we analyzed with the 412 patients who were identified to satisfy the inclusion criteria and had sufficient FFPE tissues for RNA extraction. No selection bias was detected as there were no significant differences in age, tumor size and histologic grade between the two sets.

ER status on this group of patients had been re-evaluated using contemporary IHC assay. Allred score 3 or more were considered receptor positive. Tumors were classified according to WHO guidelines (World Health Organization, Geneva, Switzerland. Histological typing of breast tumours. Tumori 1982; 68:181), and histological grade established using the modified Bloom and Richardson method (Elston C W & Ellis I O. Pathological prognostic factors in breast cancer. I. The value of histological grade in breast cancer: experience from a large study with long term follow-up. Histopathology 1991; 19:403-10).

Compared with the training set, the validation set was younger, with larger tumors and with a larger proportion of high grade tumors (Table 1). Tests for differences in those characteristics are highly significant (p<0.001).

Metastasis Score

MS in Equation 1 derived in the training samples in Example 1 was applied to the untreated patients from Guy's Hospital. In example 1, RNA had been enriched, whereas in the case of untreated patients from Guy's Hospital, the RNA samples were not enriched.

To apply MS to the un-enriched samples, conversion factors between enriched and un-enriched samples were obtained from 93 training samples in Example 1 for each of the genes in the molecular signature.

Results

Distant Metastasis Free and Overall Survival Rates in Low-Risk and High-Risk Groups There were 4 (5.6%) distant metastases in the 71 MS low-risk and 62 (29.7%) distant metastases in the 209 MS high-risk patients, respectively. Kaplan Meier estimate (FIG. 3a) indicated significant differences in DMFS between the two groups with a log-rank p-value of 6.02e-5. The 5-year and 10-year DMFS rates (standard error) in the low-risk group were 0.99 (0.014) and 0.96 (0.025) respectively. For the high-risk group, the corresponding survival rates were 0.86 (0.025) and 0.76 (0.031) (Table 12).

For the Adjuvant! risk groups, Kaplan Meier curves of DMFS were shown in FIG. 3c. The 5-year and 10-year DMFS rates (standard error) were 0.96 (0.023) and 0.93 (0.03) for the low-risk group and 0.87 (0.03) and 0.77 (0.031) for the high-risk group, respectively. There were larger differences in survival rates between the high-risk and low-risk groups defined by MS than those defined by Adjuvant!.

For overall survival (OS), Kaplan Meier curves (FIG. 3b) indicated significant difference in OS rates between MS low-risk and high-risk groups (log-rank p-value=0.00028). The 5-year and 10-year OS rates were 0.97 (0.020) and 0.94 (0.028) for the low-risk group and 0.92 (0.019) and 0.71 (0.032) for the high-risk group, respectively. FIG. 3d showed the Kaplan Meier curves for Adjuvant! to predict 5-year and 10-year overall survival. MS and Adjuvant! provide similar prognostic information for overall survival.

Hazard Ratios from Univariate and Multivariate Cox Regression Models

The unadjusted hazard ratio of the high-risk vs. low-risk groups by MS to predict time to distant metastases was 6.12 (95% CI=2.23 to 16.83) (Table 10). The unadjusted hazard ratio for MS risk groups is higher than those for groups defined by Adjuvant!, age, tumor size and histologic grade. Adjuvant! had the second highest hazard ratio of 2.63 (95% CI 1.30–5.32). Risk groups by histologic grade and tumor size were significant in predicting DMFS, but not the age group.

Age group is the most significant prognostic factor in predicting OS with an unadjusted hazard ratio of 2.9 (95% CI 2.03–4.18) (Table 10). Nevertheless, MS risk group can predict overall survival with HR of 2.49.

In the multivariate Cox regression (Table 11a) of time to distant metastases with the MS risk group and clinicopathological risk factors of age, tumor size and histological grade, the hazard ratio of the MS risk group, adjusted by age, tumor size and histologic grade, is 4.81 (1.71-13.53, p=0.003). MS risk group was the only significant risk factor in the multivariate analysis. Therefore, the gene signature has independent prognostic value for DMFS over the traditional clinicopathological risk factors and captures part of information within these factors.

In the multivariate Cox regression of time to distant metastases with the risk groups by the 14-gene signature and by Adjuvant! (Table 11b), the corresponding adjusted hazard ratios were 5.32 (1.92-14.73) and 2.06 (1.02-4.19). Both MS and Adjuvant! risk groups remained significant to predict DMFS. This indicates that MS and Adjuvant! carried largely independent and complementary prognostic information to each other.

Performance of the Molecular Signature in Different Clinical Subgroups

Table 13 shows that the gene signature predicts distant metastasis in young and old, pre-menopausal and post-menopausal women. While highly prognostic in patients with small size tumors (HR=14.16, p=0.009), it is not significant in patients with tumors larger than 2 cm. While hazard ratio in the low-grade subgroup (HR=7.6) is higher than that in the high-grade (HR=4.6), it only shows a trend to significance (p=0.06) in the low-grade subgroup because of small sample size (7 events in 60 samples).

Hazard ratios in various subgroups indicated that the gene signature is more prognostic in low grade, small size tumors, young and pre-menopausal patients in the validation sample set.

Formal tests for interaction between the MS risk group and the clinical variables were not significant. However, the signature was also more prognostic in the low-grade tumors in the CPMC training set. Nevertheless, interaction analyses should be regarded as exploratory as multiple tests were performed.

Diagnostic Accuracy and Predictive Values

The diagnostic accuracy and predictive values of the risk groups by MS and Adjuvant! to predict distant metastases in 10 years were shown in Table 14. The MS risk group has higher sensitivity of 0.94 (0.84-0.98) than the Adjuvant! risk group's 0.90 (0.78-0.96) while the specificity is similar (0.3 (0.24-0.37) for MS vs. 0.31 (0.26-0.38) for Adjuvant!). Using 0.18 as the estimated prevalence of distant metastases in 10 years, PPV and NPV for MS risk group were 0.23 (0.21-0.25) and 0.97 (0.88-0.99) respectively. The corresponding values were 0.23 (0.20-0.25) and 0.93 (0.85-0.97) for the Adjuvant! risk group. Therefore, MS can slightly better predict those who would not have distant metastases within 10 years than Adjuvant! while the predictive values for those who would have distant metastases within 10 years were similar for the molecular and clinical prognosticators.

ROC curves (FIG. 4) of continuous MS to predict distant metastasis within 5 years and 10 years had AUC (95% CI) of 0.73 (0.65-0.81), 0.70 (0.63-0.78). A ROC curve to predict death in 10 years had an AUC of 0.68 (0.61-0.75). Hence, MS are predictive of both distant metastases and deaths.

In comparison, AUCs of ROC curves to predict distant metastases within 5 years, 10 years and death in 10 years by Adjuvant! were 0.63 (0.53-0.72), 0.65 (0.57-0.73) and 0.63 (0.56-0.71) and they were lower than the corresponding values by MS.

MS as a Continuous Predictor of Probability of Distant Metastasis

FIG. 5 shows the probabilities of distant metastasis at 5 and 10 years for an individual patient with a metastasis score, MS. Five-year and ten-year distant metastasis probabilities have median (min-max) of 8.2% (1.4%-31.2%) and 15.2% (2.7%-50.9%) respectively. At zero MS, the cut point to define the risk groups, the 5-year and 10-year distant metastasis probabilities were 5% and 10%, respectively.

The probability of distant metastasis in 10 years by MS was compared with the probability of relapse in 10 years by Adjuvant! (FIG. 6). The coefficient of determination ($R^2$) was 0.15 indicating that only a small portion of variability in probability of distant metastasis by MS can be explained by Adjuvant! The probability of distant metastasis by MS was lower than the relapse probability by Adjuvant! as all recurrence events were included in the Adjuvant! relapse probability while only distant metastases were counted as an event in the MS estimate of probability of distant metastasis.

Discussion

Initially a 14-gene prognostic signature was developed based upon mRNA expression from FFPE sections using quantitative RT-PCR for distant metastasis in a node-negative, ER-positive, early-stage, untreated breast cancer training set. The resulting signature was used to generate a metastasis score (MS) that quantifies risk for individuals at different timeframes and was used to dichotomize the sample set into high and low risk. Following initial internal validation of training set using a recent "pre-validation" statistical technique, we validated the expression signature using the precise dichotomized cutoff of the training set in a similar and independent validation cohort. Performance characteristics of the signature in training and validation sets were similar. Univariate and multivariate hazard ratios were 6.12 and 4.81 for the validation set and 4.23 and 3.26 in the training set to predict DMFS, respectively. In multivariate analysis, only the metastasis score remained significant with a trend to significance for only tumor size of the other clinicopathological factors. The 14-gene prognostic signature can also predict overall survival with univariate hazard ratios of 2.49 in the validation set. ROC curves of continuous MS to predict distant metastasis within 5 and 10 years and to predict death in 10 years had AUC of 0.73, 0.70 and 0.68, respectively. The signature provided more compelling prognosis when the tumor grade was low (hazard ratio were 7.58 in the low grade and 4.59 in the high grade tumors). Dai et al, for example, interpreted the change in prognostic power of the classifier as not being reflective of a continuum of patients but instead differential performance in discrete groups of patients.

When compared to risk calculated from Adjuvant!, a web-based decision aid, there was only a modest correlation with MS. In multivariate Cox regression, MS and Adjuvant! risk groups both remain significant prognostic factors when they are adjusted for each other. There were larger differences in survival rates between the high-risk and low-risk groups defined by MS relative to Adjuvant!. MS can better predict those who would not have distant metastases within 10 years than Adjuvant!. These data demonstrate that the molecular signature provides independent information to the prognostic tools either routinely or more recently being adopted for predicting breast cancer distant metastasis.

Example Three

The 14-Gene Signature Predicts Distant Metastasis in Both Treated and Untreated Node-Negative and ER-Positive Breast Cancer Patients Using 96 FFPE Samples Efforts were undertaken to validate a 14-gene expression signature that can predict distant metastasis in node negative (N−), estrogen receptor positive (ER+) breast cancer patients in an independent sample set having both treated and untreated patients. Reference is made to the experimental protocols and statistical analyses in Example 1, which were used to assay and evaluate the effectiveness of the 14-gene signature.

Patients & Methods

A cohort of 96 N−, ER+ breast cancer patients, with a mean age of 56.7 years, was selected for the validation study (Table 15). The patients in the validation study were selected from University of Muenster. Of those, 15 were untreated, 54 were treated with Tamoxifen alone, 6 were treated with chemotherapy alone, and 2 were treated with both Tamoxifen and chemotherapy. Nineteen patients had unknown treatment status. The fourteen genes in the signature were profiled in FFPE samples using quantitative RT-PCR. A previously derived metastasis score (MS) was calculated for the validation set from the gene expression levels. Patients were stratified into two groups using a pre-determined MS cut point, which was zero.

Validation of Metastasis Score

MS in Equation 1 that was derived with samples in Example 1 was applied to the patients from University of Muenster. In this example, RNA from the tumor tissues was also enriched but to a lesser extent than those in Example 1. To apply MS to this example, conversion factors between enriched and un-enriched samples were obtained from 93 samples from University of Muenster for each of the 14 genes in the signature. The conversion factors between enriched and unenriched samples were also obtained from 93 training samples from CPMC in Example 1. The conversion factors between the gene expression levels from CPMC and University of Muenster were then calculated using those two sets of conversion factors.

Results

Distant-metastasis-free Survival Rates

Using MS zero as cut point, patients were classified as high-risk and low-risk. Of all 96 patients, 48 patients were identified as high-risk with a 5-year DMF survival rate (standard error) of 0.61 (0.072) while 48 low-risk patients had a corresponding survival rate of 0.88 (0.052). Of the 62 treated patients, 32 high-risk and 30 low-risk patients had 5-yr DMF survival rates of 0.66 (0.084) and 0.89 (0.060), respectively. Of the 54 patients who received Tamoxifen treatment alone, 26 high-risk and 28 low-risk patients had 5-yr DMF survival rates of 0.65 (0.094) and 0.88 (0.065) respectively (Table 16).

Unadjusted Hazard Ratios

For the entire cohort, the MS correlated with distant metastasis-free (DMF) survival. Cox proportional hazard regression indicated 2.67 (1.28-5.57) times increased hazard per unit increase of MS (p=0.0087). Using zero as cut point, The hazard ratio of high-risk vs. low-risk patients in the entire cohort was 2.65 (1.16-6.06, p=0.021). For 61 treated patients, the hazard ratio was 3.08 (0.99-9.56, p=0.052). For the 54 patients who were treated with Tamoxifen only, the hazard ratio was 2.93 (0.92-9.35, p=0.07). Survival rates and hazard ratios for different groups of patients are summarized in Table 16 and FIG. 7, respectively.

An RT-PCR based 14-gene signature, originally derived from untreated patients, can predict distant metastasis in N−, ER+, Tamoxifen-treated patients in an independent sample set using FFPE tissues. There was a large differential DMFS rates between high and low risk Tamoxifen-treated alone patients (0.65 vs. 0.88) where two groups were defined by MS using zero as cut point. Differential risk between top and bottom quintiles of multi-modal MS were 3.99 and 3.75 fold for all and Tamoxifen-treated alone patients, respectively. The prognostic signature may provide baseline risk that is not confounded with systemic treatment. Moreover, it can predict metastatic risk for patients who receive treatment. Therefore, the gene signature would be applicable in identifying women with a poor clinical outcome to guide treatment decisions, independent of the subsequent therapies.

Example Four

The 14-Gene Signature Predicts Distant Metastasis in Tamoxifen-Treated Node-Negative and ER-Positive Breast Cancer Patients Using 205 FFPE Samples Patients A cohort of 205 women with N−, ER+ breast cancer who had surgery between 1975 and 2001 in Guy's Hospital was selected. The median follow-up was 9.3 years. Among them, there were 17 (8.9%) distant metastases, 44 deaths (21.5%) and 17 (8.9%) local and distant recurrences.

138 (67.3%) patients were at stage I while 67 (32.7%) were at stage II. All patients received adjuvant hormonal treatment but no chemotherapy. The cohort had a mean (SD) age of 59.3 (10.4) years. 64% were over the age of 55 years and 80.5% were post-menopausal. All tumors were ≦3 cm in diameter and the mean (SD) tumor diameter was 1.67 cm (1.0). 60 (29.3%), 98 (47.8%) and 47 (22.9%) patients had tumors of histological grade 1, 2 and 3, respectively. (Table 17)

Endpoints

We chose time from surgery to distant metastasis, also referred to as distant-metastasis-free survival (DMFS), as the primary endpoint. Events were distant metastases. Contralateral recurrences and deaths without recurrence were censoring events while local recurrences were not considered events or censoring events. The definition of DMFS endpoint, its events and censoring rules were aligned with those adopted by the National Surgical Adjuvant Breast and Bowel Project (NSABP) for the prognostic molecular marker studies (Paik et al 2004). The DMFS endpoint is most directly linked to cancer related death.

Gene Expression Signature and Metastasis Score (MS)

A 14-gene signature was previously developed using profiling study by RT-PCR with FFPE samples from California Pacific Medical Center (CPMC) as described in Example 1. Pathway analyses by the program Ingenuity revealed that the majority of the 14 genes in the signature are involved with cell proliferation. Ten of 14 genes are associated with TP53 signaling pathways that have been found to be coordinately over-expressed in tumors of poor-outcome.

A Metastasis Score (MS) was calculated for each individual. MS in this example was based upon the gene expression of the 14 genes in the signature as previously described. However, the algorithm for calculating MS in this example was different from the algorithm described for the previous examples. Nevertheless, MS derived with the new algorithm was highly correlated with MS derived with the previous method with Pearson correlation coefficient >0.99. Moreover, in this example, two cut points were employed to group patients into high, intermediate and low MS groups as opposed to using only one cut point to categorize patients into low and high risk groups in the previous three examples.

While the 14 genes in the signature were chosen in the study as described in Example 1, the new MS score and cut points were determined based upon the study using untreated samples from Guy's Hospital as described in Example 2. The new MS algorithm was applied and validated in Examples 4 and 5. The new Metastasis Score (MS(new)) is now calculated as the negative of the mean of the gene expression level of 14 genes. With this new score, the fourteen genes were given equal weighting. The −1 multiplier was used so that higher MS corresponds to higher risk of distant metastasis. The new MS can be expressed in the following formula:

$$MS(\text{new}) = -(1/14) * \left[\sum_{i=1}^{14} Gi\right] \quad \text{Equation 3}$$

where Gi are the centered expression levels of the 14 genes in the signature.

Two cut points of MS(new) were chosen to categorize patients into high, intermediate and low MS groups. The lower cut point was −1.47 while the upper cut point was −0.843. Individuals with MS smaller than −1.47 were in the low MS group. Individuals with MS between −1.47 and −0.843 were in the intermediate MS group while those with MS greater than −0.843 were in the high MS group. If those with low MS were considered low-risk while those in intermediate MS and high MS groups were considered as high risk in Guy's untreated samples (in other word those with MS above −1.47 were considered high risk), then sensitivity of the MS risk groups would be above 90%. On the other hand, if those with low MS and intermediate MS were considered low-risk while those with high MS were considered high-risk (in other words, those with MS lower than −0.843 were considered low-risk while those with MS higher than −0.843 were considered high-risk), then the sensitivity and specificity of the MS risk groups in Guy's untreated samples would be the same at 70%.

For the untreated samples, the intermediate MS group has risk similar to that of high MS group and the high and intermediate MS groups had higher risk than those with low MS. However, for patients treated with hormonal treatment, the intermediate MS group has risk similar to that of the low MS group. The risk of high MS group is higher than the risk of intermediate MS and low MS groups.

Another method of applying the 14 gene signature is by using Equation 2, as follows. A 14-gene signature was previously developed using profiling study by RT-PCR with FFPE samples from California Pacific Medical Center (CPMC) as described in Example 1. Pathway analyses by the program Ingenuity revealed that the majority of the 14 genes in the signature are involved with cell proliferation. Ten of 14 genes are associated with TP53 signaling pathways that have been found to be coordinately over-expressed in tumors of poor-outcome.

A Metastasis Score (MS) was calculated for each individual. MS in this example was based upon the gene expression of the 14 genes in the signature as previously described. However, the algorithm for calculating MS in this example was based upon Equation 2 in which the fourteen genes were weighted equally. Moreover, in this example, two cut points were employed to group patients into high, intermediate and low MS groups as opposed to using only one cut point to categorize patients into low and high risk groups in the previous three examples. While the 14 genes in the signature were chosen in the study as described in Example 1, the new MS score and cut points were determined based upon the study using untreated samples from Guy's Hospital as described in Example 2. The new MS algorithm was applied and validated in Examples 4 and 5.

Two cut points of MS(new) were chosen to categorize patients into high, intermediate and low MS groups. Cut points were determined such that when individuals with MS above the first cut point of −0.119 were classified as high-risk individuals to have distant metastasis in 5 years, the sensitivity of the MS risk groups would be above 90%. The second cut point of MS=0.302 was chosen such that sensitivity and specificity would be the same at 0.7.

It should be noted that the MS determined in Equation 2 and MS as the negative of the mean of gene expression of all fourteen genes are simply linear transformation of each other. As such they have perfect correlation (Pearson correlation coefficient=1) and the classification of patients into high, intermediate, and low MS are the same using the corresponding cut points as described.

Statistical Analyses

Kaplan-Meier (KM) curves for distant metastasis free survival were generated for the high, intermediate and low MS groups. Upon examining the DMFS rates of the three groups, intermediate and low MS groups were combined as a low-risk group which was compared with the high risk group with high MS. Log rank tests were performed.

Univariate and multivariate Cox proportional hazard regression analyses of MS groups for DMFS endpoint were performed. Hazard ratio of high-risk (high MS) vs. low-risk (intermediate and low MS groups combined) group was adjusted for age (in years), tumor size (in cm) and histological grade in multivariate analysis.

Association of MS groups with age, tumor size was investigated using ANOVA tests while association of MS groups with histological grade was evaluated by Crammer's V for strength of association and by chi-sq tests for statistical significance.

Hazard ratios of the MS risk groups were also calculated for different clinical subgroups. Those groups include pre-menopausal vs. post-menopausal, age $\leq 55$ years vs. $>55$ years, tumor size $>2$ cm vs. $\leq 2$ cm, and histological grade 1 & 2 vs. grade 3.

To assess diagnostic accuracy, Receiver Operator Characteristic (ROC) curve of MS to predict distant metastases within 5 years was plotted. Area under the ROC curves (AUC) was calculated. Sensitivity, specificity, positive predictive value (PPV) and negative predictive value (NPV) were calculated with 95% confidence interval (95% CI) for high vs. low-risk groups by MS.

The time-dependence of hazard ratio of MS groups was investigated by estimating the annualized hazards using a spline-curve fitting technique that can handle censored data. The HEFT procedure in R2.4.1 was employed. Annualized hazards were estimated for both MS high and low-risk groups and from which, the hazard ratios at different time were calculated.

Kaplan Meier estimates and Cox proportional hazard regression were performed using R2.41.1 and SAS 9.1. ROC curves and AUC were estimated using the Mayo Clinic's ROC program. The Delong method of estimating confidence interval of AUC was employed.

Results

Distant-metastasis-free Survival Rates in MS Low-risk and High-risk Groups

There were 8 distant metastases in the low MS group of 136 individuals, 2 distant metastases in the intermediate MS group of 29 individuals and 7 distant metastases in the high MS group of 40 individuals. The 10-year DMFS rates (SE) were 0.921 (0.028), 0.966 (0.034) and 0.804 (0.068) for low, intermediate, and high MS groups, respectively. There were significant differences in DMFS rates with a log-rank p-value of 0.04. As DMFS rates were similar in low and intermediate MS groups, they were combined to form the low-risk group. The low-risk group had a 10-year DMFS rate of 0.928 (0.025) and was significantly different from the corresponding rate of 0.804 (0.068) for the high-risk group (Table 18). The log-rank p-value was 0.011. Kaplan-Meier plots of distant-metastasis-free survival for the three MS groups and the two MS risk groups were in FIG. 8 and FIG. 9, respectively.

Hazard Ratios from Univariate and Multivariate Cox Regression Models

The unadjusted hazard ratio of the MS high-risk vs. low-risk groups to predict time to distant metastases was 3.25 (95% CI=1.24 to 8.54, p-value=0.017). When adjusted by age, tumor size and histological grade, the hazard ratio was 5.82 (1.71-19.75, p=0.0047) in Table 19. MS risk group was the only risk factor that was significant in the multivariate analyses. Therefore, the gene signature has independent prognostic value for DMFS over the traditional clinicopathological risk factors and captures part of the information of these factors.

Association of MS Risk Groups with Other Clinical and Pathological Characteristics MS risk group had very significant association with histological grade (Crammer's V=0.65, p<0.0001 for chi-sq test for association). For 60 grade 1 tumors, none (0%) was MS high-risk. In contrary, 9 (9.2%) of 98 grade 2 and 31 (66%) of 47 grade 3 tumors were MS high-risk.

While tumor size was larger in the MS high-risk group, the difference was not statistically different (1.87 cm and 1.61 cm in MS high and low-risk groups respectively, ANOVA p-value=0.14). There was no significant association of MS risk groups with age (Mean age is 59.3 in both high and low-risk groups, ANOVA p=0.34). Results were summarized in Table 20.

Performance of the Molecular Signature in Different Clinical Subgroups

Hazard ratio of MS risk groups was 3.7 (1.1-12.6) in tumors ≦2 cm and 3.0 (0.6-14.8) in tumors >2 cm. In women younger than 55 years, HR was 7.4 (1.0-54.7) while it was 2.8 (0.88-8.8) in women older than 55 years. For tumors of histological grade 1 and 2, HR was 12.8 (3.8-43.1) while HR was 1.53 (0.16-14.7) in grade 3 tumors (Table 21).

Diagnostic Accuracy and Predictive Values

Sensitivity, specificity, PPV and NPV of MS risk groups to predict distant metastasis in 5 years were shown in Table 22. Sensitivity of MS risk group was 0.50 (0.50-0.76) while specificity was 0.82 (0.76-0.87). Using the estimated 5-year distant metastasis rate of 0.05, PPV and NPV were estimated to be 0.13 (0.068-0.23) and 0.97 (0.94-0.98) respectively (Table 22). High NPV of the MS risk group was important for it to be used for ruling out more aggressive treatment such as chemotherapy for patients with low-risk.

ROC curve of continuous MS to predict distant metastasis within 5 years was shown in FIG. 10 and AUC was estimated to b 0.72 (0.57-0.87).

Time Dependence of the Prognostic Signature

Annualized hazard rates for MS high and low-risk groups were shown in FIG. 11a while the time-dependence of the hazard ratio between two groups was shown in FIG. 11b. For the high-risk group, annual hazard rate peaked at 2.5% around year 3 from surgery and then slowly decreased over the next few years. However, the annualized hazard rate in the low-risk group showed slight but steady increase in the 10-year period that had follow-up. Subsequently, hazard ratio of MS risk groups was time dependent. It was 4.6, 3.6 and 2.1 at year 2, 5 and 10, respectively.

Example Five

The 14-Gene Signature Predicts Distant Metastasis in Adjuvant Hormonally-Treated Node-Negative and R-Positive Breast Cancer Patients Using 234 FFPE Samples Patients A cohort of 234 Japanese women with N−, ER+ breast cancer who had surgery between 1995 and 2003 in Aichi Cancer Center was selected. The median follow-up was 8.7 years. Among them, there were 31 (13%) distant metastases, 19 deaths (8.1%) and 46 (19.7%) local and distant recurrences.

146 (62%) patients were at stage I while 88 (38%) were at stage II. All patients received adjuvant hormonal treatment but no chemotherapy. 112 post-menopausal women were treated with Tamoxifen. Of 122 pre-menopausal women, 102 received Tamoxifen while 20 received Zoladex treatment. The cohort had a mean (SD) age of 53 (11) years and mean (SD) tumor diameter of 2.05 cm (1.1). 74 (32%), 113 (48%) and 47 (20%) patients had tumors of histological grade 1, 2 and 3, respectively. (Table 23)

Gene Expression Signature and Metastasis Score (MS)

A 14-gene expression signature was previously developed and validated in profiling studies in US and Europe using RT-PCR with FFE samples. Pathway analyses by the program Ingenuity revealed that the majority of the 14 genes in the signature are involved with cell proliferation. Ten of 14 genes are associated with TP53 signaling pathways that have been found to be coordinately over-expressed in tumors of poor-outcome.

A Metastasis Score (MS) was calculated for each individual. MS was based upon the negative of the mean of the gene expression levels (in ΔΔCt) of the 14 genes in the signature. Moreover, two cut points had previously been determined from a study with tumor samples from untreated patients from Guy's Hospital (Example 2) to group patients into high, intermediate and low MS groups.

Statistical Analyses

Kaplan-Meier (KM) curves for distant metastasis free and overall survival were generated for the high, intermediate and low MS groups. Upon examining the DMFS rates of the three groups, intermediate and low MS groups were combined as a low-risk group which was compared with the high risk group with high MS. Log rank tests were performed.

Univariate and multivariate Cox proportional hazard regression analyses of MS groups for DMFS and OS endpoints were performed. Hazard ratio of high-risk (high MS) vs. low-risk (intermediate and low MS groups combined) group was adjusted for age (in years), tumor size (in cm) and histological grade in one multivariate analysis. In another multivariate analysis, it was adjusted for menopausal status, treatment, tumor size, histological grade and PgR status.

Association of MS groups with age, tumor size was investigated using ANOVA tests while association of MS groups with histological grade and tumor subtypes was evaluated by Crammer's V for strength of associated and by chi-sq tests for statistical significant.

Hazard ratios of the MS risk groups were also calculated for different clinical subgroups. Those groups include pre-menopausal vs. post-menopausal, age ≦55 years vs. >55 years, tumor size >2 cm vs. ≦2 cm, and histological grade 1 & 2 vs. grade 3, PgR+ve vs.−ve.

To assess diagnostic accuracy, Receiver Operator Characteristic (ROC) curve of MS to predict distant metastases within 5 years was plotted. Area under the ROC curves (AUC) was calculated. Sensitivity, specificity, positive predictive value (PPV) and negative predictive value (NPV) were calculated with 95% confidence interval (95% CI) for high vs. low-risk groups by MS.

The time-dependence of hazard ratio of MS groups was investigated by estimating the annualized hazards using a spline-curve fitting technique that can handle censored data. The HEFT procedure in R2.4.1 was employed. Annualized hazards were estimated for both MS high and low-risk groups and from which, the hazard ratios at different time were calculated.

Kaplan Meier estimates and Cox proportional hazard regression were performed using R2.41.1 and SAS 9.1. ROC curves and AUC were estimated using the Mayo Clinic's ROC program. The Delong method of estimating confidence interval of AUC was employed.

Results

Distant-metastasis-free Survival Rates in MS Low-risk and High-risk Groups

There were 6 distant metastases in the low MS group of 77 individuals, and 4 distant metastases in the intermediate MS group of 66 individuals and 21 distant metastases in the high MS group of 95 individuals. The 10-year DMFS rates (SE) were 0.89 (0.05), 0.91 (0.04) and 0.75 (0.05) for low, intermediate, and high MS groups, respectively. There was significant difference in DMFS rates with a log-rank p-value of 0.004. As DMFS rates were similar in low and intermediate MS groups, they were combined to form the low-risk group. The low-risk group had a 10-year DMFS rate of 0.895 (0.034) and is significantly different from the corresponding rate of 0.75 (0.05) for the high-risk group (Table 24). The log-rank p-value is 0.00092. Kaplan-Meier plots of distant-metastasis-free survival for three MS groups were in FIG. 12 while Kaplan-Meier plots for the two risk groups (high MS and a combination of intermediate and low MS) were in FIG. 13.

Hazard Ratios from Univariate and Multivariate Cox Regression Models

The unadjusted hazard ratio of the MS high-risk vs. low-risk groups to predict time to distant metastases was 3.32 (95% CI=1.56 to 7.06, p-value=0.0018). When adjusted by age, tumor size and histological grade, the hazard ratio was 3.79 (1.42-10.1, p=0.0078). Beside MS, tumor size is the only other significant factor in the multivariate analyses with HR of 1.4 per cm increase (p=0.007) (Table 25). In another multivariate analysis, MS risk groups were adjusted by menopausal status, treatment, tumor size, histological grade and PgR status. The adjusted hazard ratio of MS risk group was 3.44 (1.27-9.34) (Table 27). Again, tumor size was the only other significant factor in this multivariate analysis (HR=1.45 per cm increase, p=0.0049). Therefore, the gene signature has independent prognostic value for DMFS over the traditional clinicopathological risk factors and captures part of the information of these factors.

Association of MS Risk Groups with Other Clinical and Pathological Factors

MS risk group had very significant association with histological grade (Crammer's V=0.54, p<0.0001 for chi-sq test for association). For 74 grade 1 tumors, only 4 (5.4%) were MS high-risk. In contrary, 54 (47.8%) of 113 grade 2 and 37 (78.7%) of 47 grade 3 tumors were MS high-risk.

MS risk groups were also associated with tumor subtypes (Cramer's V=0.25, p=0.02). While 23 (29.8%) of 77 Scirrhous tumors were MS high-risk, 45 (41.7%) of 108 Papillotubular tumors and 24 (63.2%) of 38 solid-tubular were MS high-risk.

While tumor size is larger in the MS high-risk group (2.23 cm and 1.93 in MS high and low-risk groups respectively, ANOVA p-value=0.037), there was no significant association of MS with age (p=0.29). Results were summarized in Table 26.

Performance of the Molecular Signature in Different Clinical Subgroups

MS risk group can best predict distant metastases in young (age ≦55 years), pre-menopausal women with tumors that were ≦2 cm, low grade (grade 1 and 2) and PgR+ve. Hazard ratio of MS risk groups was 4.5 (1.2-17.3) in tumors ≦2 cm and 2.3 (0.92-5.6) in tumors >2 cm. In pre-menopausal women, HR was 6.0 (1.6-23.3) while it was 2.1 (0.83-5.1) in post-menopausal women. For those with tumors of histological grade 1 and 2, HR was 3.6 (1.5-8.4) while HR was 2.4 (0.29-18.8) in grade 3 tumors. HR of MS risk group was 3.5 (1.4-9.0) in PgR+ve tumors while it was 2.1 (0.57-7.49) in PgR−ve tumors (Table 28).

Diagnostic Accuracy and Predictive Values

Sensitivity, specificity, PPV and NPV of MS risk groups to predict distant metastasis in 5 years were shown in Table. Sensitivity of MS risk group was 0.81 (0.60-0.92) while the specificity was 0.65 (0.58-0.71). Using the estimated 5-year distant metastasis rate of 0.095, PPV and NPV were estimated to be 0.19 (0.15-0.24) and 0.97 (0.93-0.99) respectively (Table 29). High NPV of the MS risk group was important for it to be used for ruling out more aggressive treatment such as chemotherapy for patients with low-risk. ROC curve of continuous MS to predict distant metastasis within 5 years was shown in FIG. 14 and AUC was estimated to b 0.73 (0.63-0.84).

Time Dependence of the Prognostic Signature

Annualized hazard rates for MS high and low-risk groups were shown in FIG. 15a while the time-dependence of the hazard ratio between two groups was shown in FIG. 15b. For the high-risk group, annual hazard rate peaked at 3.5% around year 3 from surgery and then slowly decreased over the next few years. However, the annualized hazard rate in the low-risk group showed slight but steady increase in the 10-year period that had follow-up. Subsequently, hazard ratio of MS risk groups was time dependent. It was 4.8, 3.4 and 1.8 at year 2, 5 and 10, respectively.

As seen from this example and the previous examples, the 14 gene signature is shown to be an effective risk predictor in breast cancer patients of both Caucasian and Asian ethnic background, indicating the robustness of the 14 gene prognostic signature.

All publications and patents cited in this specification are herein incorporated by reference in their entirety. Various modifications and variations of the described compositions, methods and systems of the invention will be apparent to those skilled in the art without departing from the scope and spirit of the invention. Although the invention has been described in connection with specific preferred embodiments and certain working examples, it should be understood that the invention as claimed should not be unduly limited to such specific embodiments. Indeed, various modifications of the above-described modes for carrying out the invention that are obvious to those skilled in the field of molecular biology, genetics and related fields are intended to be within the scope of the following claims.

TABLE 1

Clinical and pathological characteristics of patients from CPMC and Guy's Hospital
Clinical and pathological characteristics of node-negative, ER-positive, untreated patients

| Characteristics | Training (UCSF) n = 142 | Validation (Guy's) n = 280 |
|---|---|---|
| Age | | |
| ≦55 yrs | 40 (28.2%) | 144 (51.4%) |
| >55 yrs | 102 (71.8%) | 136 (48.6%) |
| Mean (Std. dev.) | 62 yrs (12.6) | 55.5 yrs (11.6) |
| Min.-Max. | 31 yrs-89 yrs | 29 yrs-87 yrs |
| Tumor diameter | | |
| ≦2 cm | 126 (88.7%) | 167 (59.6%) |
| >2 cm | 8 (5.6%) | 113 (40.4%) |
| Missing | 8 (5.6%) | 0 (0%) |
| Mean (Std. Dev.) | 1.28 cm (0.50) | 1.93 cm (0.85) |

TABLE 1-continued

Clinical and pathological characteristics of patients from CPMC and Guy's Hospital
Clinical and pathological characteristics of node-negative, ER-positive, untreated patients

| Characteristics | Training (UCSF) n = 142 | Validation (Guy's) n = 280 |
|---|---|---|
| Tumor grade | | |
| Grade 1 | 74 (52.1%) | 60 (21.4%) |
| Grade 2 | 61 (43%) | 166 (59.3%) |
| Grade 3 | 4 (2.8%) | 54 (19.3%) |
| Missing | 3 (2.1%) | 0 (0%) |
| Stage | | |
| I | 117 (82.4%) | 167 (59.6%) |
| IIA | 25 (17.6%) | 113 (40.4%) |
| Distant Recurrence | | |
| Yes | 31 (21.8%) | 66 (23.4%) |
| No | 111 (78.2%) | 214 (76.6%) |
| Death of all cause | | |
| Yes | 56 (39.4%) | 135 (48.2%) |
| No | 86 (60.6%) | 145 (51.8%) |
| Median follow up | 8.7 yrs | 15.6 yrs |

TABLE 2

Genes comprising the 14-gene metastasis prognostic panel and endogenous controls.

| Gene | MS constant ai | Ref Seq | Description | Reference |
|---|---|---|---|---|
| CENPA | 0.29 | NM_001809 | centromere protein A, 17 kDa | Black, B. E., Foltz, D. R., et al., Nature 430(6999): 578-582 (2004) |
| PKMYT1 | 0.29 | NM_004203 | membrane-associated tyrosine-and thereonine-specific cdc2-inhibitory kinase | Bryan, B. A., Dyson, O. F. et al., J. Gen. Virol. 87 (PT 3), 519-529 (2006) |
| MELK | 0.29 | NM_014791 | maternal embryonic leucine zipper kinase | Beullens, M., Vancauwenbergh, S. et al., J. Biol. Chem. 280 (48), 40003-40011 (2005) |
| MYBL2 | 0.29 | NM_002466 | v-myb myeloblastosis viral oncogene homolog (avian)-like 2 | Bryan, B. A., Dyson, O. F. et al., J. Gen. Virol. 87 (PT 3), 519-529 (2006) |
| BUB1 | 0.27 | NM_004366 | BUB1 budding uninhibited by benzimidazoles 1 homolog | Morrow, C. J., Tighe, A. et al., J. Cell. Sci. 118 (PT 16), 3639-3652 (2005) |
| RACGAP1 | 0.29 | NM_013277 | Rac GTPase activating protein 1 | Niiya, F., Xie, X. et al., J. Biol. Chem. 280 (43), 36502-36509 (2005) |
| TK1 | 0.27 | NM_003258 | thymidine kinase 1, soluble | Karbownik, M., Brzezianska, E. et al., Cancer Lett. 225 (2), 267-273 (2005) |
| UBE2S | 0.27 | NM_014501 | ubiquitin-conjugating enzyme E2S | Liu, Z., Diaz, L. A. et al., J. Biol. Chem. 267 (22), 15829-15835 (1992) |
| DC13 | 0.22 | AF201935 | DC13 protein | Gu, Y., Peng, Y. et al., Direct Submission, Submitted (05-NOV-1999) Chinese National Human Genome Center at Shanghai, 351 Guo Shoujing Road, Zhangjiang Hi-Tech Park, Pudong, Shanghai 201203, P. R. China |
| RFC4 | 0.25 | NM_002916 | replication factor C (activator 1) 4, 37 kDa | Gupte, R. S., Weng, Y. et al., Cell Cycle 4 (2), 323-329 (2005) |
| PRR11 (FLJ11029) | 0.26 | NM_018304 | proline rich 11 | Weinmann, A. S., Yan, P. S. et al., Genes Dev. 16 (2), 235-244 (2002) |
| DIAPH3 | 0.23 | NM_030932 | diaphanous homolog 3 (*Drosophila*) | Katoh, M. and Katoh, M., Int. J. Mol. Med. 13 (4), 473-478 (2004) |
| ORC6L | 0.28 | NM_014321 | origin recognition complex, subunit 6 homolog-like (yeast) | Sibani, S., Price, G. B. et al., Biochemistry 44 (21), 7885-7896 (2005) |
| CCNB1 | 0.23 | NM_031966 | cyclin B1 | Zhao, M., Kim, Y. T. et al., Exp Oncol 28 (1), 44-48 (2006) |
| PPIG | EC | NM_004792 | peptidylprolyl isomerase G | Lin, C. L., Leu, S. et al., Biochem. Biophys. Res. Commun. 321 (3), 638-647 (2004) |
| NUP214 | EC | NM_005085 | nucleoporin 214 kDa | Graux, C., Cools, J. et al., Nat. Genet. 36 (10), 1084-1089 (2004) |
| SLU7 | EC | NM_006425 | step II splicing factor | Shomron, N., Alberstein, M. et al., J. Cell. Sci. 118 (PT 6), 1151-1159 (2005) |

NOTE:
PCR primers for expression profiling of all genes disclosed herein were designed to amplify all transcript variants known at time of filing.
EC = Endogenous Control.
Ref Seq = NCBI reference sequence for one variant of this gene.

TABLE 3

Primers used in gene expression profiling.

| Gene | Sequence | SEQ ID | Orientation |
|---|---|---|---|
| BUB1 | CATGGTGGTGCCTTCAA | SEQ ID NO: 1 | Upper |
| CCNB1 | GCCAAATACCTGATGGAACTAA | SEQ ID NO: 3 | Upper |
| CENPA | CAGTCGGCGGAGACAA | SEQ ID NO: 5 | Upper |
| DC13 | AAAGTGACCTGTGAGAGATTGAA | SEQ ID NO: 7 | Upper |
| DIAPH3 | TTATCCCATCGCCTTGAA | SEQ ID NO: 9 | Upper |
| MELK | AGAGACGGGCCCAGAA | SEQ ID NO: 11 | Upper |
| MYBL2 | GCGGAGCCCCATCAA | SEQ ID NO: 13 | Upper |
| ORC6L | CACTTCTGCTGCACTGCTTT | SEQ ID NO: 15 | Upper |
| PKMYT1 | CTACCTGCCCCCTGAGTT | SEQ ID NO: 17 | Upper |
| PRR11 | TGTCCAAGCTGTGGTCAAA | SEQ ID NO: 19 | Upper |
| RACGAP1 | GACTGCGAAAAGCTGGAA | SEQ ID NO: 21 | Upper |
| RFC4 | TTTGGCAGCAGCTAGAGAA | SEQ ID NO: 23 | Upper |
| TK1 | GATGGTTTCCACAGGAACAA | SEQ ID NO: 25 | Upper |
| UBE2S | CCTGCTGATCCACCCTAA | SEQ ID NO: 27 | Upper |
| NUP214 | CACTGGATCCCAAGAGTGAA | SEQ ID NO: 29 | Upper |
| PPIG | TGGACAAGTAATCTCTGGTCAA | SEQ ID NO: 31 | Upper |
| SLU7 | TGCCAATGCAGGAAAGAA | SEQ ID NO: 33 | Upper |
| BUrn | GCTGAATACATGTGAGACGACAA | SEQ ID NO: 2 | Lower |
| CCNB1 | CTCCTGCTGCAATTTGAGAA | SEQ ID NO: 4 | Lower |
| CENPA | AAGAGGTGTGTGCTCTTCTGAA | SEQ ID NO: 6 | Lower |
| DC13 | CGCCCTGCCCAACAA | SEQ ID NO: 8 | Lower |
| DIAPH3 | TGCTCCACACCATGTTGTAA | SEQ ID NO: 10 | Lower |
| MELK | CAACAGTTGATCTGGATTCACTAA | SEQ ID NO: 12 | Lower |
| MYBL2 | CATCCTCATCCACAATGTCAA | SEQ ID NO: 14 | Lower |
| ORC6L | GGATGTGGCTACCATTTTGTTT | SEQ ID NO: 16 | Lower |
| PKMYT1 | AGCATCATGACAAGGACAGAA | SEQ ID NO: 18 | Lower |
| PRR1 1 | TCTCCAGGGGTGATCAGAA | SEQ ID NO: 20 | Lower |
| RACGAP1 | TTGCTCCTCGCTTAGTTGAA | SEQ ID NO: 22 | Lower |
| RFC4 | CACGTTCATCAGATGCATTTAA | SEQ ID NO: 24 | Lower |
| TK1 | GGATCCAAGTCCCAGCAA | SEQ ID NO: 26 | Lower |
| UIBE2S | GCATACTCCTCGTAGTTCTCCAA | SEQ ID NO: 28 | Lower |
| NUP214 | TGATCCCACTCCAAGTCTAGAA | SEQ ID NO: 30 | Lower |
| PPIG | GTATCCGTACCTCCGCAAA | SEQ ID NO: 32 | Lower |
| SLU7 | TGGTATCTCCTGTGTACCTAACAAA | SEQ ID NO: 34 | Lower |

TABLE 4

Mean (μ) and standard deviation (σ) of gene expression levels of the fourteen genes in the signature in 142 samples from CPMC (ai are the loadings on the first principal components)

| Gene | ai | μ | σ |
|---|---|---|---|
| CENPA | 0.29 | −0.18 | 1.40 |
| TK1 | 0.27 | −1.07 | 1.68 |
| BUB1 | 0.27 | 2.69 | 1.78 |
| PRR11 | 0.26 | 5.25 | 1.90 |
| UBE2S | 0.27 | 2.64 | 1.41 |
| DC13 | 0.22 | 0.47 | 1.15 |
| DIAPH3 | 0.23 | 1.90 | 1.34 |
| MELK | 0.29 | −1.77 | 1.41 |
| MYBL2 | 0.29 | 2.54 | 1.88 |
| PKMYT1 | 0.29 | −0.35 | 1.73 |
| RFC4 | 0.25 | 1.25 | 0.99 |
| ORC6L | 0.28 | 1.98 | 1.43 |
| RACGAP1 | 0.29 | 4.00 | 1.09 |
| CCNB1 | 0.23 | 3.20 | 1.66 |

TABLE 5

Table 5. Distant metastasis-free and overall survival rates for low-risk and high-risk prognosis group at 5 and 10 years for patients from CPMC

| Group | No. of patients | Metastsis-free survival rate 5-yr (std. error) | Metastsis-free survival rate 10-yr (std. error) | Overall survival rate 5-yr (std. error) | Overall survival rate 10-yr (std. error) |
|---|---|---|---|---|---|
| Low risk | 71 | 0.96 (0.025) | 0.90 (0.037) | 0.90 (0.036) | 0.78 (0.059) |
| High risk | 71 | 0.74 (0.053) | 0.62 (0.066) | 0.79 (0.049) | 0.48 (0.070) |
| All | 142 | 0.85 (0.031) | 0.76 (0.040) | 0.84 (0.031) | 0.63 (0.048) |

TABLE 6

Table 6. Univariate and multivariate Cox proportional hazard regression analyses of 14-gene prognostic signature, tumor size, tumor grade and age for patients from CPMC

| Variable | Univariate analysis Hazard ratio (95% CI) | P Value | Multivariate analysis Hazard ratio (95% CI) | P Value |
|---|---|---|---|---|
| 14-gene signature | 4.23 (1.82-9.85) | 0.0008 | 3.26 (1.26-8.38) | 0.014 |
| Age | 1.00 (0.97-1.03) | 0.850 | 1.00 (0.98-1.03) | 0.810 |
| Tumor size | 1.07 (1.00-1.14) | 0.050 | 1.03 (0.96-1.10) | 0.450 |
| Tumor grade (moderate + high) | 2.18 (1.04-4.59) | 0.040 | 1.26 (0.55-2.87) | 0.580 |

For 14-gene prognostic signature, hazard ratio compares high-risk vs. low-risk groups using median MS (CV) to classify patients. For age, hazard ratio is given as the hazard increase for each year increase in age. For tumor size, hazard ratio is given as hazard increase per each centimeter increase in diameter. For tumor grade, hazard of the group with medium and high-grade tumors vs. low-grade tumors.

TABLE 7

| Gene | M value |
|---|---|
| PPIG | 0.8046 |
| SLU7 | 0.8741 |
| NUP214 | 0.8886 |
| PPP1CA | 1.0256 |
| TERF2 | 1.1907 |
| EEF1A1 | 1.1994 |

TABLE 8

| Gene | M value |
|---|---|
| PPIG | 0.5697 |
| NUP214 | 0.5520 |
| SLU7 | 0.6075 |

TABLE 9

Table 9. Prognostic values of the molecular prognostic signature using median MS (CV) as cut point to predict distant metastasis within 5 years and metastasis-free in more than 5 years for patients from CPMC (A). Distant metastasis within 5 years - prognosis vs. actual outcome

| Group | Distant Metastasis Within 5 yr (n = 21) | Disease-free >5 yr (n = 95) |
|---|---|---|
| High risk by MS | 18 | 39 |
| Low risk by MS | 3 | 56 |

(B). Diagnostic metrics of prognosis signature to predict distant metastasis within 5 years

|  | Value | 95% CI |
|---|---|---|
| Sensitivity | 0.86 | 0.65-0.95 |
| Specificity | 0.59 | 0.49-0.63 |
| Odds ratio | 8.62 | 2.37-31.26 |
| PLR | 2.09 | 1.55-2.81 |
| NLR | 0.24 | 0.084-0.70 |
| PPV* | 0.26 | 0.21-0.33 |
| NPV* | 0.96 | 0.89-0.99 |

PLR—positive likelihood ratio,
NLR—negative likelihood ratio,
PPV—positive predictive value,
NPV—negative predictive value
*Predictive values were calculated with prevalence of distant metastasis at 5 years estimated to be 0.15 from the current data.
**Individuals with distant metastasis in more than 5 years and those censored before 5 years were not included.

TABLE 10

Hazard ratios (unadjusted) (with 95% confidence interval) and p values for various risk classification for untreated patients from Guy's Hospital

| Classification | Time to distant metastases | Overall Survival |
|---|---|---|
| Gene signature (high risk vs. low risk) | 6.12 (2.23-16.83) p = 0.0004 | 2.49 (1.50-4.14) p = 0.0004 |
| Adjuvant! (high risk vs. low risk) | 2.63 (1.30-5.32) p = 0.007 | 2.89 (1.71-4.87) p < 0.0001 |
| Age (≦55 yr vs. >55 yr) | 1.45 (0.89-2.36) p = 0.13 | 2.91 (2.03-4.18) p < 0.0001 |
| Tumor size (T2 vs.T1) | 2.27 (1.39-3.69) p = 0.001 | 1.60 (1.14-2.25) p = 0.0062 |
| Histologic grade (grade 2 + 3 vs. grade 1) | 2.56 (1.17-5.61) p = 0.019 | 2.56 (1.44-4.54) p = 0.0013 |

TABLE 11

Univariate and multivariate Cox model of time to distant metastases for 14-gene prognostic signature, tumor size, tumor grade and age for untreated patients from Guy's Hospital

|  | Univariate analysis | | Multivariate analysis | |
| --- | --- | --- | --- | --- |
| Variable | Hazard ratio (95% Cl) | p-value | Hazard ratio (95% Cl) | p-value |

Table 11a Univariate and multivariate Cox model of time to distant metastases (DMFS) for 14-gene prognostic signature, tumor size, tumor grade and age

| | | | | |
| --- | --- | --- | --- | --- |
| 14-gene signature | 6.12 (2.23-16.83) | 0.0004 | 4.81 (1.71-13.53) | 0.003 |
| Age | 1.03 (1 00-1.05) | 0.024 | 1.01 (0.99-1.04) | 0.251 |
| Tumor size | 1.74 (1.24-2.44) | 0.001 | 1.39 (0 97-2.00) | 0.076 |
| Grade 2 | 2.45 (1.10-5.43) | 0.028 | 1.43 (0.63-3.23) | 0.390 |
| Grade 3 | 2.98 (1.21-7.30) | 0.017 | 1.40 (0.55-3.53) | 0.478 |

For 14-gene prognostic signature, hazard ratio compares high-risk vs. low-risk groups using formerly defined zero MS as cutpoint toclassify patients. For age, hazard ratio is given as the hazard increase for each year increase in age. For tumor size, hazard ratio is given as hazard increase per each centimeter increase in diameter. For tumor grade, hazards of the groups with grade 2 and grade 3 tumors were compared to grade 1 tumors.

TABLE 11-continued

Univariate and multivariate Cox model of time to distant metastases for 14-gene prognostic signature, tumor size, tumor grade and age for untreated patients from Guy's Hospital

|  | Univariate analysis | | Multivariate analysis | |
| --- | --- | --- | --- | --- |
| Variable | Hazard ratio (95% Cl) | p-value | Hazard ratio (95% Cl) | p-value |

Table 11b Univariate and multivariate Cox model of time to distant metastases (DMFS) for risk groups by MS and by Adjuvant!

| | | | | |
| --- | --- | --- | --- | --- |
| 14-gene signature | 6.12 (2.23-16.83) | 0.0004 | 5.32 (1.92-14.73) | 0.001 |
| Adjuvant! | 2.63 (1.30-5.32) | 0.007 | 2.06 (1.02-4.19) | 0.045 |

For 14-gene prognostic signature, hazard ratio compares high-risk vs. low-risk groups using formerly defined zero MS as cutpoint toclassify patients. For Adjuvant!, hazard ratio compares high-risk vs low-risk groups using cut point of 20% relapse probability in 10 years as calcuated by Adjuvant! Online program.

TABLE 12

Distant metastasis free and overall survival rates for low-risk and high-risk groups by MS at 5 and 10 years for untreated patients from Guy's Hospital
Distant metastasis-free and overall survival rates for low-risk and high-risk prognosis group by MS at 5 and 10 years

| | | Metastsis-free survival rate | | Overall survival rate | |
| --- | --- | --- | --- | --- | --- |
| Group | No. of patients | 5-yr (std. error) | 10-yr (std. error) | 5-yr (std. error) | 10-yr (std. error) |
| Low risk | 71 | 0.99 (0.014) | 0.96 (0.025) | 0.97 (0.020) | 0.94 (0.028) |
| High risk | 209 | 0.86 (0.025) | 0.76 (0.031) | 0.92 (0.019) | 0.71 (0.032) |
| All | 280 | 0.89 (0.019) | 0.81 (0.024) | 0.93 (0.015) | 0.77 (0.026) |

TABLE 13

Subgroup analyses: hazard ratio of MS risk groups for time to distant metastases (DMFS) in different subgroups of Adjuvant!, histological grade, tumor size, age and menopausal status for untreated patients from Guy's Hospital

| | no. of patients | no. of events | Hazard ratio of MS risk group (95% CI) | p-value |
| --- | --- | --- | --- | --- |
| Adjuvant! | | | | |
| High risk | 205 | 57 | 3.72 (1.34-10.28) | 0.0114 |
| Low risk | 75 | 9 | Infinity* | 0.01 |
| Tumor grade | | | | |
| High grade (grade 2, 3) | 220 | 59 | 4.59 (1.44-14.67) | 0.010 |
| Low grade (grade 1) | 60 | 7 | 7.58 (0.91-63.08) | 0.061 |
| Tumor size | | | | |
| ≦2 cm | 167 | 28 | 14.16 (1.92-104.22) | 0.009 |
| >2 cm | 113 | 38 | 2.64 (0.81-8.58) | 0.110 |
| Age | | | | |
| ≦55 yrs | 144 | 30 | 13.58 (1.85-99.74) | 0.010 |
| >55 yrs | 136 | 36 | 3.45 (1.06-11.26) | 0.040 |
| Menopausal status | | | | |
| Premenopausal | 102 | 21 | 7.85 (1.05-58.49) | 0.044 |
| Postmenopausal | 157 | 40 | 4.88 (1.51-15.84) | 0.008 |

*34 MS low-risk with 0 events and 41 MS high-risk with 9 events

TABLE 14

Diagnostic accuracy and predictive values of MS and Adjuvant! risk groups for distant metastases within 10 years for untreated patients from Guy's Hospital

| Risk Classification | Distant Metastases within 10 years | | | |
|---|---|---|---|---|
| | Sensitivity 95% CI | Specificity 95% CI | PPV 95% CI | NPV 95% CI |
| MS risk group | 0.94 (0.84-0.98) | 0.3 (0.24-0.37) | 0.23 (0.21-0.25) | 0.97 (0.88-0.99) |
| Adjuvant! risk group | 0.90 (0.78-0.96) | 0.31 (0.26-0.38) | 0.23 (0.20-0.25) | 0.93 (0.85-0.97) |

TABLE 15

Clinical and Pathological Characteristics of both Untreated and Treated Patients from University of Muenster

| Characteristics | All Patients N = 96 | All Treated N = 62 | Tamoxifen Treated Only N = 54 |
|---|---|---|---|
| Age | | | |
| Mean (SD) | 56.64 (12.6) | 56.43 (12.4) | 57.63 (12.1) |
| >55 yrs | 38 (40.6%) | 26 (41.9%) | 26 (48.1%) |
| <55 yrs | 37 (38.5%) | 27 (43.5%) | 22 (40.7%) |
| Unknown | 20 (20.8%) | 9 (14.5%) | 6 (11.1%) |
| T Stage | | | |
| 1 | 56 (58.3%) | 37 (59.7%) | 33 (61.1%) |
| 1C | 1 (1.0%) | 1 (1.6%) | 1 (1.9%) |
| 2 | 37 (38.5%) | 22 (35.5%) | 18 (33.3%) |
| Unknown | 2 (2.1%) | 2 (3.2%) | 2 (3.7%) |
| Grade | | | |
| Poor | 15 (15.6%) | 11 (17.7%) | 9 (16.7%) |
| Moderate | 41 (42.7%) | 31 (50.0%) | 25 (46.3%) |
| Good | 9 (9.4%) | 6 (9.7%) | 6 (11.1%) |
| Unknown | 31 (32.3%) | 14 (22.6%) | 14 (25.9%) |
| Distant Metastasis | | | |
| Yes | 27 (28.1%) | 16 (25.8%) | 14 (25.9%) |
| Follow Up | | | |
| Median (months) | 60 | 70.4 | 66.5 |

TABLE 16

Distant-metastasis-free survival rates in MS high-risk and low-risk patients from University of Muenster

| Groups | No. of Patients | Risk Group | No. of Patients | 5-yr DMFS Rate (SE) |
|---|---|---|---|---|
| All Patients | 96 | High | 48 | 0.61 (0.072) |
| | | Low | 48 | 0.88 (0.052) |
| All Treated | 62 | High | 32 | 0.66 (0.084) |
| | | Low | 30 | 0.89 (0.060) |
| Tamoxifen Treated Alone | 54 | High | 26 | 0.65 (0.084) |
| | | Low | 28 | 0.88 (0.065) |

TABLE 17

Clinical and pathological characteristics of patients from 205 treated patients from Guy's Hospital

| Characteristics | Node-negative ER-positive (n = 205) |
|---|---|
| Menopausal Status | |
| Premenopausal | 31 (15.12%) |
| Perimenopausal | 4 (1.95%) |
| Postmenopausal | 165 (80.49%) |
| Unknown | 5 (2.44%) |
| Age | |
| ≤55 yrs | 74 (36.1%) |
| >55 yrs | 131 (63.9%) |
| Mean (Std. dev.) | 59.3 (10.4) |
| Min.-Max. | 33-86 |
| Tumor diameter | |
| ≤2 cm | 138 (67.32%) |
| >2 cm | 67 (32.68%) |
| Mean (Std. Dev.) | 1.67 (1.0) |
| Min.-Max. | 0-3.0 |
| Histological Grade | |
| Grade 1 | 60 (29.27%) |
| Grade 2 | 98 (47.8%) |
| Grade 3 | 47 (22.93%) |
| Stage | |
| I | 138 (67.32%) |
| II | 67 (32.68%) |
| Subtypes | |
| Ductal NOS | 164 (80.0%) |
| Lobular Classic | 22 (10.73%) |
| Lobular Varient | 3 (1.46%) |
| Tubular | 8 (3.9%) |
| Mucinous | 6 (2.93%) |
| Papillary | 1 (0.49%) |
| Apocrine | 1 (0.49%) |
| Distant Recurrence | |
| Yes | 17 (8.29%) |
| No | 188 (91.71%) |
| Any recurrence | |
| Yes | 17 (8.9%) |
| No | 188 (91.71%) |
| Death (Any cause) | |
| Yes | 44 (21.46%) |
| No | 161 (78.54%) |
| Death (Breast Cancer) | |
| Yes | 16 (7.8%) |
| No | 189 (92.20%) |
| Median follow up | 9.3 yrs |

TABLE 18

Five-year and ten-year distant-metastasis-free survival rates in high, intermediate, and low MS groups in Guy's treated samples

| | No. of Patients | DM | 5 yr DMFS (SE) | 10 yr DMFS (SE) |
|---|---|---|---|---|
| High | 40 | 7 | 0.872 (0.054) | 0.804 (0.068) |
| Intermediate | 29 | 2 | 0.966 (0.034) | 0.966 (0.034) |
| Low | 136 | 8 | 0.970 (0.015) | 0.921 (0.028) |
| Int. + Low | 165 | 10 | 0.969 (0.014) | 0.928 (0.025) |
| All | 205 | 17 | 0.950 (0.015) | 0.904 (0.0239) |

TABLE 19

Univariate and multivariate Cox proportional hazard regression of MS risk groups, age, tumor size, and histological grade in Guy's treated samples

|  | Univariate | | | Multivariate | | |
|---|---|---|---|---|---|---|
|  | Hazard Ratio | 95% CI | P-value | Hazard Ratio | 95% CI | P-value |
| MS high vs. low risk | 3.25 | 1.24-8.54 | 0.017 | 5.82 | 1.71-19.75 | 0.0047 |
| Age (per year) | 1.03 | 0.98-1.08 | 0.27 | 1.03 | 0.98-1.08 | 0.31 |
| Tumor size (per cm) | 1.28 | 0.77-2.14 | 0.34 | 1.17 | 0.68-2.03 | 0.57 |
| Grade 2 vs. Grade 1 | 3.50 | 0.78-15.79 | 0.10 | 2.64 | 0.56-12.45 | 0.22 |
| Grade 3 vs. Grade 1 | 2.72 | 0.50-14.86 | 0.25 | 0.62 | 0.081-4.76 | 0.65 |

TABLE 20

Association of MS risk groups with age, tumor size and histological grade in Guy's treated patients

Age

|  | N | Mean | Std. Dev. |
|---|---|---|---|
| High | 40 | 59.3 | 8.3 |
| Int. + Low | 165 | 59.3 | 10.8 |
| One-way ANOVA | | p = 0.34 | |

Tumor Size

|  | N | Mean | Std. Dev. |
|---|---|---|---|
| High | 40 | 1.87 | 0.92 |
| Int. + Low | 165 | 1.61 | 101 |
| One-way ANOVA | | p = 0.14 | |

Histological grade

|  | Grade 1 | Grade 2 | Grade 3 |
|---|---|---|---|
| High | 0 | 9 | 31 |
| Int. + Low | 60 | 89 | 16 |
| Crammer's V = 0.65 | | chi-sq test for association p-value < 0.0001 | |

TABLE 21

Performance of MS risk groups (High vs. low risk) in subgroups of age, tumor size, histological grade and menopausal status

|  | N patient | N DM | HR | L95% CI | U95% CL | P-Value |
|---|---|---|---|---|---|---|
| All | 205 | 17 | 3.25 | 1.24 | 8.54 | 0.017 |
| Histologic Grade | | | | | | |
| Grade 1 | 60 | 2 | NA | only low score | | |
| Grade 2 | 98 | 11 | 10.72 | 3.00 | 38.36 | 0.0003 |
| Grade 3 | 47 | 4 | 1.53 | 0.16 | 14.66 | 0.715 |
| Tumor size | | | | | | |
| <=2 cm | 138 | 11 | 3.66 | 1.07 | 12.57 | 0.0392 |
| >2 cm | 67 | 6 | 2.99 | 0.60 | 14.82 | 0.18 |
| Age | | | | | | |
| <=55 yrs | 74 | 5 | 7.38 | 1.00 | 54.66 | 0.0503 |
| >55 yrs | 131 | 12 | 2.78 | 0.88 | 8.75 | 0.0813 |
| Menopausal Status | | | | | | |
| premenopausal | 31 | 1 | NA | | | |
| postmenopausal | 165 | 15 | 2.84 | 1.01 | 7.99 | 0.0476 |

TABLE 22

Diagnostic values of MS risk groups (high vs. low risk) in Guy's treated samples

|  | 5 yr | 10 yr |
|---|---|---|
| Sensitivity | 0.50 (0.24-0.76) | 0.44 (0.23-0.67) |
| Specificity | 0.82 (0.76-0.87) | 0.85 (0.76-0.92) |
| PPV | 0.128 (0.068-0.227) | 0.24 (0.13-0.41) |
| NPV | 0.969 (0.944-0.983) | 0.93 (0.90-0.96) |

TABLE 23

Clinicopathological characteristics of 234 Japanese samples

|  | Post-menopause | Pre-menopause | All |
|---|---|---|---|
|  | 112 (47.9%) | 122 (52.1%) | 234 (100%) |
| Age | | | |
| <=55 yrs | 32 (28.6%) | 122 (100%) | 154 (65.8%) |
| >55 yrs | 80 (71.4%) | 0 (0%) | 80 (34.2%) |
| Mean (Std. dev.) | 60.8 (7.8) | 44.8 (6.0) | 52.5 (10.6) |
| Min.-Max. | 43-81 | 25-54 | 25-81 |
| Tumor diameter | | | |
| <=2 cm | 65 (58.0%) | 81 (66.4%) | 146 (62.4%) |
| >2 cm | 47 (42.0%) | 41 (33.6%) | 88 (37.6%) |
| Mean (Std. Dev.) | 2.15 (1.0) | 1.96 (1.2) | 2.05 (1.1) |
| Min.-Max. | 0.3-8.4 | 0.1-6.5 | 0.1-8.4 |
| Histologic grade | | | |
| Grade 1 | 28 (25%) | 46 (37.7%) | 74 (31.6%) |
| Grade 2 | 56 (50%) | 57 (46.7%) | 113 (48.3%) |
| Grade 3 | 28 (25%) | 19 (15.6%) | 47 (20.1%) |
| Tumor subtype | | | |
| II a Papillotubular | 42 (37.5%) | 66 (54.1%) | 108 (46.2%) |
| II a Scirrhous | 41 (36.6%) | 36 (29.5%) | 77 (32.9%) |
| II a Solid-tubular | 24 (21.4%) | 14 (11.5%) | 38 (16.2%) |
| II b Invasive Lobular | 2 (1.8%) | 2 (1.6%) | 4 (1.7%) |
| II b Medullary | 1 (0.9%) | 0 (0%) | 1 (0.4%) |
| II b Mucinous | 2 (1.8%) | 4 (3.3%) | 6 (2.6%) |
| Stage | | | |
| I | 65 (58.0%) | 81 (66.4%) | 146 (62.4%) |
| IIA | 44 (39.3%) | 36 (29.5%) | 80 (34.2%) |
| IIB | 3 (2.7%) | 5 (4.1%) | 8 (3.4%) |
| PgR | | | |
| + | 65 (58%) | 113 (92.6%) | 178 (76.1%) |
| − | 47 (42%) | 9 (7.4%) | 56 (23.9%) |
| Therapy | | | |
| Tam/Tam comb. | 112 (100%) | 102 (83.9%) | 214 (91.5%) |
| ZOL | 0 (0%) | 20 (16.1%) | 20 (8.5%) |
| Distant Metastasis | | | |

TABLE 23-continued

Clinicopathological characteristics of 234 Japanese samples

|  | Post-menopause | Pre-menopause | All |
|---|---|---|---|
| Yes | 21 (18.8%) | 10 (8.9%) | 31 (13.3%) |
| No | 91 (81.3%) | 112 (91.1%) | 203 (86.8%) |
| Death of Any Cause | | | |
| Yes | 10 (8.9%) | 9 (7.3%) | 19 (8.1%) |
| No | 102 (90.9%) | 115 (92.7%) | 215 (91.9%) |
| Recurrence (local and distant) | | | |
| Yes | 30 (26.8%) | 16 (13.1%) | 46 (19.7%) |
| No | 82 (73.2%) | 106 (86.9%) | 188 (80.3%) |
| Follow-up (years) | | | |
| Median | 9 | 8 | 8.7 |

TABLE 24

Five-year and ten-year distant-metastasis-free survival rates in different MS groups in Japanese patients

| | No. of Patients | 5 yr DMFS (SE) | 10 yr DMFS (SE) |
|---|---|---|---|
| High | 95 | 0.808 (0.042) | 0.747 (0.050) |
| Intermediate | 62 | 0.965 (0.024) | 0.912 (0.044) |
| Low | 77 | 0.974 (0.018) | 0.887 (0.047) |
| Int. + Low | 139 | 0.97 (0.015) | 0.895 (0.034) |
| All | 234 | 0.905 (0.020) | 0.837 (0.029) |

TABLE 25

Univariate and multivariate Cox proportional hazard model of time to distant metastases for MS risk groups, age, tumor size and histological grade in Japanese patients

| | Univariate | | | Multivariate | | |
|---|---|---|---|---|---|---|
| | Hazard Ratio | 95% CI | P-value | Hazard Ratio | 95% CI | P-value |
| MS high vs. int. + low | 3.32 | 1.56-7.06 | 0.0018 | 3.79 | 1.42-10.1 | 0.0078 |
| Age (per year) | 1.04 | 1.00-1.08 | 0.032 | 1.03 | 0.99-1.07 | 0.087 |
| Tissue Size (per cm) | 1.45 | 1.14-1.83 | 0.0024 | 1.4 | 1.10-1.78 | 0.007 |
| Hist. grade 2 vs. 1 | 1.47 | 0.60-3.61 | 0.40 | 0.72 | 0.24-2.14 | 0.56 |
| Hist. grade 3 vs. 1 | 2.02 | 0.75-5.44 | 0.16 | 0.55 | 0.15-2.00 | 0.36 |

TABLE 26

Association of MS risk groups with age, tumor size and histological grade in Japanese patients

Age

| | N | Mean | Std. Dev. |
|---|---|---|---|
| High | 95 | 53.4 | 10.4 |
| Int. + Low | 139 | 51.9 | 10.7 |
| One-way ANOVA | | p = 0.29 | |

Tumor Size

| | N | Mean | Std. Dev. |
|---|---|---|---|
| High | 95 | 2.23 | 1.04 |
| Int. + Low | 139 | 1.93 | 1.13 |
| One-way ANOVA | | p = 0.037 | |

Histologic grade

| | Grade 1 | Grade 2 | Grade 3 |
|---|---|---|---|
| High | 4 | 54 | 37 |
| Int. + Low | 70 | 59 | 10 |
| Crammer's V = 0.54 | chi-sq test for association p-value < 0.0001 | | |

Subtype

| | 2a Papillotular | 2a Scirrhous | 2a Solid-tubular | 2b Invasive lobular | Medullary | Mucinous |
|---|---|---|---|---|---|---|
| High | 45 | 23 | 24 | 1 | 1 | 1 |
| Int. + Low | 63 | 54 | 14 | 3 | 0 | 5 |
| Crammer's V = 0.25 | chi-sq test for association p-value = 0.01 | | | | | |

TABLE 27

Univariate and multivariate Cox proportional hazard model of time to distant metastases for MS risk groups, menopausal status, tumor size, PgR status and histological grade in Japanese patients

|  | Univariate | | | Multivariate | | |
| --- | --- | --- | --- | --- | --- | --- |
|  | Hazard Ratio | 95% CI | P-value | Hazard Ratio | 95% CI | P-value |
| MS high vs. int. + low | 3.32 | 1.56-7.06 | 0.0018 | 3.44 | 1.27-9.34 | 0.015 |
| Pre, Tam vs. Post, Tam | 0.33 | 0.13-0.81 | 0.016 | 0.45 | 0.17-1.19 | 0.11 |
| Pre, ZOL vs. Post, Tam | 1.22 | 0.42-3.58 | 0.72 | 1.8 | 0.55-5.81 | 0.33 |
| Tissue_size (per cm) | 1.45 | 1.14-1.83 | 0.0024 | 1.45 | 1.12-1.88 | 0.0049 |
| PgR (−ve vs. +ve) | 2.3 | 1.13-4.7 | 0.022 | 1.7 | 0.75-3.86 | 0.2 |
| Hist. grade 2 vs. 1 | 1.47 | 0.6-3.61 | 0.4 | 0.53 | 0.17-1.62 | 0.26 |
| Hist. grade 3 vs. 1 | 2.02 | 0.75-5.44 | 0.16 | 0.49 | 0.13-1.76 | 0.27 |

TABLE 28

Subgroup analyses: hazard ratio of MS risk groups for time to distant metastases (DMFS) in different subgroups of tumorsize, age, menopausal status, histological grade and PgR status

| Strata | Hazard Ratio | 95% CI | P-value |
| --- | --- | --- | --- |
| ALL | 3.32 | 1.56-7.06 | 0.0018 |
| Tumor <= 2 cm | 4.48 | 1.16-17.34 | 0.030 |
| Tumor > 2 cm | 2.27 | 0.92-5.62 | 0.077 |
| Age <= 55 | 4.03 | 1.38-11.81 | 0.011 |
| Age > 55 | 2.34 | 0.81-6.74 | 0.12 |
| post-menopausal | 2.06 | 0.83-5.09 | 0.12 |
| pre-menopausal | 6.01 | 1.55-23.25 | 0.0094 |
| Grade 1 & 2 | 3.57 | 1.52-8.35 | 0.0034 |
| Grade 3 | 2.35 | 0.29-18.77 | 0.42 |
| PgR+ | 3.48 | 1.35-9.0 | 0.0099 |
| PgR− | 2.06 | 0.57-7.49 | 0.27 |

TABLE 29

Diagnostic values of MS to predict distant metastasis in 5 years for Japanese samples

|  | Cut 1 (int + low combined) |
| --- | --- |
| Sensitivity | 0.81 (0.60-0.92) |
| Specificity | 0.65 (0.58-0.71) |
| PPV | 0.19 (0.15-0.24) |
| NPV | 0.97 (0.93-0.99) |

What is claimed is:

1. A method of determining risk associated with tumor metastasis in a breast cancer patient, comprising:
    (a) measuring the expression level of genes CENPA, PKMYT1, MELK, MYBL2, BUB1, RACGAP1, TK1, UBE2S, DC13, RFC4, PRR11, DIAPH3, ORC6L and CCNB1 in estrogen receptor-positive tumor cells of said breast cancer patient, thereby obtaining a metastasis score (MS) based upon the expression levels of said genes, and
    (b) determining risk of tumor metastasis for said breast cancer patient by comparing said metastasis score to a predefined metastasis score cut off threshold (MS Threshold).

2. The method of claim 1, wherein in step (b), said breast cancer patient is determined to have an increased risk of tumor metastasis if its MS is higher than the predefined MS Threshold.

3. The method of claim 1, wherein in step (b), said breast cancer patient is determined to have a decreased risk of tumor metastasis if its MS is lower than the predefined MS Threshold.

4. The method of claim 1, wherein in step (b), two or more MS Threshold values are used in determining risk of tumor metastasis for said breast cancer patient.

5. The method of claim 1 in which the breast cancer patient has no detectable tumor cells in lymph nodes.

6. The method of claim 1 in which the breast cancer patient has an increased risk of developing tumor metastasis.

7. The method of claim 1 in which the estrogen receptor-positive tumor cells are derived from formalin-fixed paraffin-embedded sections.

8. The method of claim 1 in which the estrogen receptor-positive tumor cells are derived from a tumor biopsy.

9. The method of claim 1 in which the estrogen receptor-positive tumor cells are derived from frozen tumor tissues.

10. The method of claim 1 in which mRNA of said genes are obtained from estrogen receptor-positive tumor cells, reverse transcribed to cDNA, and detected by polymerase chain reaction amplification of said cDNA.

11. The method of claim 10 in which said mRNA is enriched prior to reverse transcription and PCR amplification.

12. The method of claim 1 in which mRNA of each of said genes is reverse transcribed and amplified by the two primers associated with the corresponding gene as presented in Table 3, SEQ ID NOS. 1-30.

13. The method of claim 1 in which the expression levels of said genes are normalized against the expression level of a housekeeping gene, or an average of two or more housekeeping genes.

14. The method of claim 13 wherein the housekeeping gene is selected from the group comprising of NUP214, PPIG and SLU7.

15. The method of claim 13 in which the mRNA of said housekeeping gene is reverse transcribed and amplified by the two primers associated with said housekeeping gene as listed in Table 3, SEQ ID NOS. 29-34.

16. The method of claim 1 in which the expression level is detected by a microarray.

17. The method of claim 1 in which the metastasis score (MS) is calculated by the following:

$$MS = a0 + \sum_{i=1}^{M} ai * Gi$$

where M=14, Gi=the expression level of each gene (i) of the fourteen said genes, a0=0.022, and ai corresponds to the value presented in Table 2 for each of said genes.

18. The method of claim 17 in which the expression level Gi of each gene (i) is computed into a gene expression value Gi by the following:

$$\Delta(\Delta Ct) = (Ct_{GOI} - Ct_{EC})_{test\ RNA} - (Ct_{GOI} - Ct_{EC})_{ref\ RNA}$$

where Ct is the PCR threshold cycle of exponential target amplification, GOI=gene of interest, EC=endogenous control, test RNA=patient sample RNA, ref RNA=reference RNA.

19. The method of claim 17, wherein a0=0 and ai=1.

20. The method of claim 1 in which the metastasis score (MS) is calculated by the following:

$$MS = a0 + b * \left[\sum_{i=1}^{M} ai * Gi\right]$$

where M=14, Gi=the standardized expression level of each gene (i) of the fourteen said genes, a0=0.022, b=−0.251 and ai corresponds to the value presented in Table 2 for each of said genes.

21. The method of claim 1 in which the metastasis score (MS) is calculated by the following:

$$MS = a0 + b * \left[\sum_{i=1}^{M} ai * Gi\right]$$

where M=14, Gi=the expression level of each gene (i) of the fourteen said genes, a0=0.8657, b=−0.04778 and ai=1 for each of said genes.

22. The method of claim 1 in which the metastasis score (MS) is calculated by the following:

$$MS(\text{new}) = -1/14 * \left[\sum_{i=1}^{14} Gi\right]$$

where Gi=the expression level of each gene (i) of the fourteen said genes.

23. The method of claim 1 in which the metastasis score (MS) is calculated by adding together the expression level of each gene of the fourteen said genes.

* * * * *